(12) United States Patent
Rossi et al.

(10) Patent No.: US 8,513,401 B2
(45) Date of Patent: Aug. 20, 2013

(54) DOUBLE STRANDED NUCLEIC ACID TARGETING LOW COPY PROMOTER-SPECIFIC RNA

(75) Inventors: John J. Rossi, Alta Loma, CA (US); Daniela Castanotto, Altadena, CA (US); Gerd Pfeifer, Bradbury, CA (US); Stella Tommasi, South Pasadena, CA (US); Kevin V. Morris, Sierra Madre, CA (US); Daniel H. Kim, Duarte, CA (US)

(73) Assignee: City of Hope, Duarte, CA (US)

( * ) Notice: Subject to any disclaimer, the term of this patent is extended or adjusted under 35 U.S.C. 154(b) by 449 days.

(21) Appl. No.: 12/772,652

(22) Filed: May 3, 2010

(65) Prior Publication Data

US 2010/0267809 A1 Oct. 21, 2010

Related U.S. Application Data

(63) Continuation of application No. 11/439,440, filed on May 24, 2006, now abandoned, which is a continuation-in-part of application No. 10/776,635, filed on Feb. 12, 2004, now abandoned.

(60) Provisional application No. 60/447,013, filed on Feb. 13, 2003, provisional application No. 60/683,782, filed on May 24, 2005.

(51) Int. Cl.
*C07H 21/04* (2006.01)
*C07H 21/02* (2006.01)

(52) U.S. Cl.
USPC ........................................ 536/24.5; 536/23.1

(58) Field of Classification Search
None
See application file for complete search history.

(56) References Cited

U.S. PATENT DOCUMENTS

| | | | |
|---|---|---|---|
| 5,801,154 | A | 9/1998 | Baracchini et al. |
| 6,506,559 | B1 | 1/2003 | Fire et al. |
| 6,706,686 | B2 | 3/2004 | Long et al. |
| 2002/0086356 | A1 | 7/2002 | Tuschl et al. |
| 2002/0173478 | A1 | 11/2002 | Gewirtz |
| 2004/0224405 | A1 | 11/2004 | Leake et al. |

FOREIGN PATENT DOCUMENTS

| | | |
|---|---|---|
| WO | WO 02/44321 A2 | 6/2002 |
| WO | WO 03/022052 A1 | 3/2003 |
| WO | 2005/116226 A2 | 12/2005 |

OTHER PUBLICATIONS

Reich, S.J. et al., "Small Interfering RNA (siRNA) Targeting VEGF Effectively Inhibits Ocular Neovascularization in a Mouse Model," Molecular Vision 2003; 9:210-216.
Sorensen, D.R. et al., "Gene Silencing by Systemic Delivery of Synthetic siRNAs in Adult Mice," J. Mol. Biol. (2003), 327:761-766, © 2003 Elsevier Science Ltd.
Morrissey, D.V. et al., "Potent and Persistent in Vivo Anti-HBV Activity of Chemically Modified siRNAs," Nature Biotechnology, vol. 23, No. 8, Aug. 2005, pp. 1002-1007, © 2005 Nature Publishing Group.
Sun, L. et al., "Adenovirus-Mediated In Vivo Silencing of Anaphylatoxin Receptor C5aR," Journal of Biomedicine and Biotechnology, vol. 2006, Article ID 28945, pp. 109, Hindawi Publishing Corporation.
Aigner, A., "Delivery Systems for the Direct Application of siRNAs to Induce RNA Interference (RNAi) In Vivo," Journal of Biomedicine and Biotechnology, vol. 2006, Article ID 71659, pp. 1-15, Hindawi Publishing Corporation.
Thakker D.R. et al., "Neurochemical and Behavioral Consequences of Widespread Gene Knockdown in the Adult Mouse Brain by Using Nonviral RNA Interference," PNAS, pp. 17270-17275, Dec. 7, 2004, vol. 101, No. 49, © by The National Academy of Sciences of the USA.
Massaro, D. et al., "Noninvasive Delivery of Small Inhibitory RNA and Other Reagents to Pulmonary Alveoli in Mice," Am J. Physiol Lung Cell Mol Physiol 287: L1066-L1070, 2004, © 2004 The American Physiology Society.
Soutschek, J. et al., "Therapeutic Silencing of an Endogenous Gene by Systemic Administration of Modified siRNAs," Nature, vol. 432, Nov. 11, 2004, pp. 173-178, © 2004 Nature Publishing Group.
Zhang, X. et al., "Small Interfering RNA Targeting Heme Oxygenase-1 Enhances Ischemia-Reperfusion-Induced Lung Apoptosis," The Journal of Biological Chemistry, vol. 279, No. 11, Issue of Mar. 12, pp. 10677-10684, © 2004 by The American Society for Biochemistry and Molecular Biology, Inc.
Behlke, M., "Progress Towards In Vivo Use of siRNAs," Molecular Therapy, vol. 13, No. 4, Apr. 2006, pp. 644-670 © The American Society of Gene Therapy.
Barton, Gregory M., et al., "Retroviral delivery of small interfering RNA into primary cells," *PNAS* 99(23):14943-14945, Nov. 12, 2002.
Brummelkamp, Thijn R., et al., "A System for Stable Expression of Short Interfering RNAs in Mammalian Cells," Science 296:550-553, Apr. 19, 2002.
Caplen, Natasha J., et al., "Specific inhibition of gene expression by small double-stranded RNAs in invertebrate and vertebrate systems," PNAS 98(17):9742-9747, Aug. 14, 2001.
Clemens, James C., et al., "Use of double-stranded RNA interference in *Drosophila* cell lines to dissect signal transduction pathways," PNAS 97(12):6499-6503, Jun. 6, 2000.
Devroe, Eric, et al., "Retrovirus-delivered siRNA," BMC Biotechnology 2(15):1-5, Aug. 28, 2002.
Elbashir, Sayda M., et al., "Duplexes of 21-nucleotide RNAs mediate RNA interference in cultured mammalian cells," Nature 411:494-498, May 24, 2001.
Elbashir, Sayda M., et al., "RNA interference is mediated by 21- and 22-nucleotide RNAs," Genes & Development 15:188-200, 2001.
Fire, Andrew, "RNA-triggered gene silencing," TIG 15(9):358-363, Sep. 1999.

(Continued)

*Primary Examiner* — Amy Bowman
(74) *Attorney, Agent, or Firm* — Rothwell, Figg, Ernst & Manbeck P.C.

(57) ABSTRACT

The present invention relates to transcriptional gene silencing (TGS) in mammalian, including human, cells that is mediated by small interfering RNA (siRNA) molecules. The present invention also relates to a double stranded nucleic acid that directs methylation of histones associated with target genes that produce low copy promoter-specific RNA. It has been found that siRNAs can be used to direct methylation of histones in mammalian, including human, cells.

14 Claims, 20 Drawing Sheets

(56) References Cited

OTHER PUBLICATIONS

Fire, Andrew, "Potent and specific genetic interference by double-stranded RNA in *Caenorhabditis elegans*," Nature 391:806-811, Feb. 19, 1998.
Good, PD, et al., "Expression of small, therapeutic RNAs in human cell nuclei," Gene Therapy 4:45-54, 1997.
Hamilton, Andrew, et al., "Two clases of short interfering RNA in RNA silencing," The EMBO Journal, vol. 21, No. 17, pp. 4671-4679, 2002.
Hammond, Scott M., et al., "An RNA-directed nuclease mediates post-transcriptional gene silencing in *Drosophila* cells," Nature 404:293-296, Mar. 16, 2000.
Herman, James G., et al., "Methylation-specific PCR: A novel PCR assay for methylation status of CpG islands," Proc. Natl. Acad. Sci. USA, vol. 93, pp. 9821-9826, Sep. 1996.
Kawasaki et al., "Short hairpin type of dsRNAs that are controlled by tRNA$^{Val}$ promoter significantly induce RNAi-mediated gene silencing in the cytoplasm of human cells," Nucleic Acids Research 31(2):700-707, Jan. 2003.
Kennerdell, Jason R., et al., "Use of dsRNA-Mediated Genetic Interference to Demonstrate that frizzled and frizzled 2 Act in the Wingless Pathway," Cell 95:1017-1026, Dec. 23, 1998.
Lee et al., "Expression of small interfering RNAs targeted against HIV-1 rev transcripts in human cells," Nature Biotechnology 19:500-505, May 2002.
Lipardi, Concetta, et al., "RNAi as Random Degradative PCR: siRNA Primers Convert mRNA into dsRNAs that are Degraded to Generate New siRNAs," Cell 107:297-307, Nov. 2, 2001.
Miyagishi et al., "U6 promoter-driven siRNAs with four uridine 3' overhangs efficiently suppress targeted gene expression in mammalian cells," Nature Biotechnology 19:497-500, May 2002.
Paddison et al., "Short hairpin RNAs (shRNAs) induce sequence-specific silencing in mammalian cells," Genes and Development 16:948-958, Mar. 2002.
Paul, Cynthia P., et al., "Effective expression of small interfering RNA in human cells," Nature Biotechnology 29:505-508, May 2002.
Scherr, Michaela, et al, "Rapid determination and quantitation of the accessibility to native RNAs by antisense oligodeoxynucleotides in murine cell extracts," Nucleic Acids Research 26(22):5079-5085, 1998.
Sharp, Phillip A., et al., "RNA interference—2001," Genes & Development 15:485-490, 2001.
Shi, Y., "Mammalian RNAi for the masses," Trends in Genetics 19(1):9-12, Jan. 2003.
Shinagawa et al., "Generation of Ski-knockdown mice by expressing a long double-strand RNA from an RNA polymerase II promoter," Genes and Development 17:1340-1345, Apr. 2003.
Sijen, Titia, et al., "On the Role of RNA Amplification in dsRNA-Triggered Gene Silencing," Cell 107:465-476, Nov. 16, 2001.
Sui, Guanchao, et al., "A DNA vector-based RNAi technology to suppress gene expression in mammalian cells," PNAS, vol. 99, No. 8, pp. 5515-5520, Apr. 15, 2002.
Svoboda, Petr, et al, "Selective reduction of dormant maternal mRNAs in mouse oocytes by RNA interference," Development 127:4147-4156, 2000.
Tuschl et al., "Expanding small RNA interference," Nature Biotechnology 20:446-448, May 2002.
Wianny, Florence, et al., "Specific interference with gene function by double-stranded RNA in early mouse development," Nature Cell Biology 2:70-75, Feb. 2000.
Yu, Jenn-Yah, et al., "RNA interference by expression of short-interfering RNAs and hairpin RNAs in mammalian cells," PNAS 99(9):6047-6052, Apr. 30, 2002.
Castanotto et al., "Functional siRNA expression from transfected PCR products", 2002, RNA, 8, pp. 1454-1460.
Peel, et al., Adeno-associated virus vectors: activity and applications in the CNS, 2000, Journal of Neuroscience Methods, 98, pp. 95-104.
Elbashir et al., Duplexes of 21-nucleotide RNAs mediate RNA interference in cultured mammalian cells, 2001, Nature, vol. 411, pp. 494-498.
Miyagishi et al., U6 promoter-driven siRNAs with four uridine 3' overhangs efficiently supress targeted gene expression in mammalian cells, 2002, Nature Biotechnology, vol. 19, pp. 497-500.
Qin et al., Inhibiting HIV-1 infection in human T cells by lentiviral-mediated delivery of small interfering RNA against CCR5, 2003, PNAS, vol. 100, No. 1, pp. 183-188.
Mette et al., Transcriptional silencing and promoter methylation triggered by double-stranded RNA, 2000, the EMBO Journal, vol. 19, pp. 5194-5201.
Dammann et al., Epigenetic inactivation of a RAS association domain family protein, from the lung tumour suppressor locus 3p21.3, 2000, Nature Genetics, vol. 25, pp. 315-319.
Miki et al., De novo DNA methylation induced by siRNA targeted to endogenous transcribed sequences in gene-specific and OsMet1-independent in rice, 2008, The Plant Journal, 56, pp. 539-549.
Nguyen et al., RNAi therapeutics: An update on delivery, 2008, Current Opinion in Molecular Therapeutics, 10(2), pp. 158-167.
Kawasaki et al., Induction of DNA methylation and gene silencing by short interfering RNAs in human cells, 2004, Nature, vol. 431, pp. 211-217.
Park et al., Double-stranded siRNA targeted to the huntingtin gene does not induce DNA methylation, 2004, Biochemical and Biophysical Research Communications, 323, pp. 275-280.
Svoboda et al., Lack of homologous sequence-specific DNA methylation in response to stagle dsRNA expression in mouse oocytes, 2004, Nucleic Acids Research, vol. 32, No. 12, pp. 3601-3606.
Mathieu et al., RNA-directed DNA methylation, 2004, Journal of Cell Science, 117(21), pp. 4881-4888.
Caplen et al., dsRNA-mediated gene silencing in cultured *Drosophilia* cells: a tissue culture model for the analysis of RNA interference, 2000, Gene, 252, pp. 95-105.
Miyagishi et al., U6 promoter-driven siRNAs with four uridine 3' overhangs efficiently suppress targeted gene expression in mammalian cells, 2002, Nature Biotechnology, vol. 19, pp. 497-500.
Non-final Office Action dated Mar. 29, 2007, U.S. Appl. No. 11/439,440, filed May 24, 2006, Inventor: John J. Rossi et al, 53 pages; Response dated Oct. 1, 2007, 17 pages.
Final Office Action dated Dec. 11, 2007, U.S. Appl. No. 11/439,440, filed May 24, 2006, Inventor: John J. Rossi et al, 21 pages; Response dated Jun. 11, 2008, 180 pages.
Amendment dated Jan. 10, 2008, U.S. Appl. No. 11/439,440, filed May 24, 2006, Inventor: John J. Rossi et al, 3 pages.
Advisory Action dated Feb. 8, 2008, 4 pages.
Non-final Office Action dated Aug. 26, 2008, U.S. Appl. No. 11/439,440, filed May 24, 2006, Inventor: John J. Rossi et al, 62 pages; Response dated Feb. 26, 2009, 17 pages.
Final Office Action dated Jun. 11, 2009, U.S. Appl. No. 11/439,440, filed May 24, 2006, Inventor: John J. Rossi et al, 31 pages; Response dated Dec. 11, 2009, 191 pages.
Non-final Office Action dated Feb. 1, 2010, U.S. Appl. No. 11/439,440, filed May 24, 2006, Inventor: John J. Rossi et al, 14 pages.

Figure 3

DOUBLE STRANDED NUCLEIC ACID TARGETING LOW COPY PROMOTER-SPECIFIC RNA

CROSS-REFERENCE TO RELATED APPLICATIONS

The present application is a continuation of U.S. patent application Ser. No. 11/439,440 filed 24 May 2006, which in turn is a continuation-in-part of U.S. patent application Ser. No. 10/776,635 filed 12 Feb. 2004. U.S. patent application Ser. No. 10/776,635 is related to and claims priority under 35 U.S.C. §119(e) to U.S. provisional patent application Ser. No. 60/447,013 filed 13 Feb. 2003. U.S. patent application Ser. No. 11/439,440 is further related to and claims priority under 35 U.S.C. §119(e) to U.S. provisional patent application Ser. No. 60/683,782 filed 24 May 2005. Each of these applications is incorporated herein by reference.

This application was made with Government support under Grant Nos. AI29329, AI42552, R01 HL07470 and R01 HL83473 funded by the National Institutes of Health, Bethesda, Md. and under Grant No. 5P30 CA33572-21 funded by the National Cancer Institute, Bethesda Md. The federal government may have certain rights in this invention.

BACKGROUND OF THE INVENTION

The present invention relates to transcriptional gene silencing (TGS) in mammalian, including human, cells that is mediated by small interfering RNA (siRNA) molecules. The present invention also relates to a method for directing histone and/or DNA methylation in mammalian, including human, cells. It has been found that siRNAs can be used to direct methylation of DNA in mammalian, including human, cells.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

RNA interference (RNAi) is a process in which double stranded RNA (ds RNA) induces the postranscriptional degradation of homologous transcripts, and has been observed in a variety of organisms including plants, fungi, insects, protozans, and mammals (Moss et al., 2001; Bernstein et al., 2001; Elbashir, et al., 2001a, 2001b). RNAi is initiated by exposing cells to dsRNA either via transfection or endogenous expression. Double-stranded RNAs are processed into 21 to 23 nucleotide (nt) fragments known as siRNA (small interfering RNAs) (Elbashir et al., 2001a, 2001b). These siRNAs form a complex known as the RNA Induced Silencing Complex or RISC (Bernstein et al., 2001; Hammond et al. 2001), which functions in homologous target RNA destruction. In mammalian systems, the sequence specific RNAi effect can be observed by introduction of siRNAs either via transfection or endogenous expression of 21-23 base transcripts or longer hairpin precursors. Use of siRNAs evades the dsRNA induced interferon and PKR pathways that lead to non-specific inhibition of gene expression. (Elbashir et al., 2001a).

The discovery of siRNAs permitted RNAi to be used as an experimental tool in higher eukaryotes. Typically, siRNAs are chemically synthesized as 21 mers with a central 19 by duplex region and symmetric 2-base 3'-overhangs on the termini. These duplexes are transfected into cells lines, directly mimicking the products made by Dicer in vivo. Most siRNA sequences can be administered to cultured cells or to animals without eliciting an interferon response (Heidel et al., 2004; Ma et al., 2005; Judge et al., 2005). There are some reports that particular motifs can induce such a response when delivered via lipids (Judge et al., 2005; Sledz et al., 2003; Hornung eta 1, 2005), although a cyclodextrin-containing polycation system has been shown to deliver siRNA containing one such putative immunostimulatory motif that achieves target gene down-regulation in mice without triggering an interferon response (Hu-Lieskovan et al., 2005), even in a disseminated tumor model.

It has been recently described that chemically synthesized RNA duplexes of 25-30 base length can have as much as a 100-fold increase in potency compared with 21 mers at the same location. At the site most extensively examined in this study, EGFPS1, only minor differences in potency were seen between duplexes with blunt, 3'-overhang or 5'-overhang ends, and a blunt 27 mer duplex was most potent (Kim et al., 2005). Increased potency has similarly been described for 29 mer stem short hairpin RNAs (shRNAs) when compared with 19 mer stem hairpins (Siolas et al., 2005). While the primary function of Dicer is generally thought to be cleavage of long substrate dsRNAs into short siRNA products, Dicer also introduces the cleaved siRNA duplexes into nascent RISC in *Drosophila* (Lee et al., 2004); Pham et al., 2004; Tomari et al., 2004). Dicer is involved in RISC assembly and is itself part of the pre-RISC complex (Sontheimer et al., 2005). The observed increased potency obtained using longer RNAs in triggering RNAi is theorized to result from providing Dicer with a substrate (27 mer) instead of a product (21 mer) and that this improves the rate or efficiency of entry of the siRNA duplex into RISC.

Not all 27 mers show this kind of increased potency. It is well known that shifting a 21 mer siRNA by a few bases along the mRNA sequence can change its potency by 10-fold or more (Holen et al., 2002); Harborth et al., 2003; Reynolds et al., 2004). Different products that result from dicing can have different functional potency, and control of the dicing reaction may be necessary to best utilize Dicer—substrate RNAs in RNAi. The EGFPS1 blunt 27 mer studied in Kim et al. (2005) is diced into two distinct 21 mers. Vermeulen and colleagues reported studies where synthetic 61 mer duplex RNAs were digested using recombinant human Dicer in vitro and examined for cut sites using a $^{32}$P-end-labeled gel assay system. Heterogeneous cleavage patterns were observed and the presence of blunt versus 3'-overhang ends altered precise cleavage sites (Vermeulen et al., 2005). Dicing patterns were studied at a variety of sites using different duplex designs to see if cleavage products could be predicted. It has been found that a wide variety of dicing patterns can result from blunt 27 mer duplexes. An asymmetric duplex having a single 2-base 3'-overhang generally has a more predictable and limited dicing pattern where a major cleavage site is located 21-22 bases from the overhang. Including DNA residues at the 3' end of the blunt side of an asymmetric duplex further limits heterogeneity in dicing patterns and makes it possible to design 27 mer duplexes that result in predictable products after dicing.

It has been found that position of the 3'-overhang influences potency and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript. Novel designs described here that incorporate a combination of asymmetric 3'-overhang with DNA residues in the blunt end offer a reliable approach to design Dicer—substrate RNA duplexes for use in RNAi applications. See also U.S. published application Nos. 2005/0244858 A1 and 2005/0277610 A1, each incorporated herein by reference.

Recently, several groups have demonstrated that siRNAs can be effectively transcribed by Pol III promoters in human cells and elicit target specific mRNA degradation. (Lee et al., 2002; Miyagishi et al., 2002; Paul et al., 2002; Brummelkamp et al., 2002; Ketting et al., 2001). These siRNA encoding genes have been transiently transfected into human cells using plasmid or episomal viral backbones for delivery. Transient siRNA expression can be useful for rapid phenotypic determinations preliminary to making constructs designed to obtain long term siRNA expression. Of particular interest is the fact that not all sites along a given mRNA are equally sensitive to siRNA mediated downregulation. (Elbashir et al., 2001a; Lee et al., 2001; Yu et al., 2002; Holen et al., 2002).

In contrast to post-transcriptional silencing involving degradation of mRNA by short siRNAs, the use of long siRNAs to methylate DNA has been shown to provide an alternate means of gene silencing in plants. (Hamilton et al., 2002). In higher order eukaryotes, DNA is methylated at cytosines located 5' to guanosine in the CpG dinucleotide. This modification has important regulatory effects on gene expression, especially when involving CpG-rich areas known as CpG islands, located in the promoter regions of many genes. While almost all gene-associated islands are protected from methylation on autosomal chromosomes, extensive methylation of CpG islands has been associated with transcriptional inactivation of selected imprinted genes and genes on the inactive X-chromosomes of females. Aberrant methylation of normally unmethylated CpG islands has been documented as a relatively frequent event in immortalized and transformed cells and has been associated with transcriptional inactivation of defined tumor suppressor genes in human cancers. In this last situation, promoter region hypermethylation stands as an alternative to coding region mutations in eliminating tumor suppression gene function. (Herman et al., 1996).

U.S. published application No. 2004/0096843 A1, incorporated herein by reference, is directed to methods for producing double-stranded, interfering RNA molecules in mammalian cells. These methods overcome prior limitations to the use of siRNA as a therapeutic agent in vertebrate cells, including the need for short, highly defined RNAs to be delivered to target cells other than through the use of synthetic, duplexed RNAs delivered exogenously to cells. U.S. published application No. 2004/0091918 A1, incorporated herein by reference, is directed to methods and kits for synthesis of siRNA expression kits.

Small interfering RNA (siRNA) mediated transcriptional gene silencing (TGS) was first observed in doubly transformed tobacco plants which exhibited a suppressed phenotype of the transformed transgene. Careful analysis indicated that methylation of the targeted gene was involved in the suppression (Matzke et al., 1989). TGS mediated by dsRNAs was further substantiated in plants infected with a cytoplasmic dsRNA virus; nuclear transgenes with promoters homologous to sequences in the virus were found to be silenced (Wassenegger et al., 1994; Wassenegger, 2000). siRNAs that target promoter sequences have also been shown to cause TGS in the yeast *S. pombe* and in *Drosophila* (Pal-Bhadra et al., 2002; Schramke and Allshire, 2003). Transcriptional silencing by siRNA most likely functions as a genome defense mechanisms that target chromatin modifications to endogenous silent loci such as transposons and repeated sequences (Seitz et al., 2003; Soifer et al., 2005). In plants and yeast siRNA-induced silencing is accompanied by DNA methylation of homologous sequences, de novo DNA methylation in *Arabidopsis thaliana* requires siRNA metabolizing factors, and maintenance of *S. pombe* centromeric heterochromatin depends on siRNA-directed histone H3 lysine 9 methylation (Chan et al., 2004; Jones et al., 2001; Mette et al., 2000; Volpe et al., 2002; Zilberman et al., 2003).

While dsRNAs induce sequence-specific methylation of DNA in plants and yeast, regulating gene expression at the transcriptional level, it was not known until recently how applicable this phenomenon was in mammalian cells. Recent reports have documented that siRNAs targeted to 2 different genes, specifically the promoter regions, can induce transcriptional silencing via histone and DNA methylation in human cells (Morris et al., 2004b; Kawasaki and Taira, 2004; Kawasaki et al., 2005). While these reports were intriguing many questions regarding the underlying mechanism remained.

It is desired to utilize this activity and to use siRNAs to induce transcriptional gene silencing in cells.

SUMMARY OF THE INVENTION

The present invention relates to transcriptional gene silencing (TGS) in mammalian, including human, cells that is mediated by small interfering RNA (siRNA) molecules. The present invention also relates to a method for directing histone and/or DNA methylation in mammalian, including human, cells. The present invention also relates to a double stranded nucleic acid that directs methylation of histones associated with target genes that produce low copy promoter-specific RNA.

In one aspect of the invention, it has been found that siRNAs can be used to direct methylation of histones and/or DNA in mammalian, including human, cells.

In a second aspect of the invention, it has been found that the antisense strand from siRNA directed against a promoter sequence binds DNMT3A to induce histone H3 lysine-27 methylation and transcriptional gene silencing in an RNA polymerase II dependant manner.

In a third aspect of the invention, it has been found that Argonaute 1 (Ago1) is required for siRNA mediated histone H3 lysine-9 di-methylation ($H3K9^{me2+}$). It has also been found that Ago1 associates with RNA polymerase II (RNAPII), and that Ago1 and RNAPII co-localize to epigenetically silenced genomic loci, suggesting the involvement of an RNA component that is recognized by Ago1. Furthermore, the HIV-1 TAR RNA-binding protein 2 (TRBP2) is enriched at silenced promoters, along with histone H3 lysine-27 tri-methylation ($H3K27^{me3+}$), a histone methyl-mark that recruits the Polycomb group (PcG) repressor proteins. Thus, it has been found that Ago1 is involved in the initiation and spreading of siRNA mediated TGS, as well as transcriptional silencing at facultative heterochromatin, linking the RNAi machinery with RNAPII transcription and histone regulated control of gene expression.

In accordance with these findings, the present invention provides a method of reducing gene expression of a target gene using an siRNA molecule. In one embodiment, the siRNA molecule increases methylation of histones associated with the target gene. In a second embodiment, the siRNA molecule is directed to the promoter region of the gene. In a third embodiment, the siRNA molecule binds to a sequence within about 150 bp of the transcription start site.

In one aspect, the present invention provides a method for TGS in a mammalian, including human, cell comprising exposing or introducing into the cell a siRNA which is specific for a target sequence in the promoter region of a gene to be silenced.

In another aspect, the present invention provides a method for TGS in a mammalian, including human, cell comprising introducing into the cell DNA sequences encoding a sense strand and an antisense strand of an siRNA which is specific for a target sequence in the promoter region of a gene to be silenced, preferably under conditions permitting expression of the siRNA in the cell, and wherein the siRNA induces histone modifications characteristic of silent chromatin and/or methylation of the gene.

In a further aspect, the present invention provides a method for TGS in a mammalian, including human, cell comprising introducing into the cell an siRNA molecule which is specific for a target sequence in the promoter region of a gene to be silenced and which interacts with Ago1 to direct transcriptional silencing of the gene of interest.

In a still further aspect, the present invention provides siRNA molecules, each comprising a sense strand and an antisense strand, wherein the antisense strand has a sequence sufficiently complementary to a promoter region of a gene of interest to direct TGS of the gene of interest.

In another aspect, the present invention provides pharmaceutical compositions containing the disclosed siRNA molecules.

BRIEF DESCRIPTION OF THE FIGURES

FIG. 1A: The 3' PCR primer is complementary to sequences at the 3' end of the U6 promoter and is followed by the sense or antisense sequences, a stretch of four to six deoxyadenosines (Ter) and an additional stuffer-Tag sequence. The adenosines are the termination signal for the U6 Pol III promoter; therefore, any sequence added after this signal will not be transcribed by the Pol III polymerase and will not be part of the siRNA. FIG. 1B: The sense and antisense sequences are linked by a 9 nt loop and are inserted in the cassette by a two-step PCR reaction. FIG. 1C: The sense and antisense sequences linked by a 9-nucleotide loop and followed by the stretch of adenosines and by the Tag sequences are included in a single 3' primer. FIG. 1D: Complete PCR expression cassette obtained by the PCR reaction. To amplify and identify functional siRNAs from the transfected cells, or to increase the yield of the PCR product shown in D, a nested PCR can be performed using the universal 5' U6 primer and a 3' primer complementary to the Tag sequence, as indicated in the figure.

Figure 3:
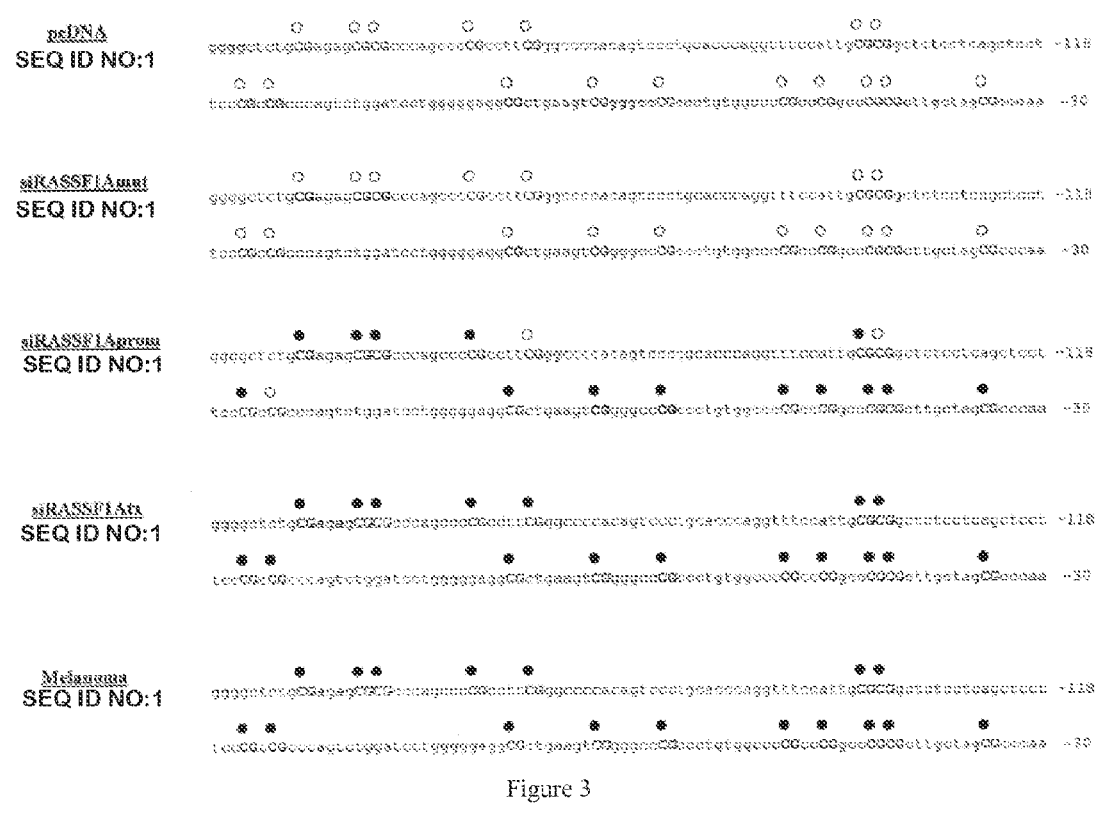

FIG. 3 illustrates DNA sequences (each sequence is SEQ ID NO:1) of the RASSF1A promoter that became methylated in siRNA transfected cells.

FIG. 7A: MPG transfected EF52 siRNA induces histone methylation. Histone 3 Lysine 9 (H3K9) di-methylation and histone 3 Lysine 27 (H3K27) tri-methylation was determined from 293T cells transfected with EF52 or the control CCR5 siRNAs (10 nM) using the nuclear specific amphipathic peptide MPG (Morris et al., 1997). Forty-eight hours post-transfection ChiP assays were performed specifically for the EF1a promoter (Morris et al., 2004b). Results represent 2 independent experiments with standard deviations shown. FIG. 7B: Nuclear specific delivery is required for Histone methylation. MPG and Lipofectamine transfection reagents were used to transfect EF52-Cy3+ siRNAs into 293T cells. Forty eight hours following transfection cultures were collected and a ChiP assay run. Results of a single experiment are shown.

FIG. 8A: Detection of flag-tagged DNMTs or HP1s bound to siRNA EF52. Schematic methodology is shown for detecting biotin labeled siRNA which are bound by flag-tagged DNMTs. FIG. 8B: Co-immunoprecipitation ChiP/siRNA assay. Methodology for performing a H3K9 or H3K27 ChiP followed by a biotin/avidin pulldown for detecting siRNA EF52 associated with histone methyl marks (H3K9 or H3K27). FIG. 8C: Triple immunoprecipitation assay. Methodology is shown for performing first a ChiP for H3K27 followed by a flag-immunoprecipitation followed by a biotin/avidin pulldown for biotin labeled siRNA. The resultant elutes were utilized in PCR for the targeted EF1A promoter.

FIG. 9A Biotin labeled EF52 siRNAs pulldown DNMT3A. Whole cell lysates from transfected 293T cells expressed detectable amounts of all flag-tagged expressed DNMT proteins (Table 1) with the exception of DNMT 3B1. FIG. 9B: Recombinant HP1 alpha and beta were also expressed at appreciable levels in whole cell lysates while HP1-gamma exhibiting a reduced expression. FIG. 9C: Following siRNA EF52-Biotin incubation with whole cell extracts (A&B) and subsequent pull-down (FIG. 8A) only DNMT 3A, 3A2 and 3B2 were detectable while the control Mock, Prp2, and DNMT-1 (MT-1) were not co-immunoprecipitated with the EF52 siRNA. FIG. 9D: Flag-tagged DNMT1 and DNMT3A transfected 293T lysates (whole cell extracts, refer to FIG. 8A) were generated and incubated with a total of 500 nM siRNA biotin labeled Sense (S), antisense (AS), or both sense and antisense (S/AS), and the control sense and antisense without a biotin label (−). FIG. 9E: Antisense and the Sense/Antisense siRNA EF52 binds DNMT3A but not DNMT1.

FIG. 11A: Detection of antisense siRNA/H3K27 and targeted EF1A promoter as one complex. Biotin labeled antisense siRNA EF52 co-precipitates (~4.8 fold greater concentration relative to no antibody control) with tri-methylated H3K27 in a ChiP/RNA co-immunoprecipitation. FIG. 11B: Biotin labeled antisense siRNA EF52 co-precipitates with H3K27, flag-tagged DNMT3A and the targeted EF1A promoter. FIG. 11C: HIV-1 U3 specific antisense siRNAs LTR-247 and LTR-362 suppress Tat induced luciferase expression in TZM-B1 cells. Results from a single experiment are shown. FIG. 11D: Antisense siRNAs targeting the U3 region of the HIV-1 LTR inhibit Tat mediated activation of fire fly luciferase in 1G5 cells. Results are from two independent experiments and standard deviations are shown. FIG. 11E: Treatment of 293T cells with alpha amanatin (0.05 μg/ml) 24 hrs following transfection with siRNA EF52 reduces H3K9 methylation ~60% relative to no antibody control to levels comparable to CCR5 siRNA transfected cultures (not shown). Results from one experiment are shown.

Figure 12:
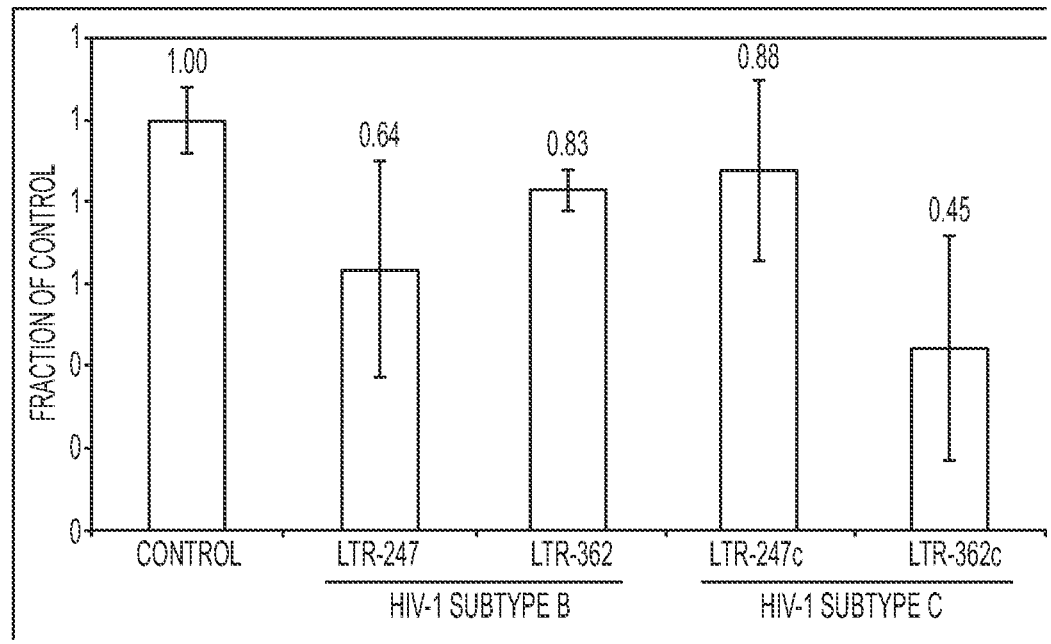

FIG. 12 shows LTR specific siRNAs induce silencing of Tat mediated expression of fire fly luciferase. HIV-1 U3 LTR specific siRNAs (Table 2) targeting either subtype B or subtype c were co-transfected with pCMV-Tat expression plasmid into TZM-B1 (Wei et al., 2002) cells and luciferase expression determined 48 hrs later. Results from two independent experiments are shown with standard deviations.

Figure 13:
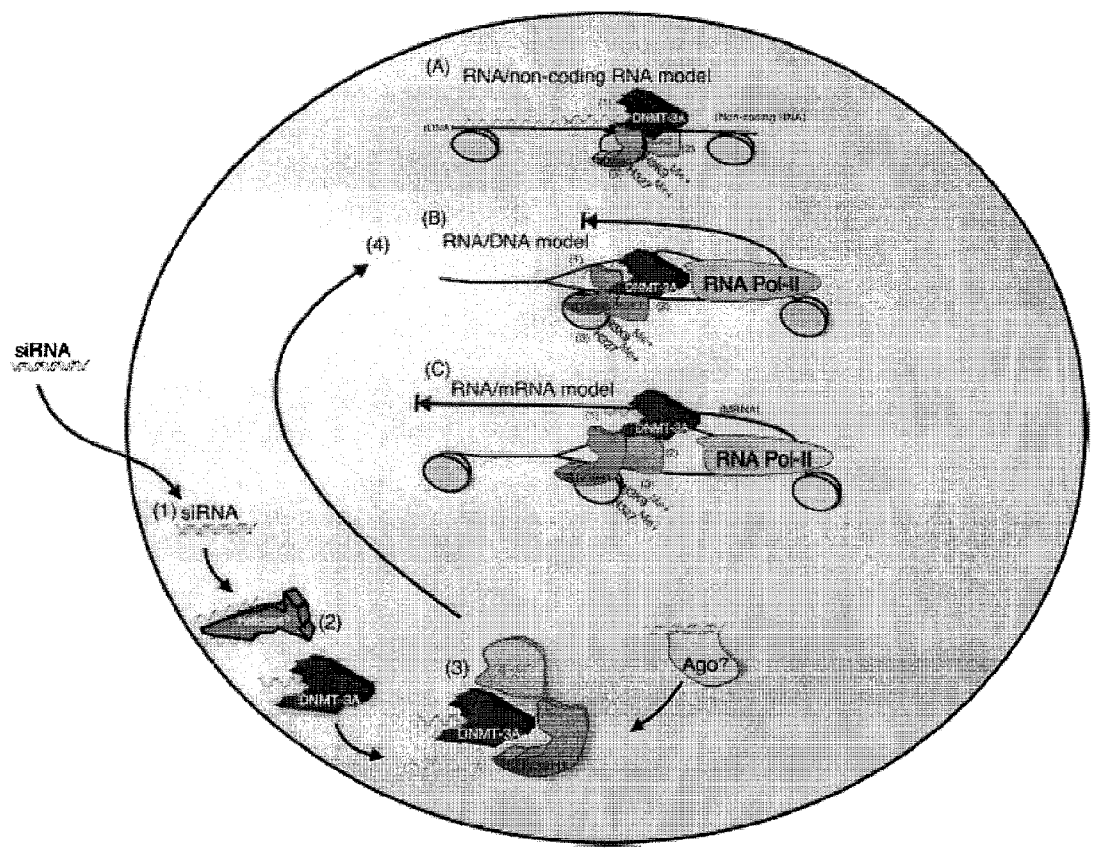

FIG. 13 shows a model for siRNA mediated TGS in human cells on the basis of the results up to this figure. SiRNAs are introduced by nuclear specific MPG based transfection (Morris et al., 2004b) into the target cells (1). Once inside the nucleus the antisense strand of the siRNA (AS-siRNA) is bound by DNMT3A (data not shown) (2). (DNMT3b may also bind siRNA) (Jeffery and Nakielny, 2004; K.V. data not shown). Next the AS-siRNA/DNMT3a complex may interact directly or already be bound by HDACs and/or Suv39H1 (Fuks et al., 2003; Fuks et al. 2001) (3). The AS-siRNA probably then directs either the AS-siRNA/DNMT3A complex with or without the HDACs and/or Suv39H1 to the targeted promoter region, possibly via an interaction with a non-coding transcript that is associated with the targeted chromatin (4) where HDAC can deacetylate the respective histones (H3K9 and/or H3K27). The deacetylation of H3K9 and H3K27 would then permit histone methyltransferases such as Suv39H1 to methylate H3K9 and possibly H3K27 resulting in initial silencing of transcription (5). If the silencing is re-enforced the gene may become methylated and permanently silenced.

Figure 14:
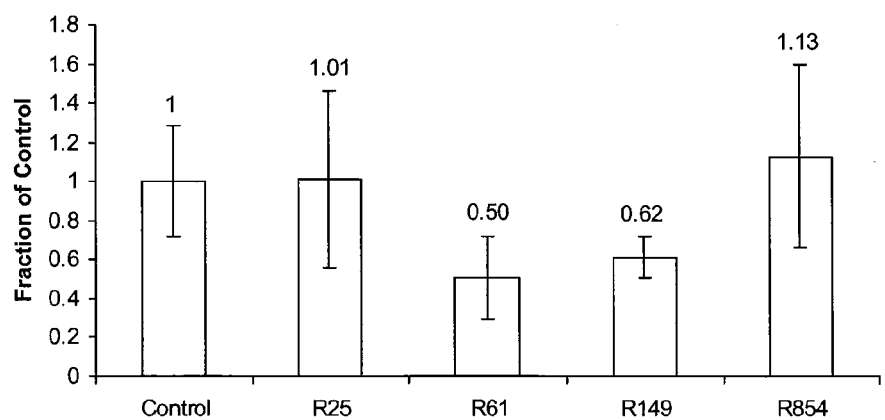

FIG. 14 shows CCR5 promoter-targeted knockdown of GFP expression. Suppression of CCR5 expressed GFP by promoter-specific siRNAs at 48 hrs post-transfection. Error bars represent standard deviations from n=3 independent experiments.

Figure 15A:
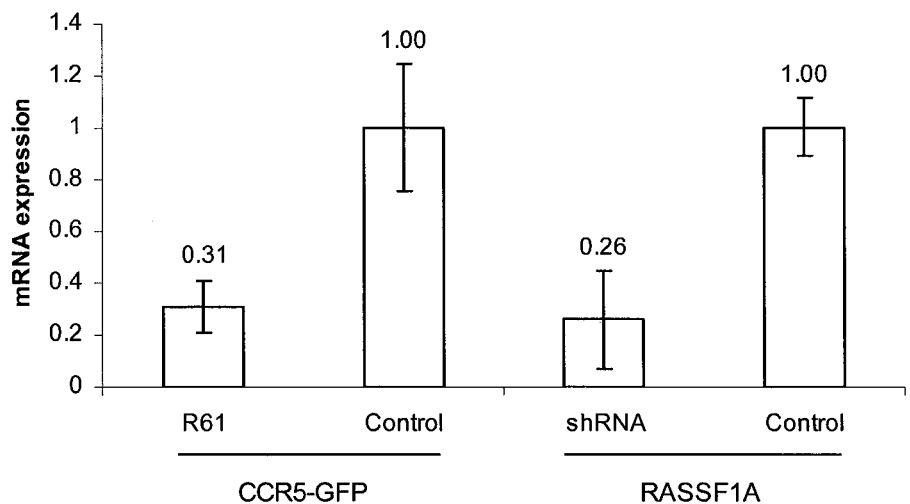
Figure 15B:
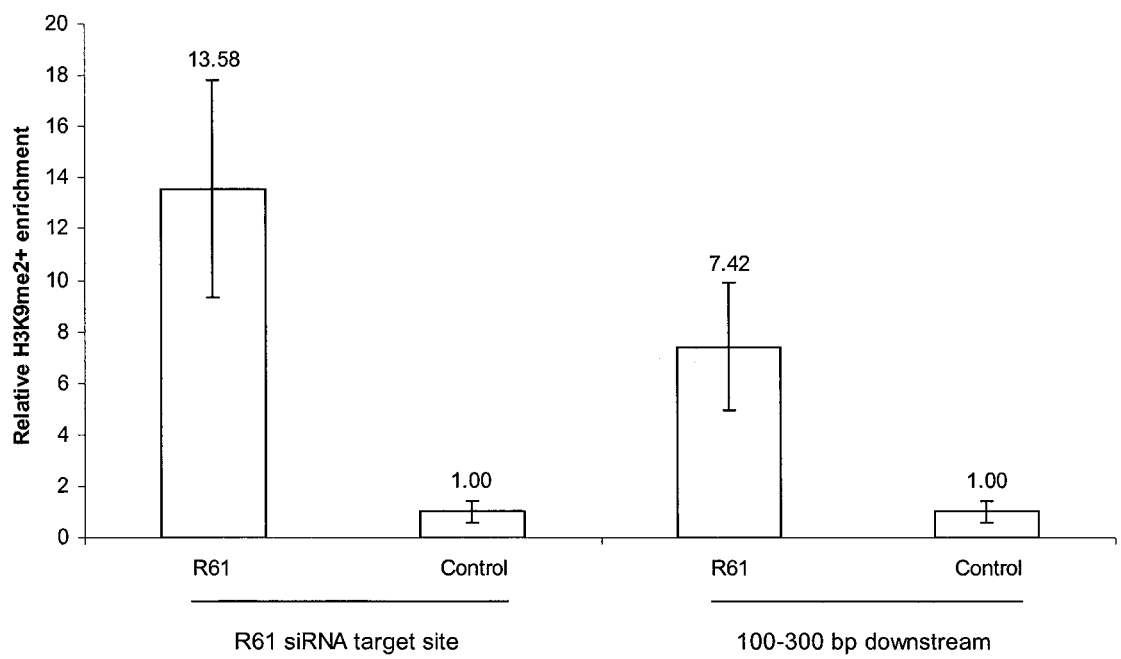
Figure 15C:
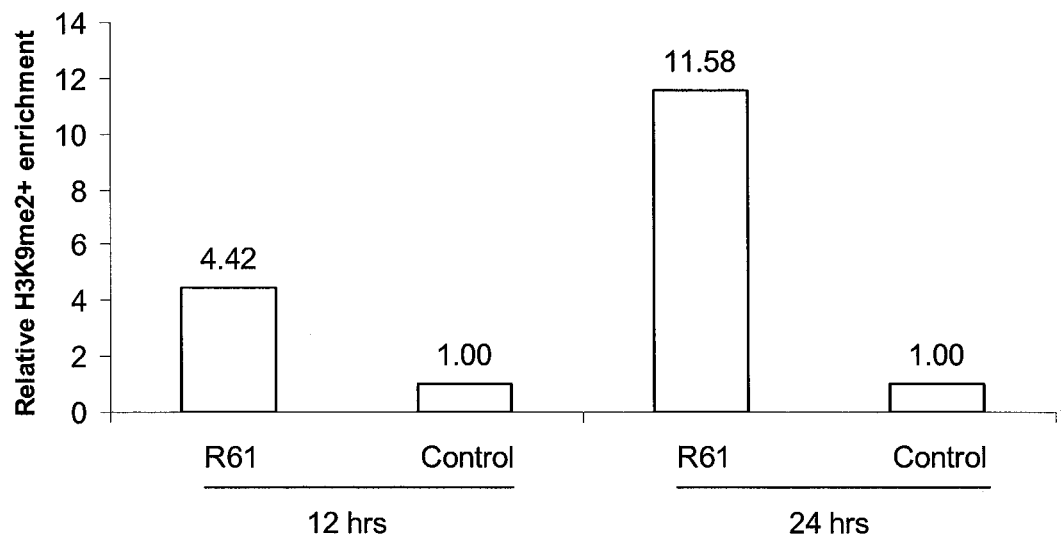

FIGS. 15A-15C show that synthetic siRNAs and expressed shRNAs mediate transcriptional gene silencing of the CCR5 and RASSF1A promoters. FIG. 15A: GFP mRNA expression in R61 (promoter-specific) or R5 (CCR5 mRNA-specific) control siRNA-treated 293T CCR5-GFP cells, and RASSF1A mRNA expression in HeLa cells stably expressing an shRNA (RASSF1A promoter-specific) or control vector alone, as determined by real-time quantitative RT-PCR (qRT-PCR) and normalized to GAPDH levels (at 24 hrs post-siRNA transfection for GFP samples). Error bars represent standard error of the mean (s.e.m.) for n=4 (GFP) and n=3 (RASSF1A) independent samples, respectively. FIG. 15B: Chromatin immunoprecipitation (ChIP) of the CCR5 promoter (at the R61 siRNA target site or 100-300 by downstream) using anti-H3K9$^{me2+}$ antibody in extracts from R61 or R5 control siRNA-treated cells at 24 hrs post-siRNA transfection. Error bars represent s.e.m. for n=3 independent experiments. FIG. 15C: Time-course ChIP of the CCR5 promoter using anti-H3K9$^{me2+}$ antibody in extracts from R61 or R5 control siRNA-treated cells at 12 and 24 hrs post-siRNA transfection.

Figure 16:
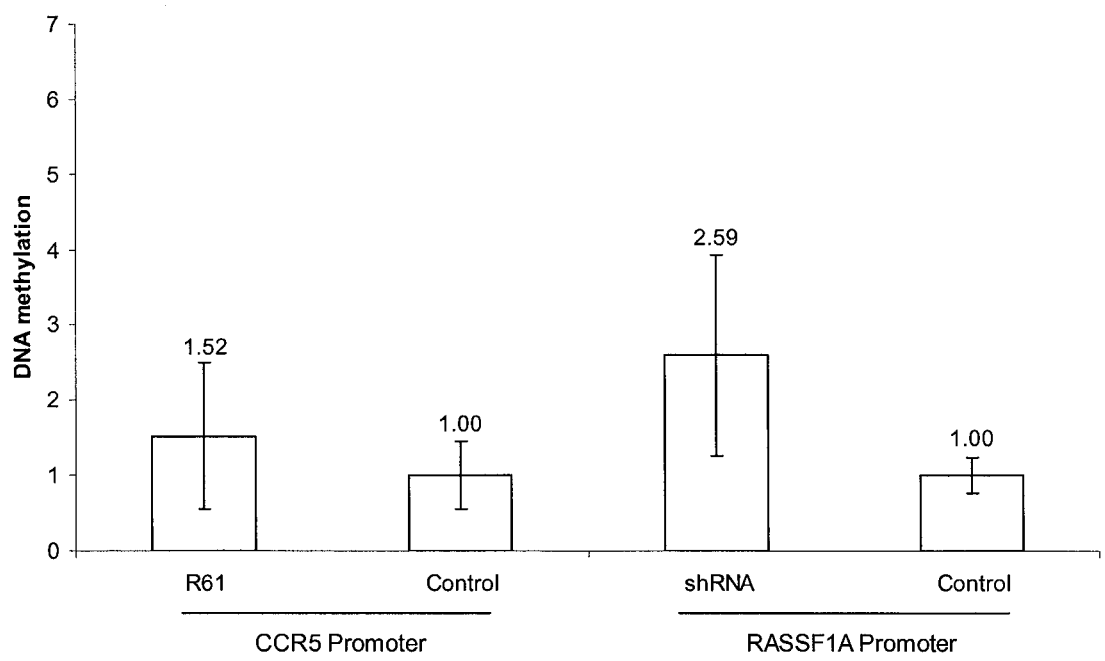

FIG. 16 shows low levels of DNA methylation at targeted promoters. DNA methylation at the R61 or R5 control siRNA-targeted CCR5 promoter in 293T CCR5-GFP cells, and DNA methylation at the endogenous RASSF1A promoter in HeLa stable cells expressing promoter-specific shRNA or control vector, using an AvaI or ApaI-based DNA methylation assay of the CCR5 and RASSF1A promoters, respectively. Error bars represent standard error of the mean (s.e.m.) for n=3 independent samples.

Figure 17A:
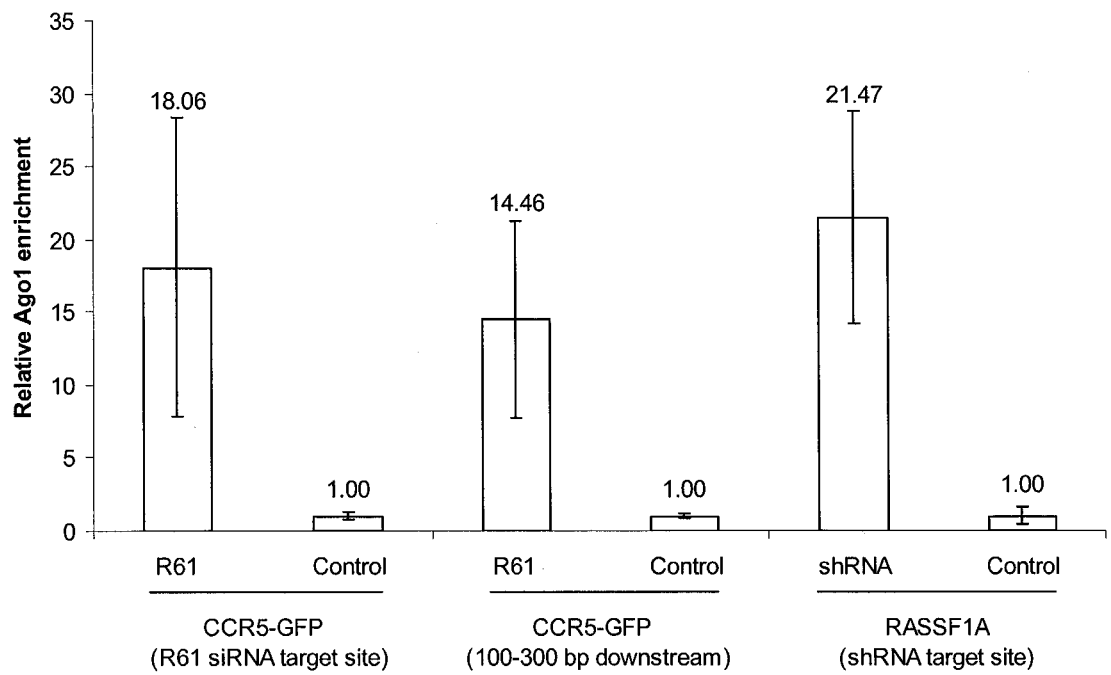
Figure 17B:
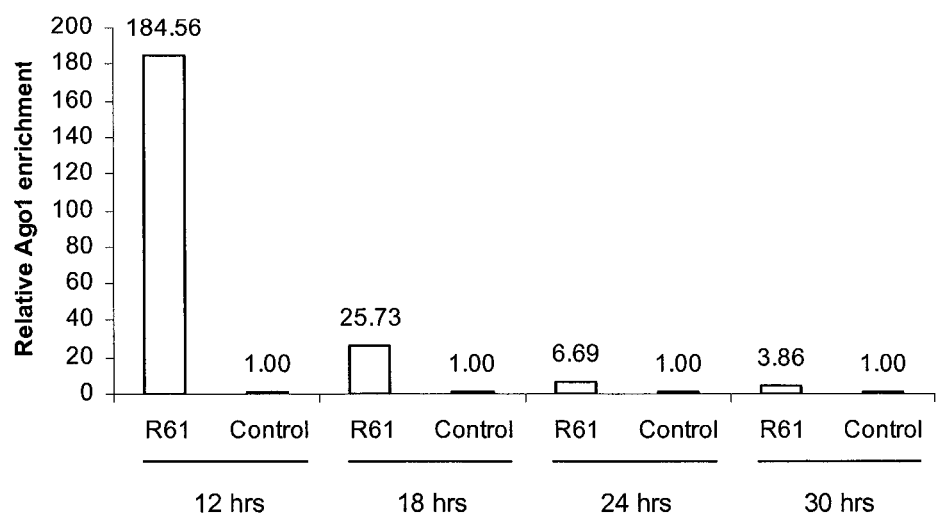
Figure 17C:
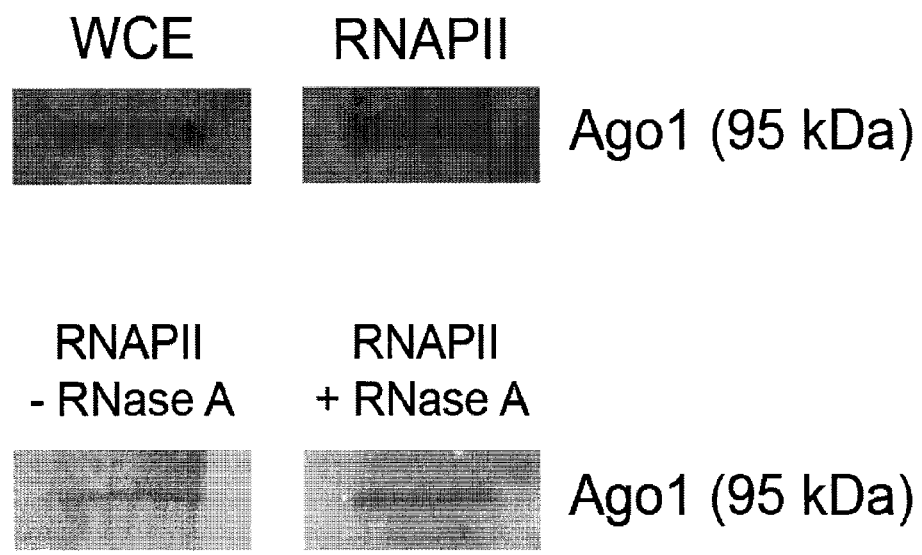

FIGS. 17A-17C show that Argonaute 1 protein associates with the targeted CCR5 and RASSF1A promoters and RNA polymerase II. FIG. 17A: ChIP of the CCR5 promoter (at the R61 siRNA target site or 100-300 by downstream) in extracts from 293T CCR5-GFP cells transfected with R61 or R5 control siRNAs at 18 hrs post-siRNA transfection, and ChIP of the endogenous RASSF1A promoter in extracts from promoter shRNA-expressing or control vector-expressing HeLa stable cells, using anti-Ago1 antibody. Error bars represent s.e.m. for n=3 independent experiments. FIG. 17B: Time-course ChIP of the CCR5 promoter performed at 6 hr intervals post-R61 or R5 control siRNA transfection. FIG. 17C: Whole cell extracts (WCE) from 293T CCR5-GFP cells and anti-RNAPII immunoprecipitates from RNase A untreated (− RNase A) or treated (+ RNase A) extracts, analyzed by western blot using anti-Ago1 antibody.

Figure 18A:
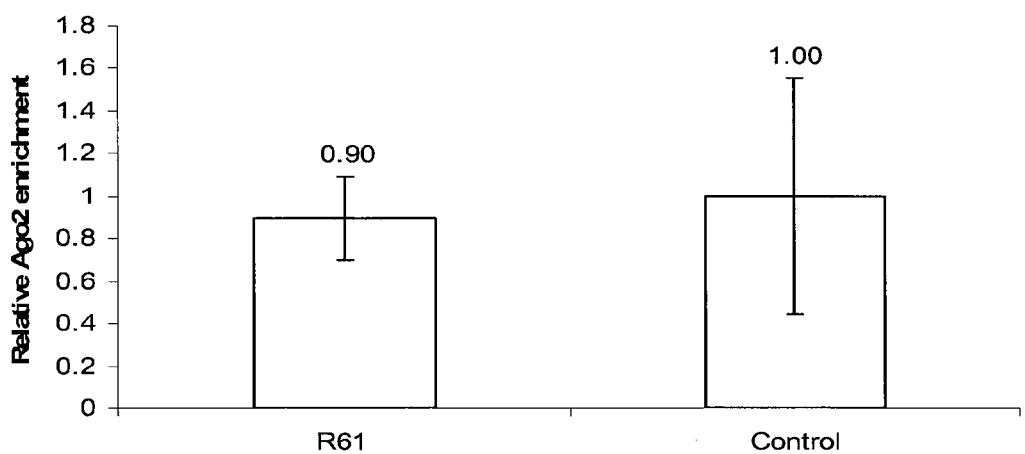
Figure 18B:
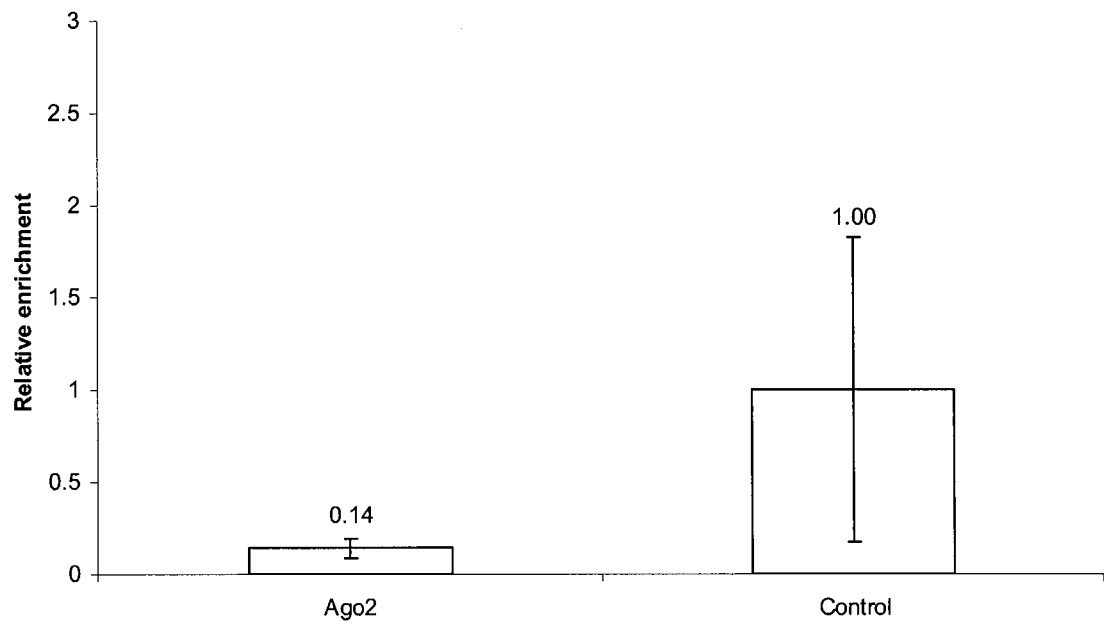

FIGS. 18A-18B Argonaute 2 does not associate with the siRNA targeted CCR5 promoter. ChIP was performed using anti-Ago2 antibody on the CCR5-GFP promoter in 293T CCR5-GFP cells transfected with either R61 or R5 control siRNAs at 18 hrs post-siRNA transfection (FIG. 18A) or on the endogenously silenced CCR5 promoter in HEK 293 cells using anti-Ago2 antibody or no antibody controls (FIG. 18B). Error bars represent s.e.m. for n=3 independent experiments.

Figure 19A:
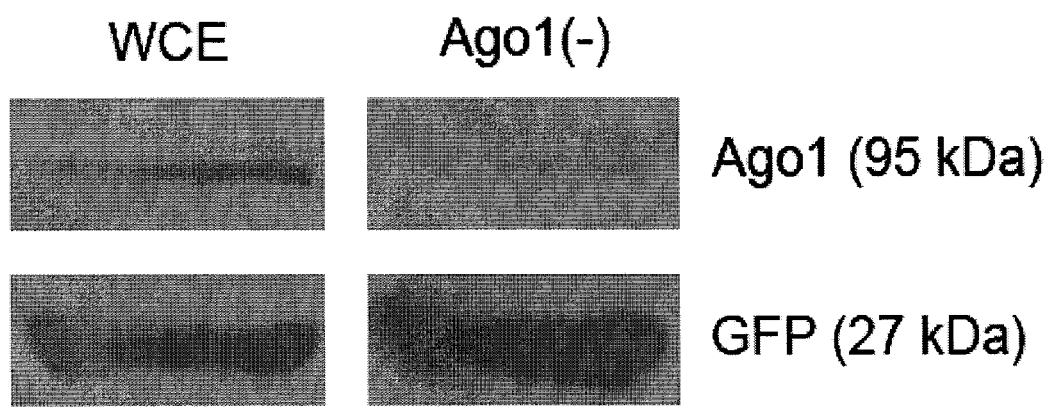
Figure 19B:
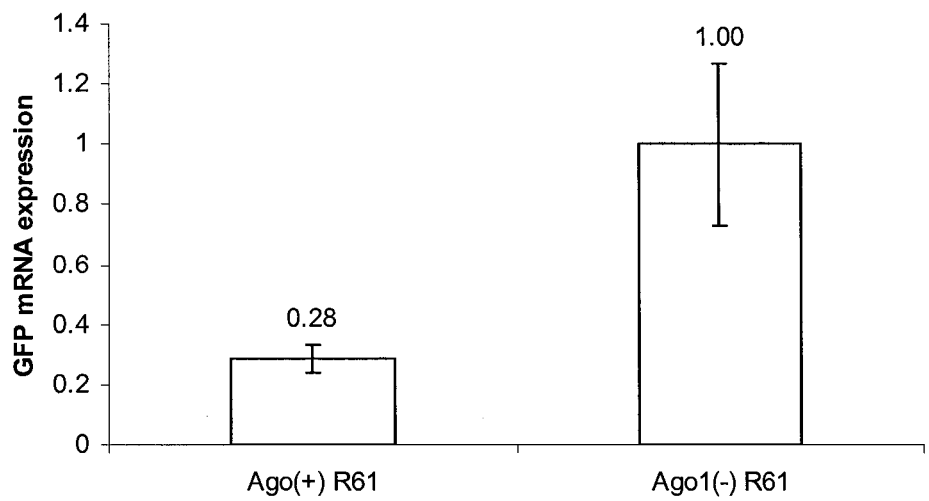
Figure 19C:
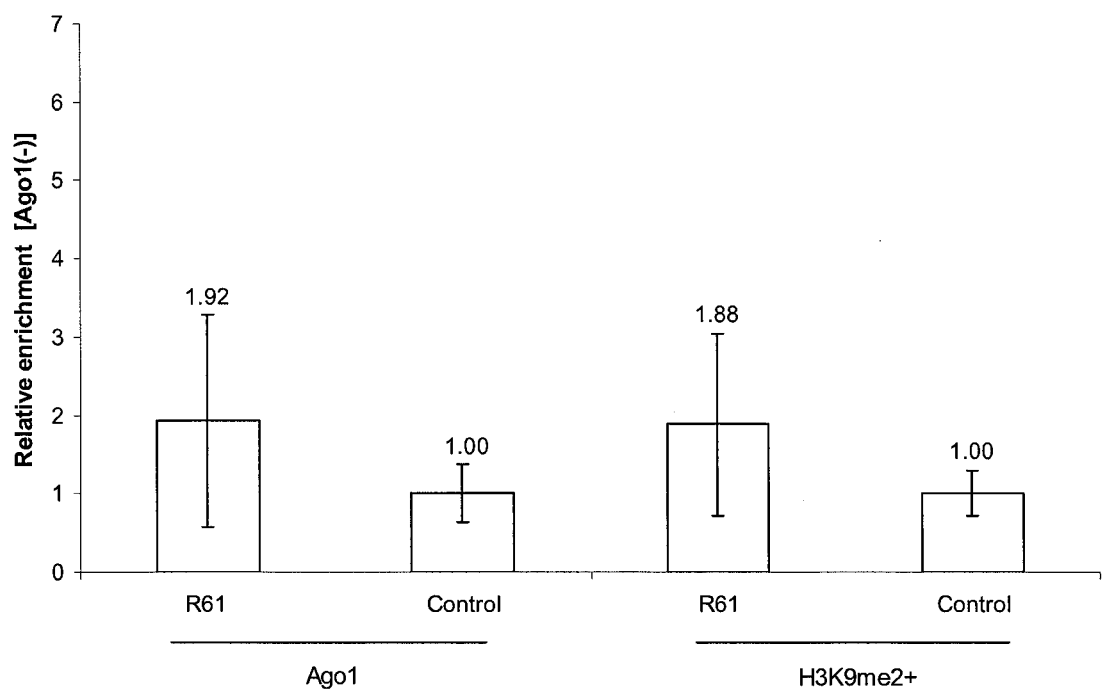

FIGS. 19A-19C show that Argonaute 1 is required for histone methylation and transcriptional silencing. FIG. 19A: Whole cell extracts (WCE) and extracts from 293T CCR5-GFP cells treated with Ago1 mRNA-specific siRNA [Ago1(−)] at 48 hrs post-Ago1 siRNA transfection and analyzed by western blotting using anti-Ago1 antibody. GFP was included as a loading control. FIG. 19B: 293T CCR5-GFP cells transfected with R61 siRNA at 24 hrs post-R5 control siRNA [Ago1(+)] or Ago1 siRNA [Ago1(−)] transfection, as determined by qRT-PCR and normalized to GAPDH levels at 24 hrs post-R61 siRNA transfection. Error bars represent s.e.m. for n=3 independent samples. FIG. 19C: ChIP of the CCR5 promoter using anti-Ago1 or anti-H3K9$^{me2+}$ antibody in R61 or R5 control siRNA-treated Ago1(−) 293T CCR5-GFP cells at 24 hrs post-R61 or R5 control siRNA transfection and 48 hrs post-Ago1 siRNA transfection. Error bars represent s.e.m. for n=3 independent experiments.

Figure 20A:
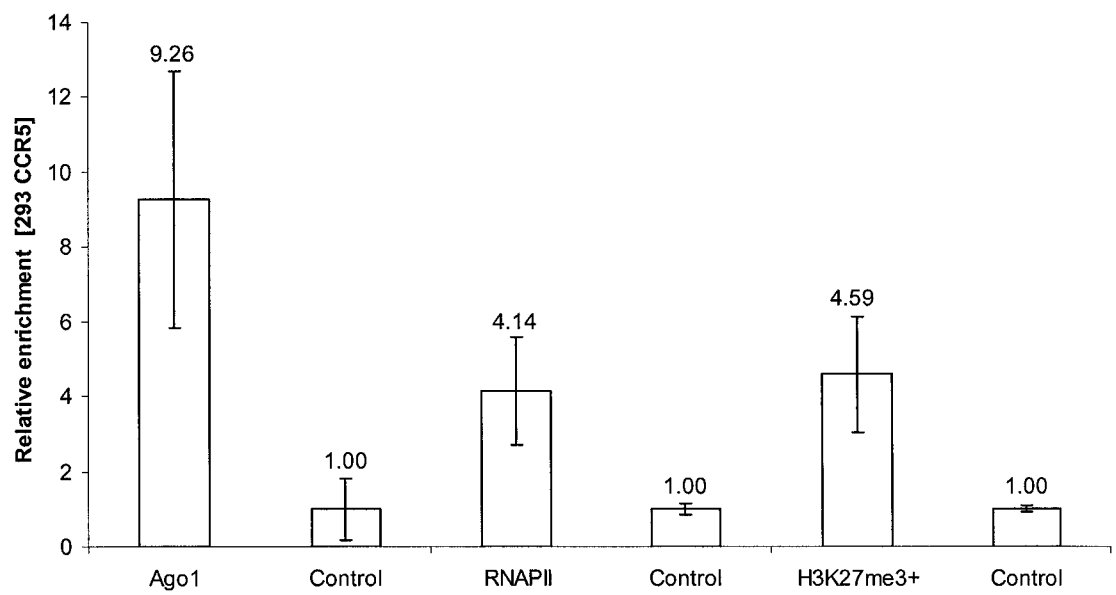
Figure 20B:
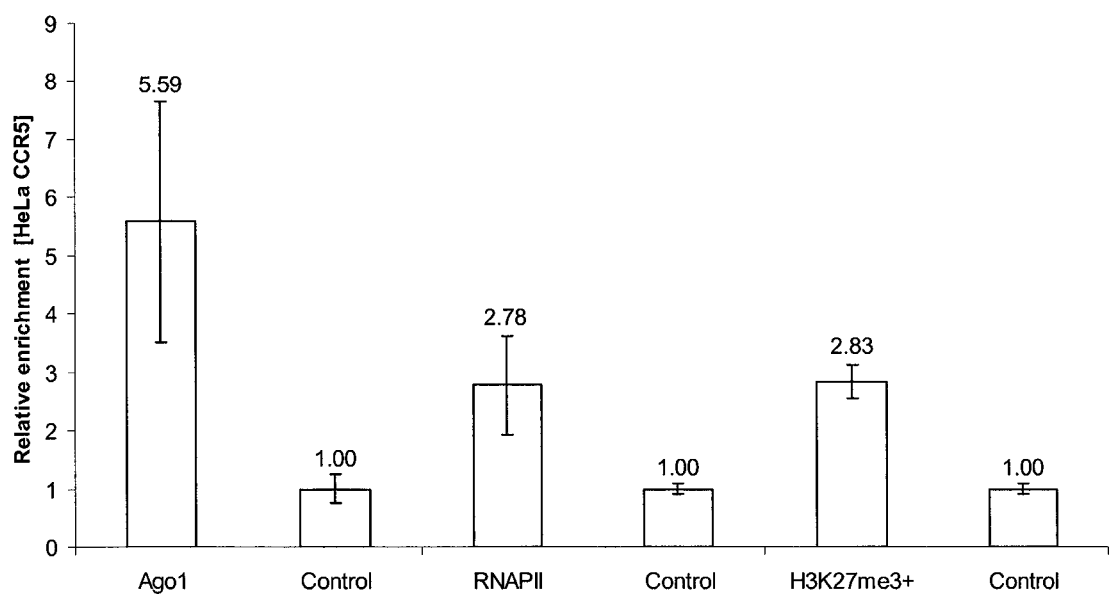
Figure 20C:
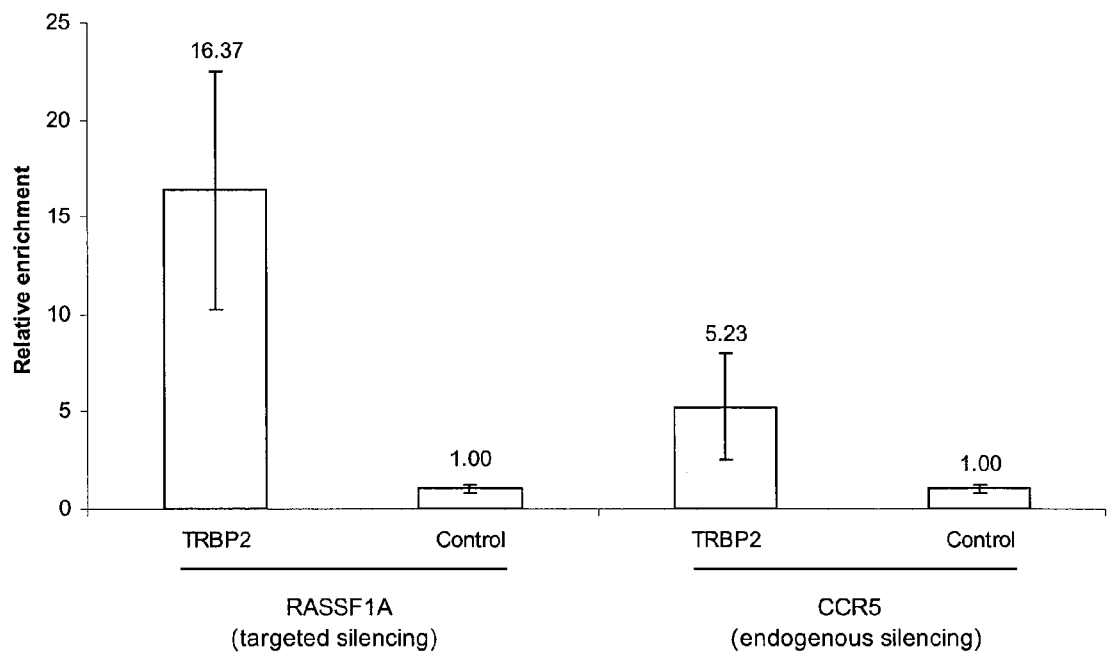

FIGS. 20A-20C show that Argonaute 1, RNA polymerase II, H3K27$^{me3+}$, and TRBP are enriched at the endogenously silenced CCR5 promoter. ChIP of the endogenous CCR5 promoter in untreated HEK 293 (FIG. 20A) and HeLa (FIG. 20B) cell extracts, using anti-Ago1, anti-RNAPII, and anti-H3K27$^{me3+}$ antibodies or no antibody controls and normalized to input values. Error bars represent s.e.m. for n=3 independent experiments. FIG. 20C: ChIP of the endogenous RASSF1A promoter in extracts from promoter shRNA-expressing or control vector-expressing HeLa stable cells, and ChIP of the endogenous CCR5 promoter in HeLa cell extracts, using anti-TRBP antiserum. Error bars represent s.e.m. for n=3 independent experiments.

Figure 21:
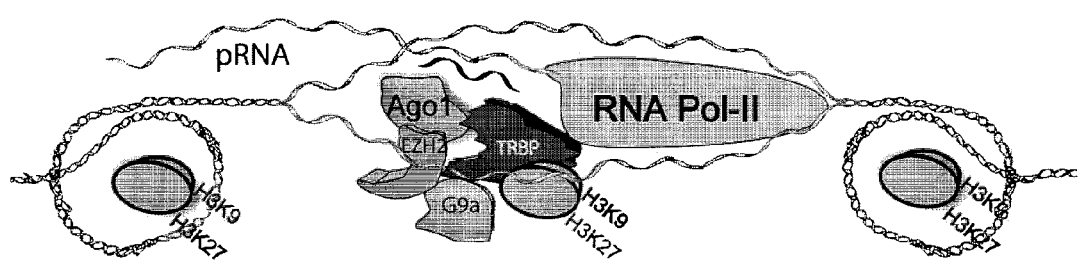

FIG. 21 shows a model for the mechanism of Ago1 directed TGS. The transcriptional silencing complex (TSC) may contain Ago1, TRBP, siRNA, and histone methyltransferases EZH2 (H3K27$^{me3+}$) and G9a (H3K9$^{me2+}$). The tri-methlation of H3K27 would subsequently allow for the Polycomb group repressor complexes to bind to H3K27$^{me3+}$ and recruit DNMT3a, locking in an epigenetically silent state. DNMT3a has also been shown to co-immunoprecipitate with both the antisense strand of the siRNA and the H3K27$^{me3+}$ methylmark (Weinberg et al., 2006).

Figure 22:
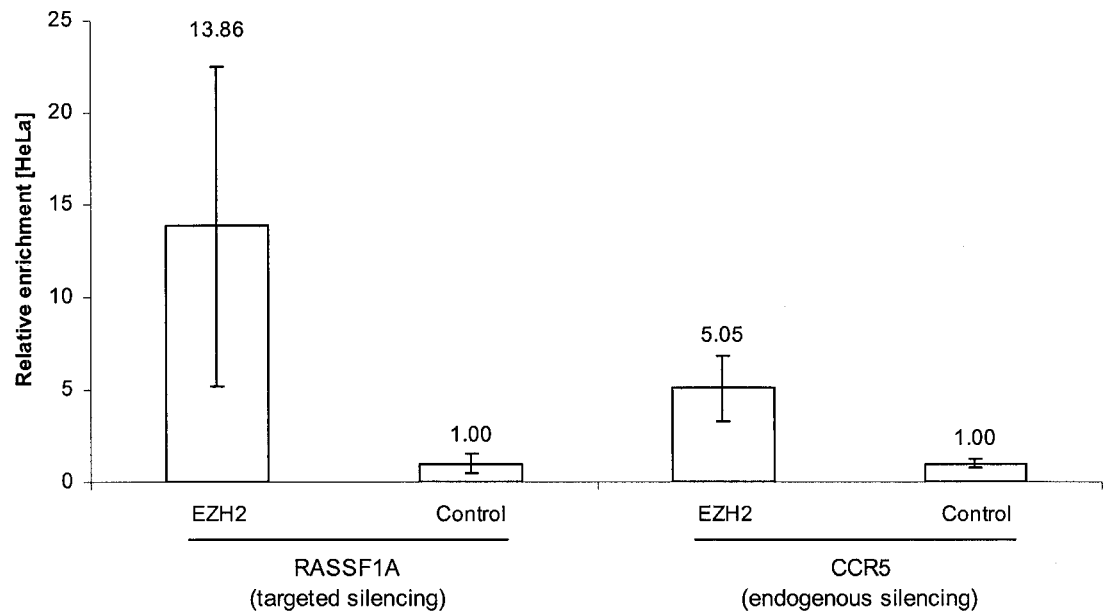

FIG. 22 shows that Polycomb group protein EZH2 is enriched at the RASSF1A and CCR5 promoters. ChIP of the endogenously expressed RASSF1A promoter in extracts from promoter shRNA-expressing or control vector-expressing HeLa stable cells, and ChIP of the endogenously silenced CCR5 promoter in HeLa cell extracts, using anti-EZH2 antibody. Error bars represent s.e.m. for n=3 independent experiments.

Figure 23:
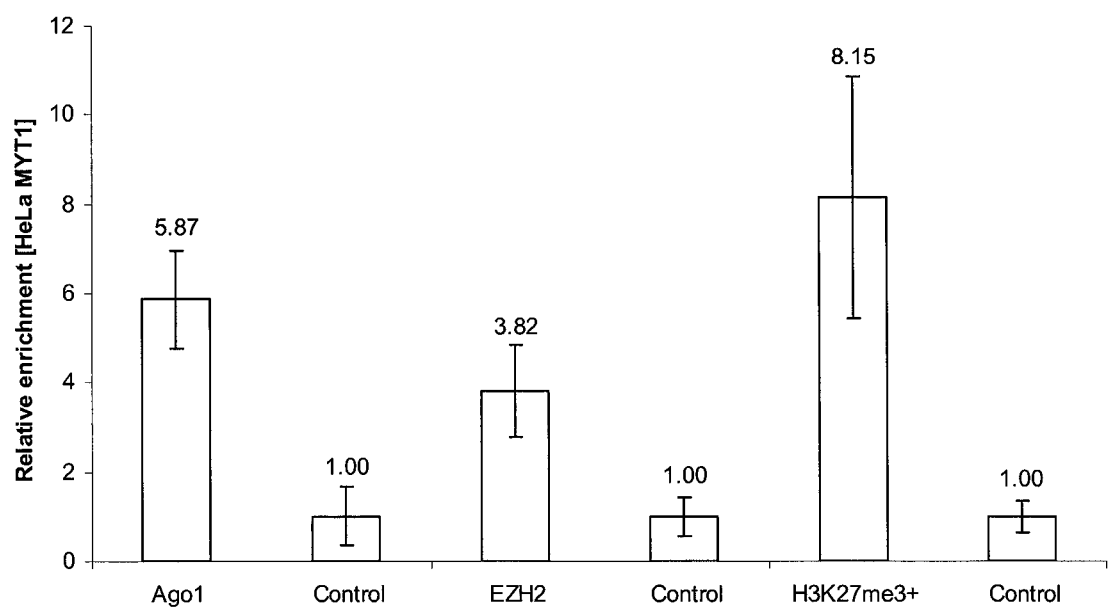

FIG. 23 shows that Argonaute 1 is enriched at the Polycomb group target MYT1 promoter. ChIP of the endogenous Polycomb group target MYT1 promoter in untreated HeLa extracts, using anti-Ago1, anti-EZH2, and anti-H3K27$^{me3+}$ antibodies or no antibody controls and normalized to input values. Error bars represent s.e.m. for n=3 independent experiments.

DETAILED DESCRIPTION OF THE INVENTION

The present invention relates to transcriptional gene silencing (TGS) in mammalian, including human, cells that is mediated by small interfering RNA (siRNA) molecules. The present invention also relates to a method for directing histone and/or DNA methylation in mammalian, including human, cells.

Small interfering RNAs (siRNAs) silence genes at the transcriptional and post-transcriptional level in human cells. As shown herein siRNAs are able to direct transcription gene silencing via a number of mechanisms including, but not limited to, the methylation of human genes and/or associated histones in both the promoter and coding regions of the gene. In addition, although siRNA mediated transcriptional gene silencing (TGS) was recently reported (Morris et al., 2004b) the mechanism remained relatively unknown. As shown herein, we have expanded on this initial observation to address the mechanism of siRNA mediated TGS by screening the binding potential of DNA methyltransferases (DNMT) 1, 3A, 3A2, 3B1, 3B2, and heterochromatin proteins (HP1-alpha, beta, and gamma) to the promoter targeted EF52 siRNAs. Interestingly, DNMT3A, 3A2, 3B1 and 3B2 bound EF52 with DNMT3A displaying the most robust binding. DNMT3A co-immunoprecipitated with the antisense strand of the EF52 siRNA, the targeted EF1 alpha promoter, and the corresponding silent state histone methyl mark. Moreover, the induction of a silent state histone methylation mark by the EF52 siRNA was contingent on RNA polymerase II (Pol-II). The functionality of the antisense strand to induce TGS was also confirmed by targeting the U3 region of the promoter/LTR of HIV-1. These data implicate a functional link between siRNA mediated targeting of genomic regions (including promoters), DNA methylation and DNA methyltransferases (DNMTs), and chromatin remodeling complexes (Suv39H1 and HDACs) in human cells. Moreover, the observations suggest that the antisense strand can induce TGS, this interaction is via an antisense/DNA interaction and requires Pol-II to putatively open up the targeted promoter and as such presents a completely new methodology to transcriptionally silence Pol-II promoter expressed genes.

In one aspect of the invention, design elements to promote TGS are shown herein for the siRNA EF52 to the EF1A promoter which was previously shown to induce transcriptional silence of the EF1A promoter (Morris et al., 2004b). Previous studies have demonstrated that transcriptional inhibition was associated with de novo DNA methylation within the siRNA-targeted sequence, and was relieved with the drugs 5' azacytidine (5'-AzaC) and trichostatin A (TSA), inhibitors of DNA methylation and histone deacetylation respectively. Notably, gene silencing required the siRNAs access to the nucleus in order to down-regulate transcription. We demonstrate here that siRNA induced histone methylation (Histone 3 Lysine 9 and Histone 3 Lysine 27, H3K9 and H3K27, respectively) of the targeted promoter is dependent on nuclear specific delivery of the EF52 siRNA, is the result of the antisense strand, and requires RNA polymerase II. Moreover, we show direct evidence that siRNA EF52 binds DNMT3A in a strand specific manner and co-immunoprecipitated not only with the flag-tagged DNMT3A but also the targeted promoter in a H3K27 methyl-specific manner. The observations of strand specific siRNA mediated TGS was substantiated by targeting the U3 region of the HIV-1 LTR/promoter.

In a second aspect of the invention, we describe the role of Argonaute 1 (Ago1) in directing transcriptional silencing at both the chemokine receptor CCR5 (HIV-1 co-receptor) and the tumor suppressor RASSF1A promoters. Ago1 is required for siRNA mediated histone H3 lysine-9 di-methylation (H3K9$^{me2+}$) at the targeted CCR5 promoter, and knockdown of Ago1 results in the loss of H3K9$^{me2+}$, disrupting the overall potency of TGS. Co-immunoprecipitations indicate that Ago1 associates with RNA polymerase II (RNAPII), and chromatin immunoprecipitations (ChIP) of endogenously silenced CCR5 promoters show that Ago1 and RNAPII co-localize to epigenetically silenced genomic loci, suggesting the involvement of an RNA component that is recognized by Ago1. Furthermore, the HIV-1 TAR RNA-binding protein 2 (TRBP2) is enriched at silenced promoters, along with histone H3 lysine-27 tri-methylation (H3K27$^{me3+}$), a histone methyl-mark that recruits the Polycomb group (PcG) repressor proteins. Our results suggest that Ago1 is involved in the initiation and spreading of siRNA mediated TGS, as well as transcriptional silencing at facultative heterochromatin, linking the RNAi machinery with RNAPII transcription and histone regulated control of gene expression.

In a third aspect of the invention, a model for siRNA mediated TGS in human cells involving a transcriptional silencing complex (TSC) containing Ago1, TRBP2, siRNA, and possibly chromatin remodeling factors (i.e. HDAC-1, G9a, EZH2, DNMT3a). The TSC may be directed by siRNAs to their target promoters in an RNAPII-dependent manner, and the observation here that Ago1 associates with RNAPII suggests that RNAPII may provide a docking site for the TSC. Upon siRNA loading into the TSC, the antisense strand may guide the TSC to a low copy promoter-specific RNA that corresponds to the siRNA targeted promoter. This would allow for the formation of an RNA:RNA duplex between the antisense strand of the siRNA and either a nascent low copy-promoter specific RNA while it is being transcribed or a low copy-promoter specific RNA that is already a component of the local chromatin structure. Recognition of the siRNA target site would potentially stall the low copy-promoter specific RNA-scanning TSC:RNAPII complex and initiate the formation of facultative heterochromatin by recruiting histone methyltransferases and possibly PcG repressor complexes, which have recently been linked to Ago1 and the RNAi machinery in *Drosophila*. The inclusion of TRBP2 in the TSC suggests a potentially important role for this protein in Ago1 mediated RNA binding.

An alternative model implicated by the observed spreading of TGS and facultative heterochromatin from a promoter nucleation site would involve the siRNA antisense strand-directed TSC:RNAPII complex moving along the targeted RNAPII-transcribed promoter/gene, potentially modifying the H3 histones as they are reconstituted into nucleosomes immediately following transcription. Both of these models, or an amalgamation of the two, would necessitate the involvement of RNAPII, which is consistent with recent evidence that RNAPII function is required for histone methylation and TGS at siRNA-targeted promoters in human cells and in *S.*

*Pombe*, suggesting an Ago1 and RNAPII-dependent mechanism of transcriptional silencing that is evolutionarily conserved. Additionally, the recent discovery and characterization of a vast array of small (21- to 26-nt), non-coding RNAs is changing the classical understanding of gene regulation, and taken together with the data presented here, suggests that these non-coding RNAs may play a more profound role in writing the histone code and regulating gene expression at the level of DNA.

Thus, the present invention provides a method of reducing gene expression of a target gene using an siRNA molecule. In one embodiment, the siRNA molecule increases methylation of histones associated with the target gene. In a second embodiment, the siRNA molecule is directed to the promoter region of the gene. In a third embodiment, the siRNA molecule binds to a sequence within about 150 bp of the transcription start site. As used herein, the term transcriptional start site refers to the nucleotide in a gene from which transcription is initiated and lies between the TATA box (TATA or TATAA sequences) and the translation initiation site.

In one aspect, the present invention provides a method for TGS in a mammalian, including human, cell comprising exposing or introducing into the cell a siRNA which is specific for a target sequence in the promoter region of a gene to be silenced.

In another aspect, the present invention provides a method for TGS in a mammalian, including human, cell comprising introducing into the cell DNA sequences encoding a sense strand and an antisense strand of an siRNA which is specific for a target sequence in the promoter region of a gene to be silenced, preferably under conditions permitting expression of the siRNA in the cell, and wherein the siRNA induces histone modifications characteristic of silent chromatin and/or methylation of the gene.

In a further aspect, the present invention provides a method for TGS in a mammalian, including human, cell comprising introducing into the cell an siRNA molecule which is specific for a target sequence in the promoter region of a gene to be silenced and which interacts with Ago1 to direct transcriptional silencing of the gene of interest.

In a still further aspect, the present invention provides siRNA molecules, each comprising a sense strand and an antisense strand, wherein the antisense strand has a sequence sufficiently complementary to a promoter region of a gene of interest to direct TGS of the gene of interest.

In another aspect, the present invention provides pharmaceutical compositions containing the disclosed siRNA molecules.

Possible target genes for TGS in a mammalian, including human, cell include those associated with disease, including those involved with response to infectious agents (e.g., bacteria, viruses, fungi, etc.), cancer genes, genes leading to disease, or any gene for which TGS is desired.

The siRNA molecule may have different forms, including a single strand, a paired double strand (dsRNA) or a hairpin (shRNA) and can be produced, for example, either sythetically or by expression in cells. In one embodiment, DNA sequences for encoding the sense and antisense strands of the siRNA molecule to be expressed directly in mammalian cells can be produced by methods known in the art, including but not limited to, methods described in U.S. published application Nos. 2004/0171118 A1, 2005/0244858 A1 and 2005/0277610 A1, each incorporated herein by reference.

In one aspect of the invention, DNA sequences encoding a sense strand and an antisense strand of a siRNA specific for a target sequence of a gene are introduced into mammalian cells for expression. To target more than one sequence in the gene (such as different promoter region sequences and/or coding region sequences), separate siRNA-encoding DNA sequences specific to each targeted gene sequence can be introduced simultaneously into the cell. In accordance with another embodiment, mammalian cells may be exposed to multiple siRNAs that target multiple sequences in the gene.

The siRNA molecules generally contain about 19 to about 30 base pairs, and preferably are designed to cause methylation of the targeted gene sequence. In one embodiment, the siRNA molecules contain about 19-23 base pairs, and preferably about 21 base pairs. In another embodiment, the siRNA molecules contain about 24-28 base pairs, and preferably about 26 base pairs. In a further embodiment, the dsRNA has an asymmetric structure, with the sense strand having a 25-base pair length, and the antisense strand having a 27-base pair length with a 2 base 3'-overhang. In another embodiment, this dsRNA having an asymmetric structure further contains 2 deoxynucleotides at the 3' end of the sense strand in place of two of the ribonucleotides. Individual siRNA molecules also may be in the form of single strands, as well as paired double strands ("sense" and "antisense") and may include secondary structure such as a hairpin loop. Individual siRNA molecules could also be delivered as precursor molecules, which are subsequently altered to give rise to active molecules. Examples of siRNA molecules in the form of single strands include a single stranded anti-sense siRNA against a non-transcribed region of a DNA sequence (e.g. a promoter region).

The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3' end of antisense strand and are sufficiently complementary to a nucleotide sequence of the RNA produced from the target gene.

The precursor RNAi molecule, may also have one or more of the following additional properties: (a) the antisense strand has a right shift from the typical 21 mer and (b) the strands may not be completely complementary, i.e., the strands may contain simple mismatch pairings. A "typical" 21 mer siRNA is designed using conventional techniques, such as described above. This 21 mer is then used to design a right shift to include 1-7 additional nucleotides on the 5' end of the 21 mer. The sequence of these additional nucleotides may have any sequence. Although the added ribonucleotides may be complementary to the target gene sequence, full complementarity between the target sequence and the siRNA is not required. That is, the resultant siRNA is sufficiently complementary with the target sequence. The first and second oligonucleotides are not required to be completely complementary. They only need to be substantially complementary to anneal under biological conditions and to provide a substrate for Dicer that produces a siRNA sufficiently complementary to the target sequence. In one embodiment, the dsRNA has an asymmetric structure, with the antisense strand having a 25-base pair length, and the sense strand having a 27-base pair length with a 2 base 3'-overhang. In another embodiment, this dsRNA having an asymmetric structure further contains 2 deoxynucleotides at the 3' end of the antisense strand.

Suitable dsRNA compositions that contain two separate oligonucleotides can be linked by a third structure. The third structure will not block Dicer activity on the dsRNA and will not interfere with the directed destruction of the RNA transcribed from the target gene. In one embodiment, the third structure may be a chemical linking group. Many suitable chemical linking groups are known in the art and can be used.

Alternatively, the third structure may be an oligonucleotide that links the two oligonucleotides of the dsRNA is a manner such that a hairpin structure is produced upon annealing of the two oligonucleotides making up the dsRNA composition. The hairpin structure will not block Dicer activity on the dsRNA and will not interfere with the directed destruction of the RNA transcribed from the target gene.

The sense and antisense sequences may be attached by a loop sequence. The loop sequence may comprise any sequence or length that allows expression of a functional siRNA expression cassette in accordance with the invention. In a preferred embodiment, the loop sequence contains higher amounts of uridines and guanines than other nucleotide bases. The preferred length of the loop sequence is about 4 to about 9 nucleotide bases, and most preferably about 8 or 9 nucleotide bases.

In another embodiment of the present invention, the dsRNA, i.e., the precursor RNAi molecule, has several properties which enhances its processing by Dicer. According to this embodiment, the dsRNA has a length sufficient such that it is processed by Dicer to produce an siRNA and at least one of the following properties: (i) the dsRNA is asymmetric, e.g., has a 3' overhang on the sense strand and (ii) the dsRNA has a modified 3' end on the antisense strand to direct orientation of Dicer binding and processing of the dsRNA to an active siRNA. According to this embodiment, the longest strand in the dsRNA comprises 24-30 nucleotides. In one embodiment, the sense strand comprises 24-30 nucleotides and the antisense strand comprises 22-28 nucleotides. Thus, the resulting dsRNA has an overhang on the 3' end of the sense strand. The overhang is 1-3 nucleotides, such as 2 nucleotides. The antisense strand may also have a 5' phosphate.

Modifications can be included in the dsRNA, i.e., the precursor RNAi molecule, so long as the modification does not prevent the dsRNA composition from serving as a substrate for Dicer. In one embodiment, one or more modifications are made that enhance Dicer processing of the dsRNA. In a second embodiment, one or more modifications are made that result in more effective RNAi generation. In a third embodiment, one or more modifications are made that support a greater RNAi effect. In a fourth embodiment, one or more modifications are made that result in greater potency per each dsRNA molecule to be delivered to the cell. Modifications can be incorporated in the 3'-terminal region, the 5'-terminal region, in both the 3'-terminal and 5'-terminal region or in some instances in various positions within the sequence. With the restrictions noted above in mind any number and combination of modifications can be incorporated into the dsRNA. Where multiple modifications are present, they may be the same or different. Modifications to bases, sugar moieties, the phosphate backbone, and their combinations are contemplated. Either 5'-terminus can be phosphorylated.

In another embodiment, the antisense strand is modified for Dicer processing by suitable modifiers located at the 3' end of the antisense strand, i.e., the dsRNA is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the antisense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing. In a further invention, two terminal DNA bases are located on the 3' end of the antisense strand in place of two ribonucleotides forming a blunt end of the duplex on the 5' end of the sense strand and the 3' end of the antisense strand, and a two-nucleotide RNA overhang is located on the 3'-end of the sense strand. This is an asymmetric composition with DNA on the blunt end and RNA bases on the overhanging end.

Examples of modifications contemplated for the phosphate backbone include phosphonates, including methylphosphonate, phosphorothioate, and phosphotriester modifications such as alkylphosphotriesters, and the like. Examples of modifications contemplated for the sugar moiety include 2'-alkyl pyrimidine, such as 2'-O-methyl, 2'-fluoro, amino, and deoxy modifications and the like (see, e.g., Amarzguioui et al., 2003). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Locked nucleic acids, or LNA's, could also be incorporated. Many other modifications are known and can be used so long as the above criteria are satisfied. Examples of modifications are also disclosed in U.S. Pat. Nos. 5,684,143, 5,858,988 and 6,291,438 and in U.S. published patent application No. 2004/0203145 A1, each incorporated herein by reference. Other modifications are disclosed in Herdewijn (2000), Eckstein (2000), Rusckowski et al. (2000), Stein et al. (2001) and Vorobjev et al. (2001), each incorporated herein by reference.

Additionally, the siRNA structure can be optimized to ensure that the oligonucleotide segment generated from Dicer's cleavage will be the portion of the oligonucleotide that is most effective in inhibiting gene expression. For example, in one embodiment of the invention a 27-bp oligonucleotide of the dsRNA structure is synthesized wherein the anticipated 21 to 22-bp segment that will inhibit gene expression is located on the 3'-end of the antisense strand. The remaining bases located on the 5'-end of the antisense strand will be cleaved by Dicer and will be discarded. This cleaved portion can be homologous (i.e., based on the sequence of the target sequence) or non-homologous and added to extend the nucleic acid strand.

RNA may be produced enzymatically or by partial/total organic synthesis, and modified ribonucleotides can be introduced by in vitro enzymatic or organic synthesis. In one embodiment, each strand is prepared chemically. Methods of synthesizing RNA molecules are known in the art, in particular, the chemical synthesis methods as described in Verma and Eckstein (1998) or as described herein.

In another aspect, the present invention provides for a pharmaceutical composition comprising the siRNA of the present invention. The siRNA sample can be suitably formulated and introduced into the environment of the cell by any means that allows for a sufficient portion of the sample to enter the cell to induce gene silencing, if it is to occur. Many formulations for dsRNA are known in the art and can be used so long as siRNA gains entry to the target cells so that it can act. See, e.g., U.S. published patent application Nos. 2004/

0203145 A1 and 2005/0054598 A1, each incorporated herein by reference. For example, siRNA can be formulated in buffer solutions such as phosphate buffered saline solutions, liposomes, micellar structures, and capsids. Formulations of siRNA with cationic lipids can be used to facilitate transfection of the dsRNA into cells. For example, cationic lipids, such as lipofectin (U.S. Pat. No. 5,705,188, incorporated herein by reference), cationic glycerol derivatives, and polycationic molecules, such as polylysine (published PCT International Application WO 97/30731, incorporated herein by reference), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

It can be appreciated that the method of introducing siRNA into the environment of the cell will depend on the type of cell and the make up of its environment. For example, when the cells are found within a liquid, one preferable formulation is with a lipid formulation such as in lipofectamine and the siRNA can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate siRNA in a buffer or saline solution and directly inject the formulated dsRNA into cells, as in studies with oocytes. The direct injection of dsRNA duplexes may also be done. For suitable methods of introducing siRNA see U.S. published patent application No. 2004/0203145 A1, incorporated herein by reference.

Suitable amounts of siRNA must be introduced and these amounts can be empirically determined using standard methods. Typically, effective concentrations of individual siRNA species in the environment of a cell will be about 50 nanomolar or less 10 nanomolar or less, or compositions in which concentrations of about 1 nanomolar or less can be used. In other embodiment, methods utilize a concentration of about 200 picomolar or less and even a concentration of about 50 picomolar or less can be used in many circumstances.

The method can be carried out by addition of the siRNA compositions to any extracellular matrix in which cells can live provided that the siRNA composition is formulated so that a sufficient amount of the siRNA can enter the cell to exert its effect. For example, the method is amenable for use with cells present in a liquid such as a liquid culture or cell growth media, in tissue explants, or in whole organisms, including animals, such as mammals and especially humans.

Expression of a target gene can be determined by any suitable method now known in the art or that is later developed. It can be appreciated that the method used to measure the expression of a target gene will depend upon the nature of the target gene. For example, when the target gene encodes a protein the term "expression" can refer to a protein or transcript derived from the gene. In such instances the expression of a target gene can be determined by measuring the amount of mRNA corresponding to the target gene or by measuring the amount of that protein. Protein can be measured in protein assays such as by staining or immunoblotting or, if the protein catalyzes a reaction that can be measured, by measuring reaction rates. All such methods are known in the art and can be used. Where the gene product is an RNA species expression can be measured by determining the amount of RNA corresponding to the gene product. The measurements can be made on cells, cell extracts, tissues, tissue extracts or any other suitable source material.

The determination of whether the expression of a target gene has been reduced can be by any suitable method that can reliably detect changes in gene expression. Typically, the determination is made by introducing into the environment of a cell undigested siRNA such that at least a portion of that siRNA enters the cytoplasm and then measuring the expression of the target gene. The same measurement is made on identical untreated cells and the results obtained from each measurement are compared.

The siRNA can be formulated as a pharmaceutical composition which comprises a pharmacologically effective amount of a siRNA and pharmaceutically acceptable carrier. A pharmacologically or therapeutically effective amount refers to that amount of a siRNA effective to produce the intended pharmacological, therapeutic or preventive result. The phrases "pharmacologically effective amount" and "therapeutically effective amount" or simply "effective amount" refer to that amount of a RNA effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed dsRNA composition may be micellar structures, such as a liposomes, capsids, capsoids, polymeric nanocapsules, or polymeric microcapsules.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Suitably formulated pharmaceutical compositions of this invention can be administered by any means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In general a suitable dosage unit of siRNA will be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Pharmaceutical composition comprising the siRNA can be administered once daily. However, the therapeutic agent may also be dosed in dosage units containing two, three, four, five, six or more sub-doses administered at appropriate intervals throughout the day. In that case, the siRNA contained in each sub-dose must be correspondingly smaller in order to achieve the total daily dosage unit. The dosage unit can also be compounded for a single dose over several days, e.g., using a conventional sustained release formulation which provides sustained and consistent release of the siRNA over a several day period. Sustained release formulations are well known in the art. In this embodiment, the dosage unit contains a corresponding multiple of the daily dose. Regardless of the formulation, the pharmaceutical composition must contain siRNA in a quantity sufficient to inhibit expression of the target gene in the animal or human being treated. The composition can be compounded in such a way that the sum of the multiple units of siRNA together contain a sufficient dose.

Data can be obtained from cell culture assays and animal studies to formulate a suitable dosage range for humans. The dosage of compositions of the invention lies within a range of circulating concentrations that include the $ED_{50}$ (as determined by known methods) with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound that includes the $IC_{50}$ (i.e., the concentration of the test compound which achieves a half-maximal inhibition of symptoms) as determined in cell culture. Such information can be used to more accurately determine useful doses in humans. Levels of dsRNA in plasma may be measured by standard methods, for example, by high performance liquid chromatography.

In a further aspect, the present invention relates to a method for TGS in a mammalian, including human, cell. The method comprises introducing the siRNA into the appropriate cell. The term "introducing" encompasses a variety of methods of introducing DNA into a cell, either in vitro or in vivo. Such methods include transformation, transduction, transfection, and infection. Vectors are useful and preferred agents for introducing DNA encoding the siRNA molecules into cells. The introducing may be accomplished using at least one vector. Possible vectors include plasmid vectors and viral vectors. Viral vectors include retroviral vectors, lentiviral vectors, or other vectors such as adenoviral vectors or adeno-associated vectors. In one embodiment, the DNA sequences are included in separate vectors, while in another embodiment, the DNA sequences are included in the same vector. The DNA sequences may be inserted into the same vector as a multiple cassettes unit. Alternate delivery of siRNA molecules or DNA encoding siRNA molecules into cells and tissues may also be used in the present invention, including liposomes, chemical solvents, electroporation, viral vectors, pinocytosis, phagocytosis and other forms of spontaneous or induced cellular uptake of exogenous material, as well as other delivery systems known in the art.

Suitable promoters include those promoters that promote expression of the interfering RNA molecules once operatively associated or linked with sequences encoding the RNA molecules. Such promoters include cellular promoters and viral promoters, as known in the art. In one embodiment, the promoter is an RNA Pol III promoter, which preferably is located immediately upstream of the DNA sequences encoding the interfering RNA molecule. Various viral promoters may be used, including, but not limited to, the viral LTR, as well as adenovirus, SV40, and CMV promoters, as known in the art.

In one embodiment, the invention uses a mammalian U6 RNA Pol III promoter, and more preferably the human U6snRNA Pol III promoter, which has been used previously for expression of short, defined ribozyme transcripts in human cells (Bertrand et al., 1997; Good et al., 1997). The U6 Pol III promoter and its simple termination sequence (four to six uridines) were found to express siRNAs in cells. Appropriately selected interfering RNA or siRNA encoding sequences can be inserted into a transcriptional cassette, providing an optimal system for testing endogenous expression and function of the RNA molecules.

In a further aspect, the invention provides a method for TGS in a mammalian, including human, cell comprising introducing into the cell DNA sequences encoding a sense strand and an antisense strand of an siRNA, which is specific for a target sequence in the gene to be silenced, preferably under conditions permitting expression of the siRNA in the cell, and wherein the siRNA directs methylation of said gene of interest. In an embodiment, methylation is directed to a sequence in the promoter region of the gene. Alternately, methylation is directed to a sequence in the coding region. Target sequences can be any sequence in a gene that has the potential for methylation. In a preferred embodiment, the target sequences may contain CpG islands. The directed methylation can lead to inactivation of the gene. To target more than one sequence in the gene (such as different promoter region sequences and/or coding region sequences), separate siRNA-encoding DNA sequences specific to each targeted gene sequence can be introduced simultaneously into the cell. In addition, cells may be exposed to multiple siRNAs that target multiple sequences in the gene.

Once a target sequence or sequences have been identified for methylation in accordance with the invention, the appropriate siRNA can be produced, for example, either synthetically or by expression in cells. In a one embodiment, the DNA sequences encoding the sense and antisense strands of the siRNA molecule can be generated by PCR. In another embodiment, the siRNA encoding DNA is cloned into a vector, such as a plasmid or viral vector, to facilitate transfer into mammals. In another embodiment, siRNA molecules may be synthesized using chemical or enzymatic means.

To facilitate nuclear retention and increase the level of methylation, the sense and antisense strands of the siRNA molecule may be expressed in a single stranded form, for example as a stem loop structure, as described above. Alternatively, or in concomitance, the factor(s) involved in the active cellular transport of siRNA's, such as Exportin 5, may be downregulated employing synthetic siRNA, antisense, ribozymes, or any other nucleic acid, antibody or drug, proven to be effective in downregulating the gene(s) of interest.

The procedure for a PCR-based approach is depicted schematically in FIG. 1 and illustrated in Example 1. In one embodiment, a universal primer that is complementary to the 5' end of the human U6 promoter is used in a PCR reaction along with a primer(s) complementary to the 3' end of the promoter, which primer harbors appended sequences which are complementary to the sense or antisense siRNA genes (FIG. 1A). The sense or antisense sequences are followed by a transcription terminator sequence (Ter), which is preferably a stretch of 4-6 deoxyadenosines, and more preferably a stretch of 6 deoxyadenosines, and by a short additional "stuffer-tag" sequence that may include a restriction site for possible cloning at a later stage. The resulting PCR products include the U6 promoter sequence, the siRNA sense or antisense encoding sequence, a terminator sequence, and a short tag sequence at the 3' terminus of the product.

Figure 1A:
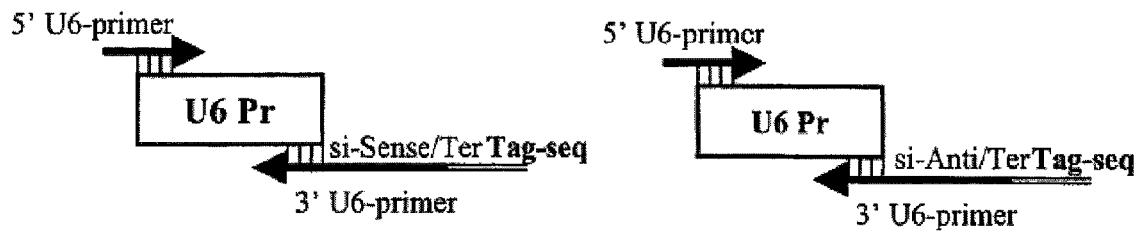
FIGS. 1A-1D show a schematic representation of a polymerase chain reaction (PCR) strategy used to yield U6 transcription cassettes expressing siRNAs. The 5' PCR primer is complementary to the 5' end of the U6 promoter and is standard for all PCR reactions.
Figure 1B:
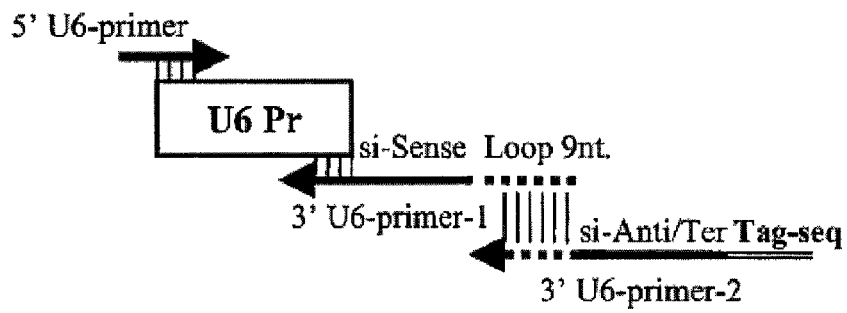
Figure 1C:
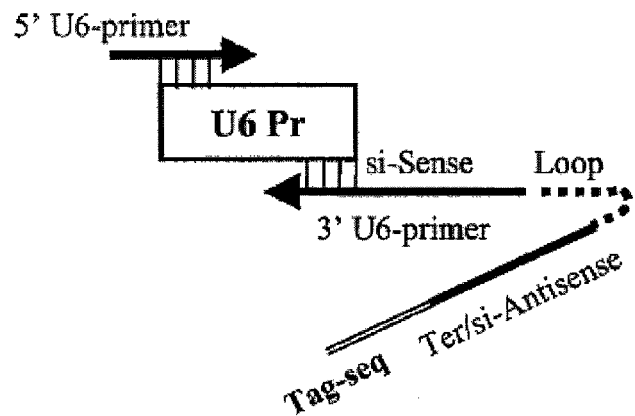
Figure 1D:
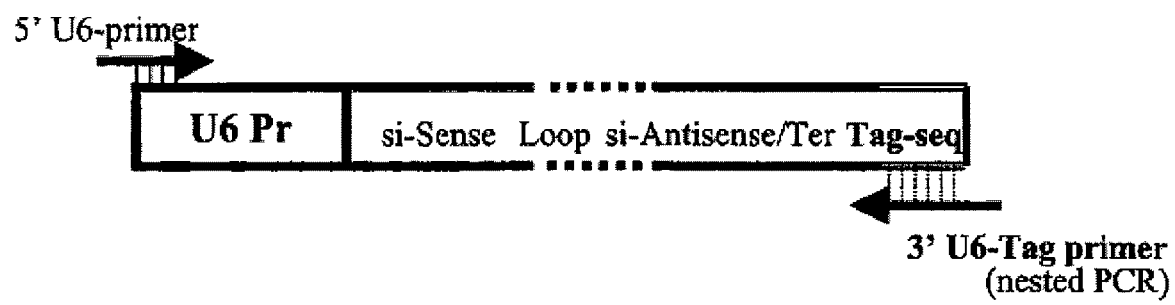

In another embodiment, both the sense and antisense sequences can be included in the same cassette (FIGS. 1B, 1C and 1D). In this case a nucleotide loop, preferably containing 9 nucleotides, is inserted between the sense and antisense siRNA sequences. The resulting single PCR product includes the U6 promoter, the siRNA sense and antisense encoding sequences in the form of a stem-loop, the Pol III terminator sequence, and the "stuffer" tag sequence (FIG. 1D). To construct this cassette two 3' primers are used. The first PCR reaction employs the 5' U6 universal (or "common") primer and a 3' primer complementary to a portion of the U6 promoter, followed by sequences complementary to the siRNA sense encoding sequence and the 9 nt. loop (FIG. 1B). Preferably one microliter of this first reaction is re-amplified in a second PCR reaction that employs the same 5' U6 primer and a 3' primer harboring sequences complementary to the 9 nt. loop appended to the antisense strand, Ter and "stuffer" tag sequence (FIG. 1B).

In another embodiment, a one step PCR reaction is conducted with a single 3' primer that harbors the sense, loop, antisense, Ter and "stuffer" tag sequences (FIG. 1C).

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., *Molecular Cloning* (Cold Spring Harbor Laboratory Press, Cold Spring Harbor, N.Y., 1982); Sambrook et al., *Molecular Cloning,* 2nd Ed. (Cold Spring Harbor Laboratory Press, Cold Spring Harbor, N.Y., 1989); Sambrook and Russell, *Molecular Cloning,* 3rd Ed. (Cold Spring Harbor Laboratory Press, Cold Spring Harbor, N.Y., 2001); Ausubel et al., *Current Protocols in Molecular Biology* (John Wiley & Sons, updated through 2005); Glover, *DNA Cloning* (IRL Press, Oxford, 1985); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, *Antibodies*, (Cold Spring Harbor Laboratory Press, Cold Spring Harbor, N.Y., 1998); Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology,* 6th Edition, (Blackwell Scientific Publications, Oxford, 1988); Hogan et al., *Manipulating the Mouse Embryo*, (Cold Spring Harbor Laboratory Press, Cold Spring Harbor, N.Y., 1986); Westerfield, M., *The zebrafish book. A guide for the laboratory use of zebrafish* (*Danio rerio*), 4th Ed., (Univ. of Oregon Press, Eugene, Oreg., 2000).

EXAMPLES

The present invention can be described by reference to the following Examples, which are offered by way of illustration and are not intended to limit the invention in any manner. Standard techniques well known in the art or the techniques specifically described below were utilized.

Furthermore, the following summary of the Examples is not intended to be limiting to each respective Example and full details can be found in the respective priority documents.

| Examples 1-6 (U.S. Ser. No. 10/446,635) | Examples 7-12 (U.S. Ser. No. 60/683,782) | Examples 13-18 (this application) |
|---|---|---|
| siRNA induces DNA methylation | siRNA induces methylation of histones associated w/target gene | Ago1 recruits histone methyltransferase |
| Reduces or increases target gene expression | Reduces target gene expression | Reduces target gene expression. Ago1 directs siRNA mediated TGS |
| siRNA ~21-28bps, 19-23bps, 21bps, 24-28bps, 26bps, 28bps | siRNA ~18-29bps, ~18-23bps, ~18-21bps | 21-26nt noncoding RNAs |
| siRNA complementary to RASSF1A region directs methylation of RASSF1A gene promoter leading to reduced RASSF1A expression | Anti-sense siRNA EF52 binding to DNMT3A directs methylation of histones related to target gene leading to reduction of target gene expression | Ago1 associates w/target promoters (CCR5 and RASSF1A) via an interaction with RNAPII leading to TGS |
| | | Transitional silencing complex (TSC): Ago1, TRBP2, siRNA and possibly chromatin remodeling factors |

Example 1

Expression of Short Hairpin RNAs Complementary to Regions of RASSF1A

This example demonstrates expression of short hairpin RNAs that are complementary to regions of a human tumor suppressor gene RASSF1A. The consequences of this expression were monitored by determining the patterns of DNA methylation in the promoter and part of the coding region of this gene, which is also susceptible to methylation in cancer cells. The DNA sequence of the RASSF1A gene is depicted below:

```
RASSF1A Promoter:
                                        (SEQ ID NO: 2)
ggggctctgc gagagcgcgc ccagcccgc cttcgggccc cacagtccct gcacccaggt ttccattgcg cggctctcct
```

-continued
```
cagctccttc ccgccgccca gtctggatcc tgggggagc gctgaagtcg gggcccgccc tgtggcccg cccggcccgc gcttgct*agc* gcccaaagcc
```

RASSF1A transcript:

(SEQ ID NO: 3)
```
agcgaagcac gggcccaaCC GGgccatgtcg ggggagcct gagctcattg agctgcggga gctggcaccc gctgggcgcg ctgggaaggg ccgcaccgg ctggagcgtg ccaacgcgct gcgcatcgcg cggggcaccg cgtgcaaccc cacacggcag ctggtccctg gccgtggcca ccgcttccag cccgcggggc ccgccacgca cacgtggtgc gacctctgtg gcgacttcat ctggggcgtc gtgcgcaaag gcctgcagtg cgcgcgtgag tagtggcccc gcgcgcctac
``` agc is where transcription probably starts atg is the methionine codon

The bolded sequences were targeted by siRNAs of the invention.

PCR reactions are performed using a plasmid containing the human U6 promoter as template to yield U6 transcription cassettes expressing siRNAs. The 5' oligonucleotide (5'U6 universal primer) is complementary to 29 nucleotides at the 5' end of the U6 promoter (bold italics indicate the nucleotides complementary to those on the promoter). 5'U6 MluI primer:

(SEQ ID NO: 4)
```
5' AATCGA ACGCGT GGATCCAAGGTCGGGCAGGAAGAGGGCCT 3'
       MluI                U6
```

This U6 common 5' primer, used for all PCR steps, binds to the 5' end of the U6 promoter and includes an Mlu I restriction site for cloning purposes. The 3' oligonucleotides, which contain either the sense, antisense, or both siRNA-coding sequences (siDNAs), are depicted in FIG. 1 and described herein. The last 20 nucleotides at the 3' end of all 3' PCR primers are complementary to the last 20 nucleotides of the U6 promoter which is: 5'GTGGAAAGG ACGAAA-CACCG3' (SEQ ID NO:5). All PCR reactions were carried out as follows: 1 min. at 94° C., 1 min. at 55° C. and 1 min. at 72° C. for 30 cycles. The PCR products can be directly transfected into cells (e.g., with prior cloning into an expression vector), in which event the PCR primers can be kinased with non-radioactive ATP prior to amplification and purified on Quiagen columns prior to using them in the PCR reactions. The PCR products also can be purified on Quiagen columns.

The 3' primers used to make siRNA expression cassettes are depicted below:

Primers used to make PCR products encoding siRNA's complementary to the promoter region of the RASSF1A gene:

3'PR 1

(SEQ ID NO: 6)
```
5'CTACACAAA GGCGGGCCCCGACTTCAGCG C
   loop         si-sense          +1

GGTGTTTCGTCCTTTCCACAA 3'
     U6
```

3'PR 2

(SEQ ID NO: 7)
```
5'AACTC GAATTC AAAAAA GCGCTGAAGTCGGGGCCCGCC
       EcoRI   Ter.        si-antisense CTACACAAA 3'
  Loop
```

Primers used to make PCR products encoding siRNA's complementary to the transcribed region of the RASSF1A gene:

3'TR 1

(SEQ ID NO: 8)
```
5'CTACACAAA CGACATGGCCCGGTTGGGCC C
    loop          si-sense        +1

GGTGTTTCGTCCTTTCCACAA 3'
     U6
```

3'TR 2

(SEQ ID NO: 9)
```
5'AACTC GAATTC AAAAAA GGGCCCAACCGGGCCATGTCG
       EcoRI   Ter.        si-antisense CTACACAAA 3'
  Loop
```

Example 2

HeLa Cells Stably Transfected with the siRNA Expression Constructs

HeLa cells, which include in their genome the RASSF1A gene, were stably transfected with the siRNA expression constructs produced by the method shown above. The final siRNAs-containing PCR products were digested with MluI and EcoRI and cloned in the same sites of the pcDNA3.1 vector (Invitrogen) for expression in the mammalian cells. Digestion of pcDNA3.1 with MluI and EcoRI allows the replacement of the CMV promoter with the U6 siRNA cassettes. The Neomycin gene is the marker gene for selection in mammalian cells. Cells were selected for G418 resistance. Cells were monitored either in mixed population or clones of transfected cells.

Stable cell lines expressing all different siRNAs and 8 individual single clones for each of the siRNA expressing cells have thus far been obtained.

Example 3

Methods to Determine Methylation

Bisulfite:

In the mixed cell population, genomic DNA was isolated and treated with bisulfite, which changes unmethylated cytosines to thymidines. Methylated cytosines remain as cytosine. Thus, if the siRNAs direct methylation of the targeted sequences of the RASSF1A shown in Example 1, these DNAs will not be modified by bisulfite in the methylated region.

MSP Assay:

PCR primers specific for either methylated or unmethylated nucleotides were used in PCR reactions in accordance with the Methylation-specific PCR assay (MSP assay) described in Herman et al. Results showed that the siRNA that targets the promoter region and the siRNA that targets the RASSF1A transcript, were directing methylation of the RASSF1A gene. The MSP assay is sensitive and specific for methylation of virtually any block of CpG sites in a CpG island. The assay uses primers designed to distinguish methylated from unmethylated DNA in bisulfite-modified DNA, taking advantage of the sequence differences resulting from bisulfite modification. Unmodified DNA or DNA incompletely reacted with bisulfite can also be distinguished, since marked sequence differences exist between these DNAs.

Figure 2:
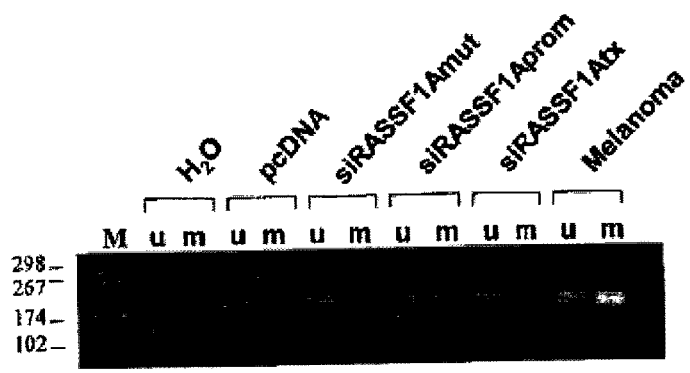
FIG. 2 shows the results of a methylation specific PCR (MSP) analysis of the RASSF1A promoter in siRNA transfected cells.

FIG. 2 shows results of the MSP analysis of the RASSF1A promoter in siRNA transfected cells. In the figure, H$_2$O represents a water control used in the PCR reactions. The following additional abbreviations were also used:

pcDNA: Cells transfected only with the vector (no siRNA)

siRASSF1Amut: Cells transfected with the mutant siRNA vector siRASSF1Aprom: Cells transfected with the siRNA vector directed against the RASSF1A promoter sequences siRASSF1Atx: Cells transfected with the siRNA vector directed against the RASSF1A transcript Melanoma: a control for RASSF1A methylation. This is DNA from a melanoma tumor, which is methylated in the RAS promoter.

M, size markers m, MSP done with primers specific for a methylated RASSF1A promoter u, MSP done with primers specific for an unmethylated RASSF1A promoter The following primers were used in the MSP reaction: methylated DNA-specific primers, M210 (5' GGGTTTTGC-GAGAGCGCG 3') (SEQ ID NO:10) and M211 (5'GCTAA-CAAACGC GAACCG 3') (SEQ ID NO:11) or unmethylated DNA-specific primers UM240 (5' GGGGTTTTGT GAGAGTGTGTTTAG 3') (SEQ ID NO:12) and UM241 (5' TAAACACTAACAAACACAAAC CAAAC 3') (SEQ ID NO:13) (Liu, L. et al., 2002).

Restriction Analysis:

Restriction analyses with an enzyme that recognizes only the methylated sequence (BstU1), also confirmed the presence of methylated sites in the RASSF1A gene.

Sequencing:

Specific deoxynucleotide primed sequencing revealed that 14 out of 17 potential methylation sites analyzed in the RASSF1A gene were methylated in cell populations expressing the siRNA directed against the RASSF1A promoter, and 17 out of 17 sites were methylated in cells expressing the siRNA directed against a CpG island in the RASSF1A transcript. Results are shown in FIG. 3. The level of methylation in the promoter region was higher in some of the single clones analyzed. Specific integration sites of siRNAs in the cellular genome (by using the appropriate delivering vector) could be used to achieve complete promoter methylation.

Sequence data were obtained by sequencing of the PCR products obtained from the MSP reactions of Example 4 (FIG. 2). In FIG. 3, sample designation is the same as in FIG. 2. FIG. 3 shows the RASSF1A promoter sequence relative to the ATG translation start site (i.e. −30 indicates 30 nucleotides upstream). Open circles represent unmethylated cytosines at CG sequences. Closed circles indicate methylated cytosines at CG sequences.

Example 4

Negative Control

As a negative control, DNA was extracted from cells expressing a mutated siRNA, was analyzed, and showed no effects on the methylation of the RASSF1A gene. In this analysis, PCR products were produced as described in Example 1, but using the 3' primers shown below. For the mutant there were two transversions (CCGG to GGCC) and one transition (C to T) to make sure it would be inactive.

Mutant primers against transcribed region:

```
3'MT 1
                                               (SEQ ID NO: 14)
              (c)     (ccgg)
5'CTACACAAA CGATATGGCGGCCTTGGGCC C
    loop           si-sense        +1

GGTGTTTCGTCCTTTCCACAA 3'
     U6

3'MT 2
                                               (SEQ ID NO: 15)
5'AACTC GAATTC AAAAAA GGGCCCAAGGCCGCCATATCG
       EcoRI   Ter.         si-antisense CTACACAAA 3'
  Loop
```

Example 5

Figure 4:
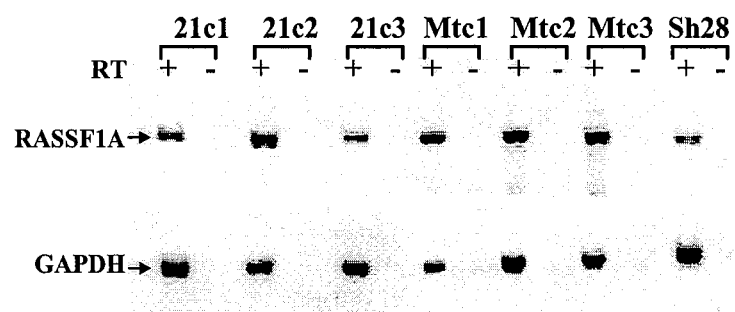
FIG. 4 shows the results of RASSF1A intracellular expression in stable clones and cell populations (siPR28) transfected with specific shRNAs.

Reduction of RASSF1A Intracellular Expression in Cells Transfected with shRNAs Directed Against Promoter Sequences FIG. 4 shows the reduction of RASSF1A RNA transcripts detected by reverse transcriptase PCR (RT-PCR) reactions. Hela cells were transfected with shRNAs directed against promoter sequences of RASSF1A. Cells were collected after 48-56 hr. and the RNA was extracted using RNA STAT60 as suggested by the manufacturer. Quantitative PCR reactions were performed by preparing 100 µl PCR mixes containing standard PCR buffer, dNTPs, 1 µg of each RNA sample, and two 3' primers specific to either the RASSF1A transcript or to the GAPDH cellular gene. GAPDH is used as an internal control to verify the integrity and amount of RNA analyzed in each reaction. After the samples were heated at 80° C. for 1 minute and slow cooled to room temperature, they were thoroughly mixed and divided into two 50 µl aliquots. 1-2 units of reverse transcriptase were added to half of the reactions while the other half were used as controls to exclude DNA contaminations. All samples were placed at 37° C. for 5 minute to complete the extension reactions. Following the extensions (and cDNA synthesis) the samples were thoroughly mixed and divided once again into two 25 µl aliquots. The specific 5' primers for the RASSF1A or the GAPDH were added to the 25 µl aliquots and the PCR reactions were completed as for the methylation-specific PCR assay.

As shown in FIG. 4, representative clonal cell lines from cells transfected with the 21 nucleotides shRNAs directed against the RAS promoter (21c1, 21c2, 21c3), and the Hela cell population transfected with a 28 nucleotides shRNA (sh28) were analyzed for decreased RNA expression. Clonal cell lines tranfected with the shRNA mutant (Mtc1, Mtc2, Mtc3) were also analyzed as controls. After normalization with the GAPDH internal control, a clear and specific RASSF1A RNA down-regulation can be detected in two of the three clones expressing shRNA directed against promoter sequences, but in none of the mutant shRNA clones used as controls. The −RT controls showed no DNA contamination. These results indicate that specific shRNA methylation of the RASSF1A promoter results in down-regulation of the intracellular RASSF1A transcripts.

Example 6

Decreased Expression of RASSF1A Transcripts

Figure 5:
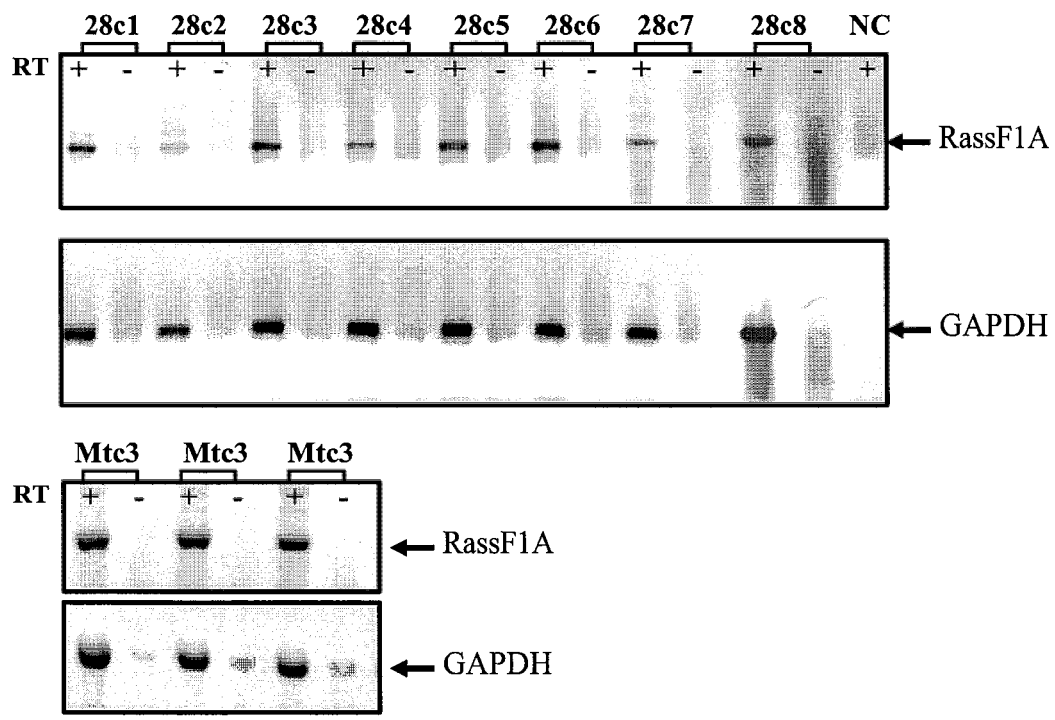
FIG. 5 shows the results of RASSF1A intracellular expression in stable clones transfected with 28 nucleotides shRNAs.

Several clonal HeLa cell lines transfected with 28 nucleotides shRNAs directed against the promoter sequences were analyzed by Reverse Transcriptase dependent PCRs as described in Example 8. The results shown in FIG. 5 show decrease expression of RASSF1A transcripts in many of the clones analyzed. Similar results were obtained by expressing the shRNAs from lentiviral vector backbones (not shown), which may be the method of choice (but not the only method) for long-term expression of shRNAs and gene silencing. The results obtained with the clonal cell lines transfected with the various shRNAs are summarized in FIG. 6.

The above demonstrates the invention's utility for, among other things, designing and using siRNAs to direct DNA methylation in either a promoter region or certain coding region of a gene. Directing promoter methylation of a gene by targeting siRNAs against CpG islands of RNA transcripts should be a potent inhibitor of intracellular gene expression.

Example 7

Methods Used for Examples 8-12

Chromatin immunoprecipitation Assay (CHiP):

Chromatin immunoprecipitation was performed on $4.0 \times 10^6$ 293T transfected with siRNA EF52 or control CCR5 (10 nM using MPG 3 µl/ml of media) (Morris et al., 2004b). Forty-eight hours following transfection cultures were collected and ChiP assay performed as described (Strahl-Bolsinger et al., 1997). Cultures were specifically probed with anti-dimethyl-Histone H3 (Lys9) and anti-trimethyl-Histone H3 (Lys27) (Upstate catalog #07-441 and 07-449, respectively). The final elutes were assayed using PCR 30 cycles of 94:55:72° C. with primers 803 and 804 which specifically overlap the targeted EF1 alpha promoter (Morris et al., 2004a) and quantitated using the IDV values determined from analysis with the Alpha Innotech.

Detection of Flag-Tagged Proteins in Biotin Labeled siRNA Pulldowns:

A total of $4.0 \times 10^6$ 293T cells were transfected with 15 µg of one of 9 Flag-tagged expression vectors (DNMT-1, 3A, 3A2, 3B1, 3B2, HP1-alpha, HP1-beta, HP1-gamma, or the negative control helicase Prp2) using Lipofectamine 2000™. All DNMTs were supplied by A. Riggs and all HP1s were a gift R. Losson (Nielsen et al., 2001). (2) Forty-eight hours later the cell lysates (cytoplasmic and nuclear fractions) were isolated each in 500 µl of lysis buffer (1 mM PMSF, 20 units RNasin, 10 mM Tris-HCl pH 7.4, 10 mM NaCl, 3 mM $MgCl_2$, 0.1 mM DTT, and 0.5% NP40). (3) A mixture of 125 µl of cytoplasmic and nuclear fractions were incubated for 3 hrs at 4° C. with 500 nM 5'Biotin end-labeled EF52. Next Dynal Avidin/magnetic beads ($7 \times 10^7$ beads) were washed in lysate buffer and then added directly to the siRNA/Flag-Tagged containing lysates and incubated at 4° C. for 1 hr. The siRNA/Flag complexes were pulled-down by magnetic bead binding and washed 5x' s in lysate buffer. Finally, the bound protein complexes were eluted from the Avidin-biotin bound beads/siRNA by incubation in 100 µl of elution buffer (Tris-Cl pH 6.0, 1 mM EDTA, 2.0 M NaCl, 0.5M $MgCl_2$) at 55° C. for 5 minutes. The eluted protein complexes were electrophoresed in denaturing PAGE and subjected to western blot analysis with an anti-Flag antibody.

Detection of siRNAs from Flag-Tag Pulldowns:

Flag-tagged DNMT1 and 3A were as described previously. The cell lysates/extracts were then incubated with either the siRNA EF52, sense (S) or antisense (AS) EF52 (500 nM) for 3 hrs at 4° C. Next, a flag-tag immunoprecipitation was performed for each DNMT complex containing the putative bound siRNAs followed by deproteinization of the complex, phenol/chloroform extraction, and release of the bound siRNA. Detection of the released siRNA, either sense or antisense, was performed according to Weinberg et al. (2006).

ChiP/Biotin-RNA Co-Immunoprecipitation:

A total of $4.0 \times 10^6$ 293T cells were plated and 24 hrs later transfected with 100 nM EF52 biotin labeled siRNA (antisense alone) using MPG (3 µl/ml of media). Forty eight hours following the siRNA/MPG transfection cultures were collected and a ChiP assay performed as described previously with a slight modification. Following the immunoprecipitation with the H3K27 tri-methyl specific antibody the elutes were incubated with 100 µl ($6-7 \times 10^8$ beads/ml) of Dynabeads™ M-280 Streptaviden pre-washed in 2x wash buffer (50 mM Tris HCl, 400 mM NaCl pH 7.4). The elute/bead slurry was incubated at 4° C. for 15 minutes on an orbital shaker followed by capture with a magnetic bead separator. The captured beads were washed 3 times in 2x wash buffer and then eluted in 100 µl of 2x elute buffer (10 mM Tris-HCL (pH 6.0), 1 mM EDTA and 2.0M NaCl) at 65° C. for 5 minutes. The resultant elutes were then reverse cross-linked and DNA recovered by phenol/chloroform extraction followed by PCR 35 cycles of 94:55:72° C. for the EF1 alpha promoter with primers 803 and 804 (Morris et al., 2004a).

ChiP/DNMT3A-Flag/Biotin-RNA Co-Immunoprecipitation:

A total of $4.0 \times 10^6$ 293T cells were plated and 24 hrs later transfected with 100 nM EF52 biotin labeled siRNA (antisense or sense alone) using MPG (3 µl/ml of media). Forty eight hours following the sense or antisense siRNA/MPG transfection cultures were collected and a ChiP assay performed as described previously with a slight modification. Following the immunoprecipitation with the H3K27 tri-methyl specific antibody the elutes were incubated overnight with 40 µl of EZVIEW™ Red anti-Flag M2 affinity gel beads (Sigma™). Next the bound beads were washed 3 times with TBS-Mod Buffer (50 mM Tris HCl, 400 mM NaCl pH 7.4) and then eluted by competition with 3x Flag-peptide 15 µg. The resultant elutes were then transferred to 100 µl ($6-7 \times 10^8$ beads/ml) of Dynabeads™ M-280 Streptaviden pre-washed in 2x wash buffer (50 mM Tris HCl, 400 mM NaCl pH 7.4). The elute/bead slurry was incubated at 4° C. for 15 minutes on an orbital shaker followed by capture with a magnetic bead separator. The captured beads were washed 3 times in 2x wash buffer and then eluted in 100 µl of 2x elute buffer (10 mM Tris-HCL (pH 6.0), 1 mM EDTA and 2.0M NaCl) at 65° C. for 5 minutes. The resultant elutes were then reverse cross-linked and DNA recovered by phenol/chloroform extraction followed by PCR 35 cycles of 94:55:72° C. for the EF1 alpha promoter with primers 803 and 804 (Morris et al., 2004a).

HIV-1 U3 LTR Targeting:

Small interfering RNAs were constructed following established protocols (Ambion Silencer™). EF1-alpha siRNA target sites were: EF52 5'-AAG GTG GCG CGG GGT AAA CTG-3' (SEQ ID NO:16), and the control GFP mRNA specific 5'-AAC GAT GCC ACC TAC GGC AAG-3' (kit control; SEQ ID NO:17), and negative control CCR5 specific 5'-AAT TCT TTG GCC TGA ATA ATT-3' (SEQ ID NO:18). Synthetic 5' end biotin labeled EF52 sense (S) 5'-CCA CCG CGC CCC AUU UGA CAA-3' (SEQ ID NO:19), antisense (AS) 5'AAG GUG GCG CGG GGU AAA CUG-3' (SEQ ID NO:20) and unmodified sense and antisense siRNAs used in co-immunoprecipitation assays were constructed at the City of Hope Beckman Research Institute DNA, RNA and Peptide Synthesis Facility. To generate the sense/antisense (S/AS) biotin end-labeled siRNAs equivalent volumes of 100 µM of the sense and antisense siRNAs were mixed together and incubated at 65° C. for 5 minutes followed by a 5 minute incubation on ice. HIV-1 U3 LTR targeted siRNAs were constructed and cloned into pCR4-TOPO (Invitrogen™) by PCR using the 5' U6+1 as described (Lee et al., 2002) with 3' primers; LTR-247(S): 5'AAA AAA AAG TGT TAG AGT GGA GGT TTG CGG TGT TTC GTC CTT TCC ACA A-3' (SEQ ID NO:21), LTR-362(AS): 5'AAA AAA AAG AAA GTC CCC AGC GGA AAG CGG TGT TTC GTC CTT TCC ACA A-3' (SEQ ID NO:22), GFP (AS): 5'AAA AAA AAC GAT GCC ACC TAC GGC AAG CGG TGT TTC GTC CTT TCC ACA A-3' (SEQ ID NO:23), GFP(S): 5'AAA AAA AAC TTG CCG TAG GTG GCA TCG CGG TGT TTC GTC CTT TCC ACA A-3' (SEQ ID NO:24), LTR-247c (AS): 5'-AAA AAA AAG TAT TAA AGT GGA AGT TTG CGG TGT TTC GTC CTT TCC ACA A-3' (SEQ ID NO:25), LTR-247c(S): 5'-AAA AAA AAC AAA CTT CCA CTT TAA TAC GGT GTT TCG TCC TTT CCA CAA-3' (SEQ ID NO:26), LTR-362c (AS): 5'-AAA AAA AAC TTT CCA CTG GGG CGT TCC GGT GTT TCG TCC TTT CCA CAA-3' (SEQ ID NO:27), LTR-362c(S): 5'-AAA AAA AAG GAA CGC CCC AGT GGA AAG CGG TGT TTC GTC CTT TCC ACA A-3' (SEQ ID NO:28). The resultant clones were co-transfected with the HIV-1 Tat expression plasmid pTatdsRed2 (Unwalla et al., 2004) into $4.0 \times 10^5$ U3-Luciferase indicator cells TZM-BI obtained through the NIH AIDS Research and Reference Reagent Program, Division of AIDS, NIAID, (Wei et al., 2002; Platt et al., 1998). Twenty-four and/or forty eight hours later luciferase expression was determined using the Dual-Luciferase® Reporter Assay System (Promega™) and a Veritas™ microplate luminometer from Turner Biosystems following the manufactures protocols.

Alpha-Amanatin Mediated Suppression of siRNA Induced TGS:

Chromatin immunoprecipitation was performed on $4.0 \times 10^6$ 293T transfected with siRNA EF52 or control CCR5 (10 nM using MPG 3 μl/ml of media) (Morris et al., 2004b). Twenty-four hours following MPG mediated siRNA transfection cultures ½ of the cultures were exposed to Alpha amanatin (0.05 μg/ml) and 24 hrs later collected and ChiP assay performed as described (Strahl-Bolsinger et al. 1997). Cultures were specifically probed with anti-dimethyl-Histone H3 (Lys9)(Upstate catalog #07-441 and -7-449 respectively). The final elutes were assayed using PCR 30 cycles of 94:55:72° C. and 15, 15 and 30 seconds respectively with primers 803 and 804 which specifically overlap the targeted EF1 alpha promoter (Morris et al., 2004a).

Example 8

Figures 6, 7A:
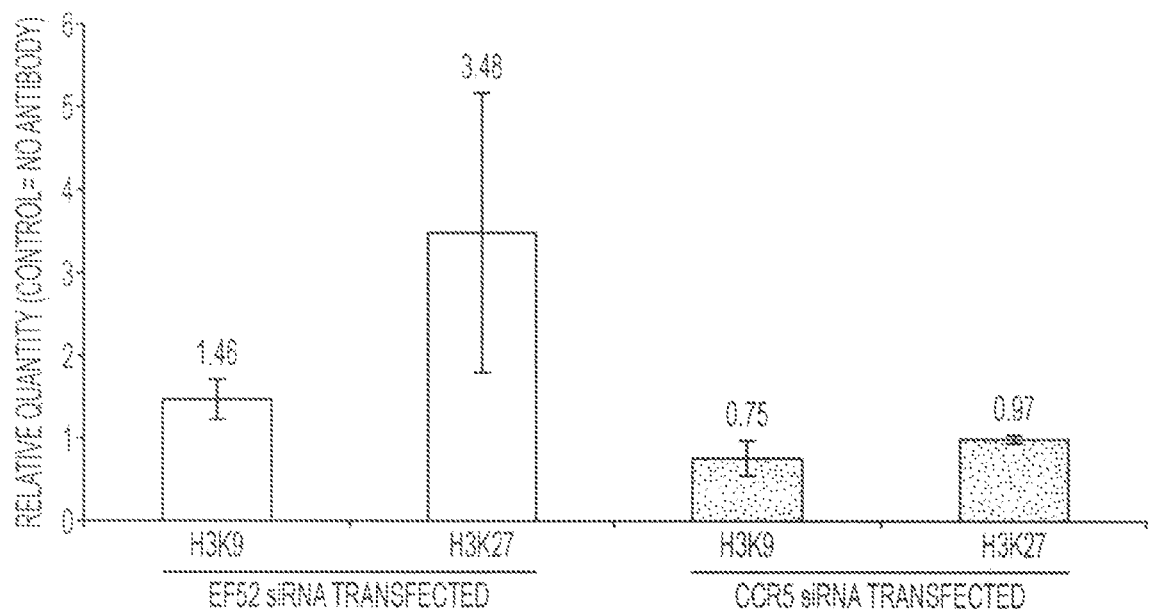
FIG. 6 shows the results of RNA down-regulation by shRNA directed against the RASSF1A promoter, as detected by transient transfections and quantitative PCR.
FIGS. 7A-7B show siRNA induced histone methylation.
Figure 7B:
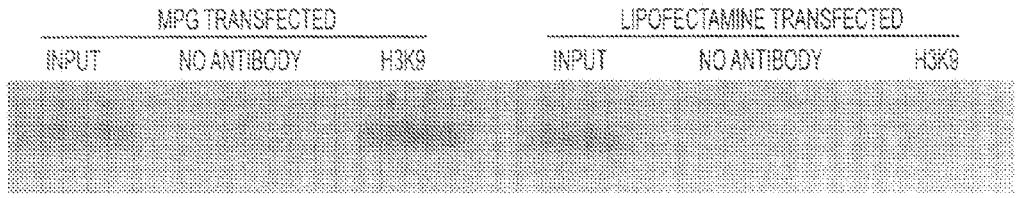

EF52 siRNA induces Histone Methylation siRNA EF52 is homologous to a sequence in the EF1A promoter and has been shown to induce TGS of endogenous EF1A (Morris et al., 2004b). The EF52 mediated TGS of endogenous EF1A was shown to involve both histone and DNA methylation. Moreover, silencing of promoters by DNA methylation has been shown to be preceded by histone methylation (Mutskov and Felsenfeld, 2004). To investigate the histone methyl mark induced by siRNA EF52 we transfected 293T cells with either EF52 or the control CCR5 siRNA (Morris et al., 2004b) using the nuclear specific peptide MPG (Morris et al., 2003; Morris et al., 1997). EF52 treated cultures exhibited a pronounced increase in H3K9 and H3K27 methylation relative to controls (FIG. 7A). Moreover, the induction of H3K9 methylation was contingent on nuclear specific delivery of the EF52 siRNA (FIG. 7B).

Example 9

EF52 siRNA Pulldown DNMT3A

Figure 8A:
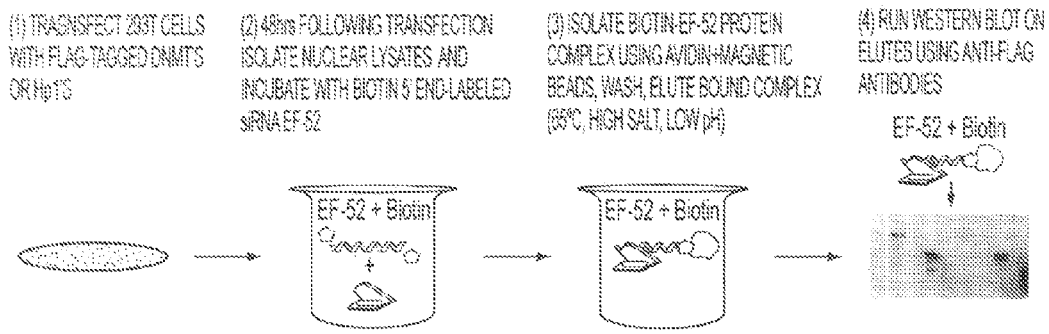
FIGS. 8A-8C show siRNA pulldown assays and their results.
Figure 8B:
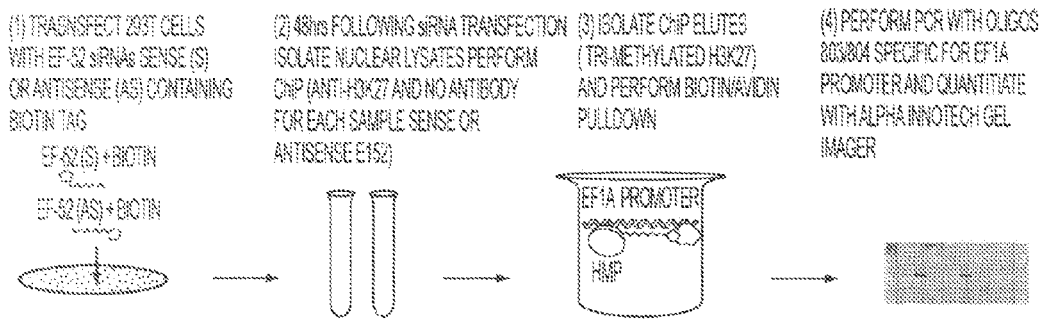

Transcriptional gene silencing by siRNAs in human cells involves some level of DNA methylation (Morris et al., 2004b; Kawasaki and Taira, 2004), indicating that DNA methyltransferases might be involved mechanistically in the observed silencing. To determine the mechanism underlying previously observed TGS in human cells we developed an siRNA pull-down assay (FIG. 8) and screened the binding potential of DNA methyltransferases (DNMT) 1, 3A, 3A2, 3B1, 3B2, and heterochromatin proteins (HP1-alpha, beta, and gamma) to the promoter targeted EF52 siRNAs (Table 1). Expression of each of the flag-tagged proteins was detected in the whole cell lysates with the exception of DNMT 3B1 and HP1-gamma, which had low to no expression (FIGS. 9A and 9B, respectively). Remarkably, when the whole cell lysates (FIGS. 9A-9B) were incubated in the presence of 5' biotin end labeled EF52 siRNA and the complexes pulled-down with avidin bound magnetic beads only DNMT 3A, 3A2 and 3B2 were eluted (FIG. 9C). While the control Prp2, Mock, and DNMT-1 (MT1) showed no binding to the EF52 biotin labeled siRNAs (FIGS. 9A-9C). The binding of DNMT3A was similar to previously reported findings of siRNAs binding in vitro to mouse DNMT3A (Jeffery and Nakielny, 2004).

Figures 9A, 9B:
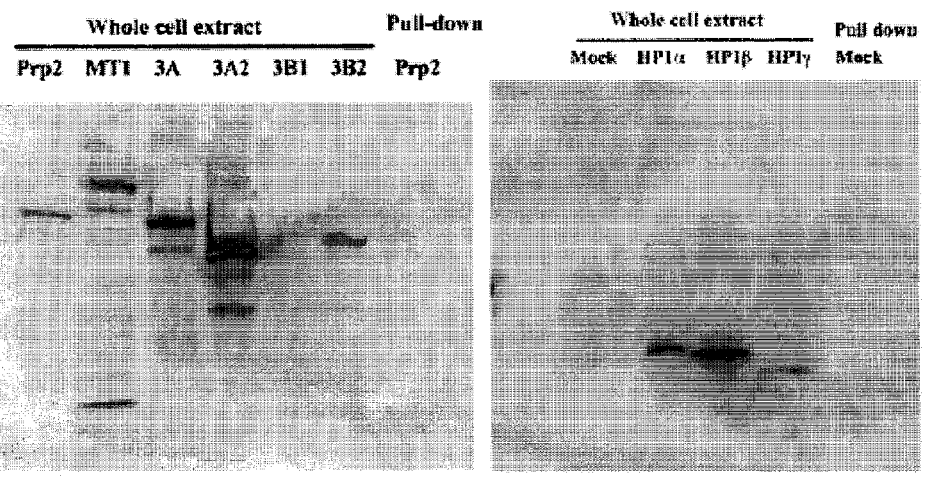
FIGS. 9A-9E show the expression of the flagged proteins.
Figure 9C:
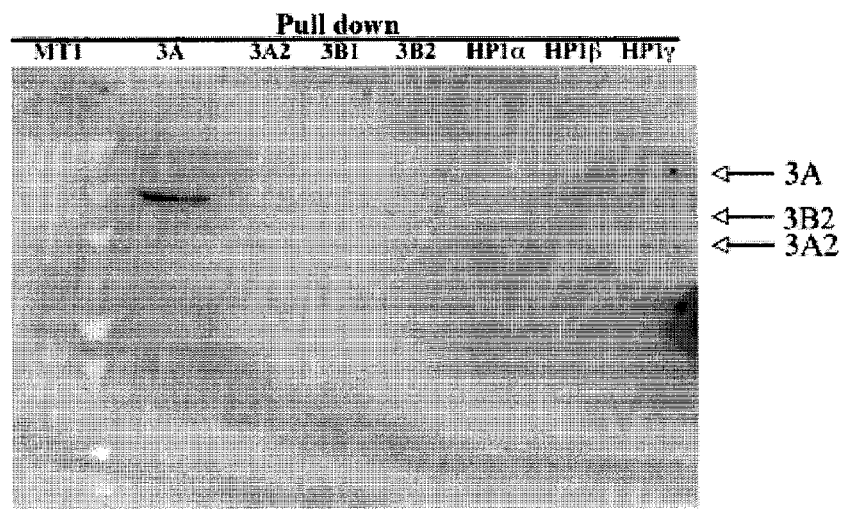
Figures 9D, 9E:
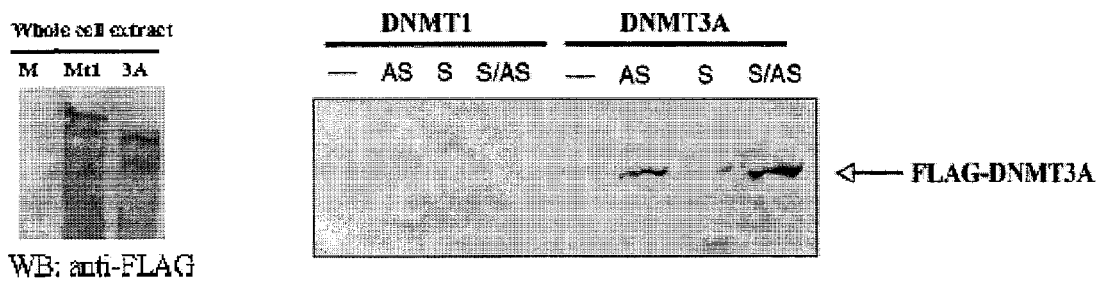
Figure 10:
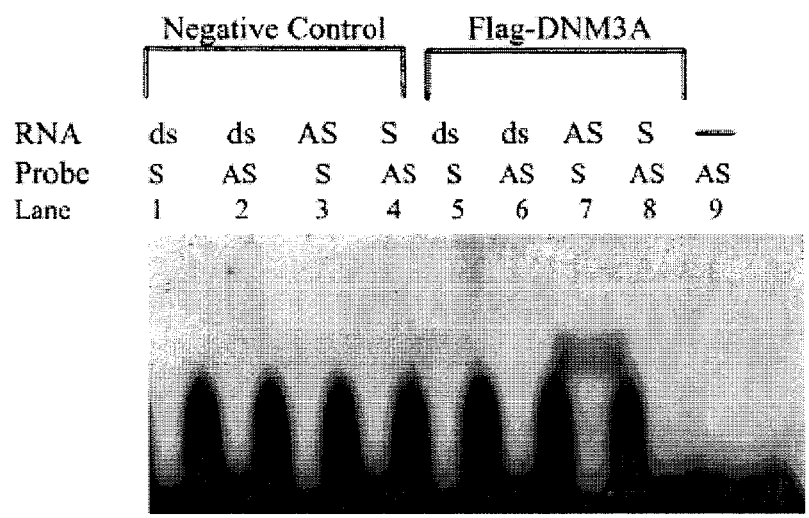
FIG. 10 shows detection of the antisense strand in flag-tag pulldowns. Flag-tagged DNMT3A and control (mock lysates alone) were incubated with 500 nM of siRNA EF52 and bound siRNA detected by binding of the radiolabelled probe to the respective target strand, sense or antisense. Results are representative of a single experiment.

Next we wanted to determine if there was any strand specificity in the DNMT3A/EF52 siRNA binding, as strand specific binding could be indicative of the underlying mechanism of siRNA mediated TGS. To determine the specificity of binding we incubated biotin 5' end labeled sense, antisense, sense/antisense and control non-biotin labeled sense/antisense siRNAs with DNMT1 and DNMT3A containing extracts (FIG. 9D). Interestingly, the antisense strand of EF52 showed significantly increased binding potential that was comparable to the biotin-sense/antisense treatment alone (FIG. 9E). A similar observation was gained by performing a DNMT-Flag immunoprecipitation followed by probing with radiolabelled siRNAs (sense or antisense) (FIG. 10). These data suggest that the antisense strand may direct the observed siRNA mediated TGS through interactions with DNMT3A.

TABLE 1

DNMTs and HP1s used in siRNA pull-down experiments.

| Flag-Tagged protein | Function |
|---|---|
| DNMT-1 (MT1) | Maintenance DNA methyltransferase, also involved in methylation during embryogenesis (8) |
| DNMT-3A | De novo methylation, involved in methylation during embryogenesis and transcriptional repression (8, 9) |
| DNMT-3A2 | De novo methyltransferase (8) |
| DNMT-3B1 | De novo methylation, involved in methylation during embryogenesis and transcriptional repression (8, 9) |
| DNMT-3B2 | Involved in methylation during embryogenesis (8) |
| HP1-alpha | Involved in transcriptional silencing by tethering DNA and bind core histones (10, 11) |
| HP1-beta | Involved in transcriptional silencing by tethering DNA and bind core histones (10, 11) |
| HP1-gamma | Involved in transcriptional silencing by tethering DNA and bind core histones (10, 11) |
| PRP2 | Negative control: RNA dependent RNA-ATpase (12, 13) |

All flag-tagged DNMTs were a gift from A. Riggs (COH/BRI), HP1 (alpha, beta, gamma) were a gift R. Losson, Institute de Genetique et de Biologic Moleculaire et Cellulaire, France, and PRP2 was a gift from R J Lin (COH/BRI).

Example 10

Histone Methylation and siRNA Specificity

Figure 11A:
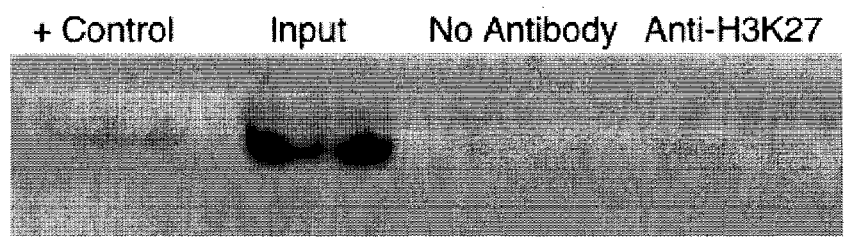
FIG. 11A-11E show analysis of siRNA and H3K27.

Unlike RNA interference, transcriptional silencing in mammalian cells is mediated by a combination of chromatin modifications that include histone deacetylation and cytosine DNA methylation (Bird and Wolffe, 1999). Silencing by EF52 siRNA was completely relieved by treating the cells with TSA and 5'-AzaC, drugs that inhibit histone deacetylases and DNA methyltransferases respectively (Morris et al., 2004b) and data presented here clearly shows H3K9 and H3K27 methylation is involved in the observed siRNA induced TGS of EF1A. To explore the link between histone 3 lysine methylation and siRNA specificity to the targeted promoter we performed a ChiP/RNA co-immunoprecipitation assay (as depicted in FIG. 8B). A ~4.8 fold increase in detectable EF52 targeted promoter relative to the no antibody control was observed in H3K27/antisense EF52 siRNA co-immunoprecipitates indicating H3K27, antisense siRNA EF52, and the targeted EF1A promoter EF1A co-localize in vivo (FIG. 11A). The observation(s) that 1) siRNAs bind DNMT3A (FIG. 9A-9D and Jeffery and Nakielny (2004)), 2) siRNA mediated TGS is reversible with the addition of both 5-AzaC and TSA (Morris et al., 2004b) and 3) Histone 3 lysine methylation (FIG. 7A) is present offers some clues to the underlying complex involved in siRNA mediated TGS in human cells.

Figure 8C:
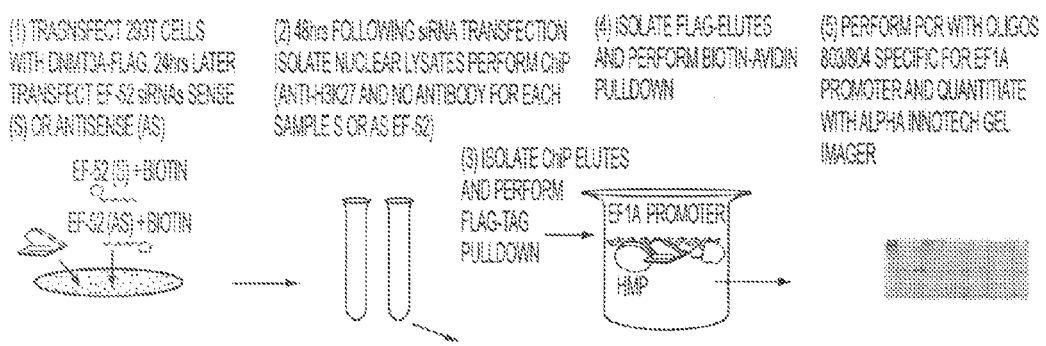
Figure 11B:
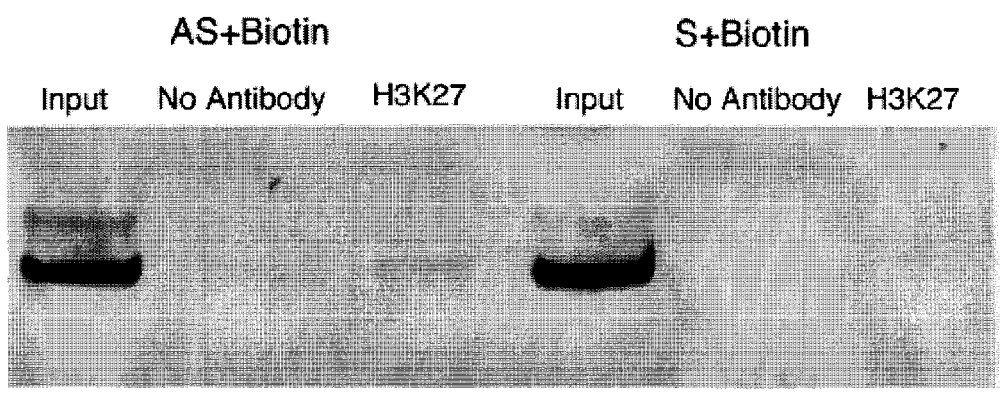
Figure 11C:
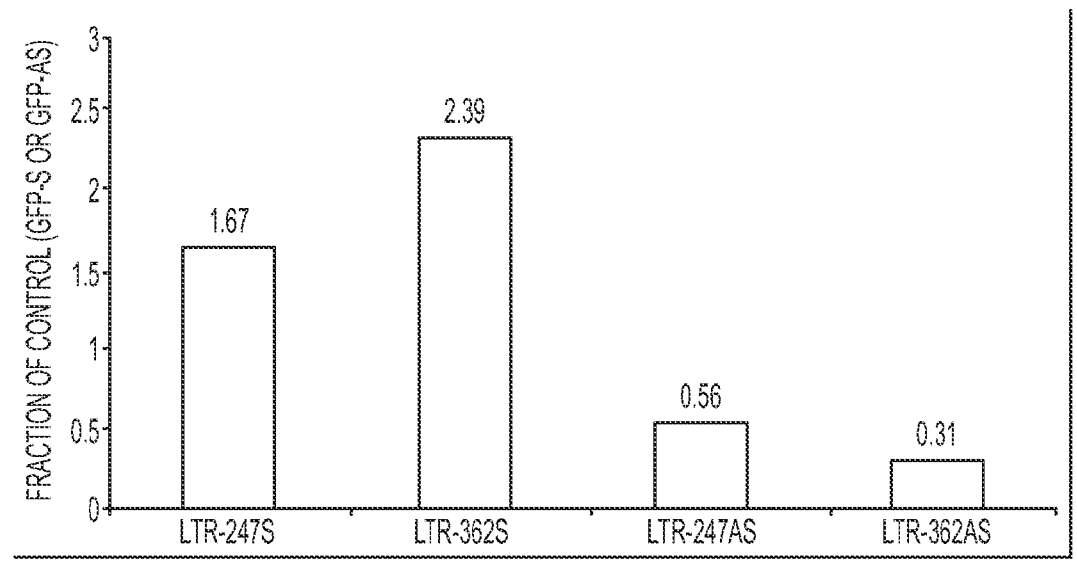
Figure 11D:
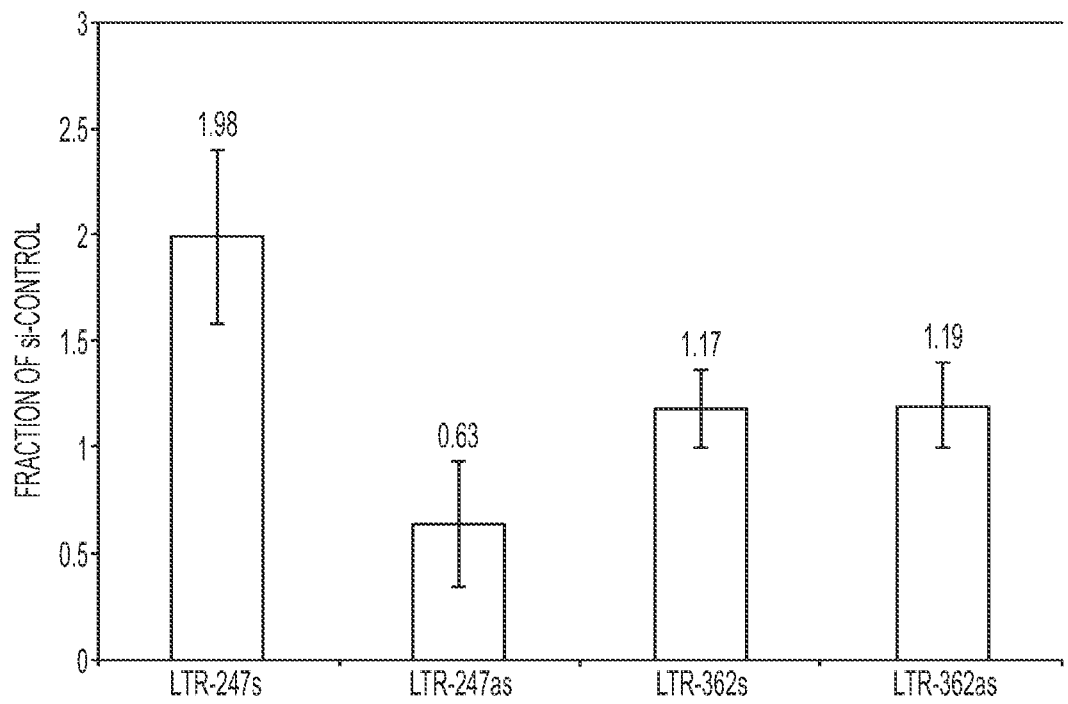

To investigate the core complex involved in siRNA EF52 mediated TGS we performed a triple-immunoprecipitation assay (as depicted in FIG. 8C). This assay consists of first a CHiP for H3K27 followed by a Flag-Tagged DNMT3A immunoprecipitation and then a siRNA biotin/avidin pull-down followed by a PCR for the targeted promoter in the final elute. Interestingly, the antisense EF52 strand was enriched ~2 and 3.5 fold relative to the no antibody and sense alone controls respectively (FIG. 11B). Notably the triple-immunoprecipitation was relatively inefficient with the antisense elute containing only ~7.6% of the control input (FIG. 11B).

Example 11

Antisense Strand of siRNA Directs TGS

Figure 11E:
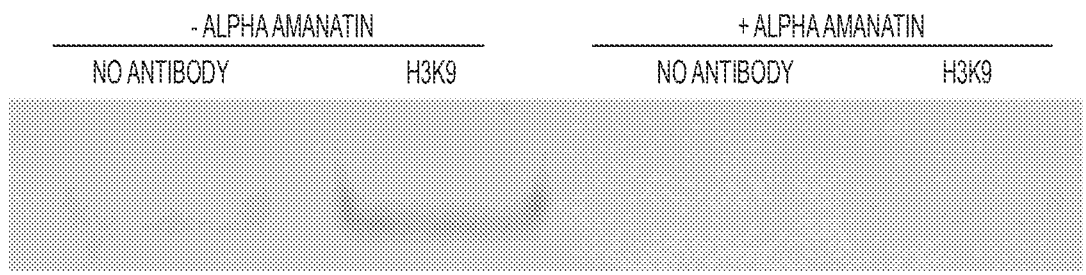

The observation that the antisense strand of the siRNA is preferentially detected in the co-immunoprecipitation assays suggest that the antisense can function alone to direct TGS. To determined if the antisense alone can direct TGS we designed plasmids expressing from the U6 promoter either the antisense, sense, or both sense/antisense targeting the U3 region of the HIV-1 LTR/promoter. Indeed, both U3 LTR specific siRNAs (Table 2) and remarkably, the antisense showed a profound and robust suppression of U3 expressed luciferase relative to controls in TZM-B1 cells (FIGS. 12 and 11E). However, while TZM-B1 cells contain an integrated lentiviral vector expressing luciferase from the HIV-1 LTR they also contain the 3' LTR (Wei et al., 2002). As such it is possible that some of the observed suppression was the result of the antisense siRNAs binding the 3' LTR and thus inhibiting luciferase expression in a PTGS based fashion. To determine if the antisense siRNAs can function to induce TGS we transfected 1G5 cells containing the LTR expressing the luciferase with an SV40 poly-A (Aguilar-Cordorva et al., 1994). Interestingly, only the antisense LTR-247 siRNA (Table 2) induced TGS (FIG. 11). These data clearly suggest that the antisense strand of the siRNA directs transcriptional silencing in human cells as well as suggest that fundamental differences in target site accessibility might also be present (i.e. LTR-362 overlaps the NF-kB binding site and LTR-247 does not, Table 2).

TABLE 2 siRNAs used in the HIV-1 U3 Targeting.

| siRNA (Position) | Sequence (Target) (SEQ ID NO:) | % GC |
|---|---|---|
| 247 (249-267 in LTR of HIV subtype B) | GTGTTAGAGTGGAGGTTTG (29) | 47.4 |
| 362 (354-372 in LTR of HIV subtype B) | CTTTCCGGTGGGGACTTTC (30) | 57.9 |
| 247c (249-267 in LTR of HIV subtype C) | GTATTAAAGTGGAAGTTTG (31) | 31.5 |
| 362c (354-372 in LTR of HIV subtype C) | CTTTCCACTGGGGCGTTCC (32) | 63.2 |
| GFP (108-126 in GFP mRNA) | CGATGCCACCTACGGCAAG (33) | 63.2 |
| R5 Control (787-805 in CCR5 mRNA) | TTCTTTGGCCTGAATAATT (34) | 31.6 |

Example 12

Transcription Required for siRNA Mediated TGS

The observation that the antisense strand of the siRNA is preferentially involved in siRNA mediated TGS suggest a mechanism that may be an antisense siRNA/RNA interaction (possibly non-coding RNA, personal communication R. Allshire) or an antisense siRNA/DNA interaction is present in the siRNA promoter targeting. The observation that only LTR-247 can mediate TGS of the U3 from HIV-1 LTR also supports a promoter accessibility or siRNA/DNA interaction. Regardless, both possibilities suggest that transcription may be required for the initiation of siRNA mediated TGS. To determine if transcription is required for siRNA mediated TGS we performed EF52 (treatment) or CCR5 (control) MPG mediated transfections and 24 hrs later treated ½ of the cultures with alpha amanatin (0.05 µg/ml) to inhibit RNA polymerase II (Pol-II) and then assayed for Histone 3 Lysine 9 methylation. Importantly, alpha amanatin treatment inhibited siRNA EF52 mediated Histone 3 Lysine 9 methylation (FIG. 11E) suggesting that RNA Pol-II mediated transcription is required for siRNA mediated TGS.

The initial discovery that promoter targeted siRNAs can induce gene silencing in human cells proved that small RNAs in mammals, *Drosophila, C. elegans* and plants can regulate gene expression by three conserved mechanisms: transcriptional gene silencing, mRNA degradation and translational inhibition. While there are many functional similarities between siRNA mediated TGS in mammals, *Drosophila, C. elegans* and plants the underlying mechanism may be somewhat varied. Data presented here suggests that the de novo DNA methyltransferase enzymes of the DNMT3 family are possibly guided by the small RNAs to the targeted promoter. The observation that DNMT-1 does not bind siRNA EF52 while DNMT3A and 3B (data not shown) do suggests that the de novo methyltransferases bind dsRNA independent of the DNA binding domain (Datta et al., 2003; Xie et al., 1999). Interestingly, DNMT3A has been shown to bind siRNAs (Jeffery and Nakielny, 2004) as well as associate with histone deacetylase 1 (HDAC1), the histone methyltransferase (Suv39H1), and HP1 (Fuks et al., 2003). Moreover, the observation that the antisense strand of EF52 preferentially binds DNMT3A and co-immunoprecipitates in vivo with DNMT3A, H3K27, and the targeted promoter and is efficacious in suppressing HIV-1 Tat induced U3 mediated transcription suggests a mechanism of action.

The emerging model for the mechanism of siRNA mediated TGS in human cells is proposed to operate temporally as: 1) the siRNA is either unwound and/or binds DNMT3A and then acted on by a helicase which then 2) allows the antisense strand to direct the DNMT3a to the targeted promoter leading ultimately to promoter site recognition. Next, 3) the DNMT3a/antisense siRNA complex may contain or then recruit HDAC-1 and Suv39H1 (Datta et al., 2003; Fuks et al., 2003; Fuks et al., 2001) which could 4) lead to the removal of the acetate and subsequent methylation of histone 3 lysine 9 and/or lysine 27 (Kawasaki and Taira, 2004) (FIG. 13). The result of H3K9 and/or H3K27 methylation is the suppression of the particular targeted genes expression (Mutskov and Felsenfeld, 2004; Bachman et al., 2001). Finally, if the gene silencing is re-enforced and positively selected for by the cell and it's local environment then DNA methylation and permanent silencing of the antisense siRNA targeted gene may ensue. Indeed HDAC-1, DNMT3a/siRNA and the NuRD chromatin remodeling complex (Jeffery and Nakielny, 2004; Datta et al., 2003; Zhang et al., 1999) can all be linked indicating one potential pathway to siRNA mediated TGS. Interestingly, the observation that there is strand specificity in the observed co-immunoprecipitations suggests two models for siRNA/promoter recognition; 1) there is an antisense siRNA and non-coding RNA interaction at the core of the targeting or 2) the unwinding of promoter DNA by RNA polymerase II allows for an antisense/DNA interaction to occur leading to promoter site recognition and subsequent silencing.

Short interfering RNAs (siRNAs) have been shown to silence genes at the transcriptional level in human cells (Morris et al., 2004b; Kawasaki and Taira, 2004; Kawasaki et al., 2005). Using human cells, we show that EF1A promoter-directed siRNA EF52 binds DNMT3A and directs histone methylation whereas controls do not. The binding of siRNA to DNMT3A was specific and showed a strand preference that co-immunoprecipitated with H3K27 and the targeted promoter. These results are the first demonstration that promoter directed siRNAs bind DNMT3A and co-localize to the targeted promoter and as such suggest a mechanism for siRNA mediated TGS in human cells. Importantly, the observation that siRNAs direct histone methylation and this effect is reversed by the inhibition of RNA Pol-II suggests that transcription is required for siRNA mediated TGS as well as that siRNAs may function to direct and/or write the histone code. Taken together these data propose that siRNAs mediate control of DNA in an RNA Pol-II mediated fashion through epigenetic modifications specifically involving histone 3 methylation and DNMT3A. These findings propose that dsRNA, specifically the antisense strand, plays a pivotal and underappreciated role in regulating the cell that could be conceptualized to be used therapeutically in treating virtually any ailment affecting humans.

Example 13

Materials and Methods for Examples 14-18

Cell Culture:

We sequestered a reporter system that contains the CCR5 promoter driving expression of a marker gene (red-shifted GFP). The vector pR5-GFPsg143 contains ~3 kb of CCR5 promoter, intron, and exons 1 and 2 (Guignard et al., 1998; Moriuchi et al., 1997; Mummidi et al., 1997) and drives the expression of red-shifted GFP (a gift from Dr. G. N. Pavlakis) (Rosati et al., 2001). A total of $4.0 \times 10^6$ 293T cells were transfected with vector pR5-GFPsg143 (5 µg, Lipofectamine 2000™) and neomycin-selected (800 µg/ml) to generate the stable cell population (293T CCR5-GFP). HeLa stable cells expressing RASSF1A promoter-specific shRNAs or control vector alone were previously generated in our lab (a gift from Dr. D. Castanotto) (Costanotto et al., 2005).

siRNA Screening:

To screen CCR5 promoter-specific siRNAs for knockdown of GFP expression, a total of $9.4 \times 10^5$ 293T CCR5-GFP cells were plated/well in a 12-well plate and 24 hrs later transfected with the respective promoter-specific siRNAs (Table 3) and the CCR5 mRNA control siRNA (10 nM) using MPG at a 10:1 charge ratio (MPG:siRNA), as described in Morris et al. (2004b) and Morris et al. (1997). The respective siRNAs were constructed from oligonucleotides following previously established methodologies for T7 expressed siRNA synthesis (Ambion Silencer™). 48 hrs post-transfection, cultures were collected for fluorescence activated cell sorting (FACS) analysis of GFP expression.

TABLE 3

| CCR5 Specific siRNAs | | | |
|---|---|---|---|
| R5-25 | 5'- | GCCAAAGCUUUUUAUUCUAaa-3' | (SEQ ID NO: 35) |
| | 3'-aaCGGUUUCGAAAAAUAAGAU | -5' | (SEQ ID NO: 36) |
| R5-61 | 5'- | GCCCAGAGGGCAUCUUGUGaa-3' | (SEQ ID NO: 37) |
| | 3'-aaCGGGUCUCCCGUAGAACAC | -5' | (SEQ ID NO: 38) |
| R5-149 | 5'- | CCGCCAAGAGAGCUUGAUAaa-3' | (SEQ ID NO: 39) |
| | 3'-aaGGCGGUUCUCUCGAACUAU | -5' | (SEQ ID NO: 40) |
| R5-854 | 5'- | GCCCGUAAAUAAACUUUCAaa-3' | (SEQ ID NO: 41) |
| | 3'-aaCGGGCAUUUAUUUGAAAGU | -5' | (SEQ ID NO: 42) |
| R5-Control | 5'- | AAUUCUUUGGCCUGAAUAAaa-3' | (SEQ ID NO: 43) |
| | 3'-aaUUAAGAAACCGGACUUAUU | -5' | (SEQ ID NO: 44) |

Chromatin Immunoprecipitation:

ChIP assays (Strahl-Bolsinger et al., 1997) were performed on $4.0 \times 10^6$ 293T CCR5-GFP cells transfected with 30 nM of synthetic (generated by IDT, Coralville, Iowa) R61 siRNA or control R5 siRNA using Lipofectamine 2000™. Treated cultures were formaldehyde cross-linked (1%, 10 min, room temp (R/T)) and then the reaction was stopped by adding glycine at a final concentration of 0.125M (10 min, R/T). The cells were then washed twice in 1×PBS+1/1000 PMSF (stock PMSF at 0.5M), resuspended in 600 µl of ChIP lysis buffer (50 mM HEPES pH 7.5, 140 mM NaCl, 10% Triton X100, 0.1% NaD, 1/1000 PMSF) and incubated on ice (10 min). Next, the samples were centrifuged (5,000 rpm, 5 min, 4° C.), resuspended in 600 µl ChIP lysis buffer, incubated on ice (10 min) and then sonicated (Branson 50 cell machine, 6 intervals with 20 second pulses and 2 min rests). The sonicated samples were then centrifuged (14,000 rpm, 10 min, 4° C.) and the supernatants removed and pre-cleared with 30 µl protein A/Salmon Sperm (Upstate, Charlottesville, Va., catalog #16-157) (15 min, 4° C., rotating platform). The pre-cleared supernatants were then centrifuged (14,000 rpm, 5 min, 4° C.) and supernatants removed and divided into equivalent aliquots. The partitioned samples were incubated with no antibody (control), anti-H3K9$^{me2+}$ (Upstate catalog #07-441), anti-Ago1 (Upstate catalog #07-599), anti-RNAPII (Abcam, Cambridge, Mass., catalog #ab817), anti-H3K27$^{me3+}$ (Upstate catalog #07-449), anti-TRBP antiserum (a gift from Dr. A. Gatignol) (Duarte et al., 2000), and anti-Ago2 (Upstate catalog #07-590) (3 hrs to overnight, 4° C., rotating platform). The samples were then treated with 10 µl Protein A/Salmon Sperm (Upstate), (15 min, R/T, rotating platform), pulled-down (10,000 rpm, 1 min, 4° C.), and washed. The no antibody control supernatants were saved and used as input controls. The washes consisted of 2 washes with 1 ml of ChIP lysis buffer, 2 washes with 1 ml ChIP lysis buffer high salt (50 mM HEPES pH 7.5, 500 mM NaCl, 1% Triton X100, 0.1% NaD, 1/1000 PMSF), followed by 2 washes with 1 ml ChIP wash buffer (10 mM Tris pH 8.0, 250 mM LiCl, 0.5% NP-40, 0.5% NaD, 1 mM EDTA). For each wash the samples were incubated (3 min, R/T, rotating platform), followed by centrifugation (14,000 rpm, 3 min, R/T). After the final wash the complexes were eluted by two treatments of 100 µl elution buffer (50 mM Tris pH 8.0, 1% SDS, 10 mM EDTA) (10 min, 65° C.), followed by centrifugation (14,000 rpm, 3 min, R/T). The eluted complexes along with the initial aliquot used in the no antibody control (200 µl) were then reverse cross-linked by adding 1 µl RNase A (10 mg/ml) and 20 µl of 5M NaCl to each sample and incubated (4-6 hrs, 65° C.). The reverse cross-linked samples were then treated (10 µl of 0.5M EDTA, 20 µl of 1M Tris-HCl pH 6.5, 2 µl of 10 mg/ml Proteinase K) (1 hr, 45° C.) and the DNA recovered by Phenol/Chloroform extraction and assayed using real-time PCR (40 cycles of 94:55:72° C. at 30:30:30 seconds) with primers 5' chip-2 5'-GGG GTC TCA TTT GCC TTC TTA GAG ATC ACA-3' (SEQ ID NO:45) and 3' chip-3 5'-TAA GTA TAT GGT CAA GTT CAG GTT C-3' (SEQ ID NO:46) that specifically overlap the CCR5 promoter R61 siRNA target site, standardized to plasmid pR5-GFPsg143, and normalized to input values. To determine the extent of Ago1 and H3K9$^{me2+}$ spreading, primers 5' walk-1 5'-GTC TTC TCA GCT CTG CTG ACA ATA CT-3' (SEQ ID NO:47) and 3' walk-2 5'-GGA TTT TCA CTC TGT TCA CTA TTT TGT TGC-3' (SEQ ID NO:48) that overlap a region ~100 to 300 by downstream of the CCR5 promoter R61 siRNA target site were used. For RASSF1A promoter ChIP experiments, primers 5' ras-1 5'-GAA GGA AGG GCA AGG CGG GGG GGG CTC TGC-3' (SEQ ID NO:49) and 3' ras-1 5'-GGC CCG GTT GGG CCC GTG CTT CGC T-3' (SEQ ID NO:50) were used.

qRT-PCR Amplification:

SuperScript™ III Platinum SYBR Green One-Step qRT-PCR kit (Invitrogen, Carlsbad, Calif.) was used to amplify GFP, RASSF1A, and GAPDH transcript levels from total RNA isolated with RNA STAT-60™ (Tel-Test, Friendswood, Tex.), using GFP and GAPDH primers as previously described (Morris et al., 2004b). RASSF1A primers used were URF1A 5'-TGG TGC GAC CTC TGT GGC GAC TT-3' (SEQ ID NO:51) and RT4 5'-GAT GAA GCC TGT GTA AGA ACC GTC CT-3' (SEQ ID NO:52) as previously described (Costanotto et al., 2005).

Western Analysis and RNase Treatment:

Total protein from 293T CCR5-GFP whole cell extracts, anti-RNAPII (Abcam, Cambridge, Mass., catalog #ab817) immunoprecipitates, anti-RNAPII immunoprecipitates from cell extracts treated for 30 min in 50 µg/ml RNase A (Sigma, St. Louis, Mo.) at 25° C., and extracts from Ago1 siRNA treated [Ago1(−)] or control R5 siRNA treated [Ago1(+)] 293T CCR5-GFP cells were heated (5 min, 95° C.), separated by electrophoresis in 4-12% SDS polyacrylamide electrophoresis, transferred to PVDF membranes, probed with anti-Ago1 (Upstate catalog #07-599), and developed with anti-rabbit horseradish peroxidase-labelled antibodies (Amersham Biosciences, Pittsburgh, Pa.) and Luminol detection reagent (Fisher, Hampton, N.H.).

Promoter Methylation Analysis:

Genomic DNA was digested for 1 hour with Ava I (New England Biolabs, Ipswich, Mass.) or Apa I (New England Biolabs) at 37° C. for R61 or R5 control siRNA treated 293T CCR5-GFP cells or RASSF1A shRNA or control vector expressing HeLa stable cells, respectively and used as templates for promoter specific real-time PCR (40 cycles of 94:55:72° C. at 30:30:30 seconds) with ChIP primers for the CCR5 and RASSF1A promoters. PCR amplification indicates that the Ava I or Apa I sites within the targeted promoter sequences are methylated and as such protected from enzyme digestion. All values were normalized to equivalent amounts of undigested genomic DNA samples incubated in NEBuffer #4 alone.

Example 14 siRNA Mediated Silencing of CCR5 Promoter

To measure the levels of siRNA mediated silencing at the targeted CCR5 promoter, we generated a stable cell line expressing CCR5 promoter-driven green fluorescent protein (293T CCR5-GFP). Four candidate siRNAs with sequence homology to the CCR5-GFP promoter (Table 3) were screened for inhibition of GFP expression at 48 hrs post-siRNA transfection, with two siRNAs (R61 and R149) showing ~50% reduction of protein levels (FIG. 14). GFP mRNA levels were measured at 24 hrs post-siRNA transfection using real-time quantitative RT-PCR (qRT-PCR) and normalized to GAPDH levels. In cells treated with promoter-specific R61 siRNA, we observed ~69% knockdown of GFP mRNA transcript levels when compared to R5 control siRNA (CCR5 mRNA-specific) transfected cells (FIG. 15A), similar to previous observations with siRNAs targeted to RNAPII promoters (Morris et al., 2004b; Weinberg et al., 2006; Ting et al., 2005). Furthermore, we examined siRNA mediated TGS at the endogenous RASSF1A promoter using HeLa cell lines stably expressing a short hairpin RNA (shRNA) targeted to the RASSF1A promoter or a control vector not expressing an shRNA (Castanotto et al., 2005). RASSF1A mRNA transcript levels exhibited ~74% knockdown by promoter-targeted shRNAs in this constitutively expressed setting (FIG. 15A).

Example 15 siRNA Mediated Induction of Silent Histone Modifications

Previous work has shown that siRNA mediated TGS correlates with silent histone methylation marks, and H3K9$^{me2+}$ and H3K27$^{me3+}$ have been found to associate with siRNA targeted promoters (Weinberg et al., 2006; Ting et al., 2005). To determine whether the CCR5 promoter-specific R61 siRNA could induce silent histone modifications, we screened the CCR5-GFP promoter specifically at regions overlapping the R61 siRNA target site using chromatin immunoprecipitation (ChIP) for H3K9$^{me2+}$. A ~14-fold enrichment of H3K9$^{me2+}$ was observed at 24 hrs post-R61 siRNA transfection, relative to R5 control siRNA transfected cells (FIG. 15B) and consistent with previously observed epigenetic modifications (Weinberg et al., 2006; Ting et al., 2005). To test whether spreading of H3K9$^{me2+}$ to adjacent nucleosomes was occurring, we performed ChIP experiments using PCR primers spanning a region ~100 to 300 bp downstream of the R61 siRNA target site. A ~7-fold enrichment of H3K9$^{me2+}$ was observed downstream of the promoter target site (FIG. 15B). Time-course ChIPs of the CCR5-GFP promoter showed an increase in H3K9$^{me2+}$ at the targeted promoter between 12 and 24 hrs post-siRNA transfection (FIG. 15C). However, only a negligible amount of DNA methylation was observed at the targeted CCR5-GFP promoter, while a slight increase in DNA methylation occurred when constitutively expressed shRNAs were targeted to the RASSF1A promoter (FIG. 16).

Example 16

Contribution of Ago1 or Ago2 to siRNA Mediated Promoter Silencing

We next investigated whether Ago1 or Ago2 might contribute to siRNA mediated promoter silencing, as Ago1 directs the induction and spreading of H3K9$^{me2+}$ and TGS in S. Pombe (Verdel et al., 2004; Noma et al., 2004), and Ago2 is a component of the well-characterized RNA-induced silencing complex (RISC) in human cells (Liu et al., 2004). ChIP experiments in 293T CCR5-GFP cells transfected with R61 or R5 control siRNAs showed an ~18-fold enrichment of Ago1 at the CCR5-GFP promoter in R61 siRNA transfected cells (FIG. 17A). Interestingly, a ~14-fold enrichment of Ago1 downstream of the R61 target site was also observed (FIG. 17A), suggesting that spreading of Ago1 may direct and/or associate with downstream histone modifications, leading to the spreading of TGS along the targeted gene. Additionally, Ago1 was also enriched at the shRNA-targeted endogenous RASSF1A promoter (FIG. 17A). We did not, however, observe enrichment of Ago2 in our ChIP experiments in 293T CCR5-GFP cells transfected with R61 or R5 control siRNAs (FIG. 18). To determine the temporal nature of Ago1 association with siRNA targeted promoters, time-course ChIPs were conducted at 6 hr intervals from 12 to 30 hrs post-siRNA transfection in 293T CCR5-GFP cells. The time-course ChIP experiments demonstrated a transient association between Ago1 and the targeted promoter (FIG. 17B), correlating with a concomitant increase in H3K9$^{me2+}$ (FIG. 15C). These data suggest that Ago1 directs siRNA mediated TGS of RNAPII promoters and acts upstream of the histone modification pathway.

Recent reports in S. Pombe (Kato et al., 2005) and in human cells (Weinberg et al., 2006) have also demonstrated that RNAPII is required for siRNA mediated TGS. To determine whether RNAPII associates with Ago1, we performed co-immunoprecipitations from 293T CCR5-GFP cell extracts and found that Ago1 co-immunoprecipitated with RNAPII (FIG. 17C). To test whether this association between Ago1 and RNAPII was via a single-stranded RNA intermediate that is transcribed through promoter regions, 293T CCR5-GFP cell extracts were treated with RNase A. RNase A treatment had no effect on the ability of RNAPII to co-immunoprecipitate Ago1 (FIG. 17C), suggesting a direct protein-protein interaction between an Ago1-containing transcriptional silencing complex and RNAPII.

Example 17

RNAi Mediated Knockdown of Ago1

RNAi mediated knockdown of Ago1 was next used to investigate the requirement of Ago1 in directing di-methylation of H3K9 and silencing gene expression. 293T CCR5-GFP cells were transfected with a validated, Ago1 mRNA-specific siRNA (Meister et al., 2004), and knockdown of Ago1 expression was determined at 48 hrs post-Ago1 siRNA transfection (FIG. 19A). Ago1 siRNA treated cells [Ago1(−)] or R5 control siRNA treated cells [Ago1(+)] were transfected with promoter-specific R61 siRNAs at 24 hrs following the Ago1 siRNA or R5 control siRNA transfections. GFP transcript levels were markedly elevated in Ago1(−) cells at 24 hrs post-R61 siRNA transfection, relative to R61-transfected Ago1 (+) cells which exhibited typical levels of Ago1 expression (FIG. 19B). Knockdown of Ago1 resulted in the loss of Ago1 binding at the targeted CCR5-GFP promoter in ChIP experiments, which also correlated with a noticeable reduction in the levels of H3K9$^{me2+}$ (FIG. 19C). These data indicate that Ago1 localization to the targeted promoter region is required for H3K9 di-methylation and siRNA mediated TGS in human cells.

Example 18

ChIP Analysis of Endogenous CCR5 Promoter

Evaluation of the endogenous CCR5 promoter in HEK 293 and HeLa cells through ChIP experiments revealed that Ago1 also localized to the epigenetically silenced CCR5 promoter in both cell types (FIGS. 20A and 20B). Ago2 was not observed in HEK 293 cells in our ChIP experiments of the endogenous CCR5 promoter (FIG. 18), analogous to our Ago2 ChIP data at the siRNA targeted CCR5-GFP promoter in 293T CCR5-GFP cells. Supporting our observation that RNAPII co-immunoprecipitates with Ago1 at epigenetically silenced promoters, RNAPII was also present at the silenced CCR5 promoters in both HEK 293 and HeLa cells, as determined by ChIP (FIGS. 20A and 20B). These data suggest that low levels of RNAPII transcription of endogenously silenced promoters are required to maintain an epigenetically silent state. Enrichment of H3K27$^{me3+}$ was observed at the endogenous CCR5 promoters in both cell types (FIGS. 20A and 20B), indicating the presence of a histone mark that is known to recruit the PcG repressor proteins to regions of facultative heterochromatin.

A recently characterized component of the RNAi machinery is the HIV-1 TAR RNA-binding protein 2 (TRBP2), a double-stranded RNA-binding protein that has been shown to be a component of the effector complex RISC (Forstemann et al., 2005; Gatignol et al., 2005; Gregory et al., 2005; Haase et al., 2005; Lee et al., 2006). We sought to determine whether TRBP2 might also be associated with Ago1 in a nuclear transcriptional silencing complex. We utilized anti-TRBP2 antiserum (kindly supplied by A. Gatignol) to perform ChIPs of the CCR5 and RASSF1A promoters in HeLa cells. TRBP2 was enriched at the endogenous CCR5 promoter in HeLa cells at levels similar to Ago1 enrichment (~5.23 and ~5.59-fold enrichment, respectively) (FIGS. 20B and 20C), suggesting a nuclear transcriptional silencing complex composed of Ago1 and TRBP2. Furthermore, TRBP2 localized to the shRNA-targeted and Ago1 enriched RASSF1A promoter (FIG. 20C). These findings suggest an endogenous mechanism of transcriptional regulation involving several components of the RNAi machinery, RNAPII transcription, and Polycomb group proteins, all of which may act in concert to mediate formation and maintenance of facultative heterochromatin.

The current paradigm for the mechanism of TGS in human cells involves H3K9, H3K27, and DNA methylation at the siRNA targeted promoters (Morris et al., 2004b; Castanotto et al., 2005; Buhler et al., 2005; Janowski et al., 2005; Zhang et al., 2005; Suzuki et al., 2005), although the requirement of DNA methylation for TGS in human cells is still uncertain (Ting et al., 2005; Janowski et al., 2005; Park et al., 2004; Svoboda et al., 2004) and may possibly be promoter-dependent. Data presented here reveal that Ago1 directs siRNA mediated TGS by associating with targeted promoters through an interaction with RNAPII. The finding that Ago1 is required for siRNA mediated promoter silencing and H3K9$^{me2+}$, coupled with the observation that transient association of Ago1 at the targeted promoter corresponds with an increase in H3K9$^{me2+}$, suggests that Ago1 functions upstream of chromatin modifications that silence gene expression by recruiting specific histone methyltransferases such as G9a (H3K9$^{me2+}$) and/or EZH2 (H3K27$^{me3+}$) (Vire et al., 2006).

Along with previously published observations (Morris et al., 2004b; Weinberg et al., 2006; Ting et al., 200; Buhler et al., 2005; Suzuki et al., 2005), the findings presented here suggest a putative model for siRNA mediated TGS in human cells involving a transcriptional silencing complex (TSC) containing Ago1, TRBP2, siRNA, and possibly chromatin remodeling factors (i.e. HDAC-1, G9a, EZH2, DNMT3a) (Weinberg et al., 2006; Morris et al., 2005) (FIG. 21). The TSC may be directed by siRNAs to their target promoters in an RNAPII-dependent manner (Weinberg et al., 2005), and the observation here that Ago1 associates with RNAPII suggests that RNAPII may provide a docking site for the TSC. Upon siRNA loading into the TSC, the antisense strand (Weinberg et al., 2006) may guide the TSC to a low copy promoter-specific RNA that corresponds to the siRNA targeted promoter (manuscript in preparation: Han, Kim, Rossi, Morris). This would allow for the formation of an RNA:RNA duplex between the antisense strand of the siRNA and either a nascent low copy promoter-specific RNA while it is being transcribed or a low copy promoter-specific RNA that is already a component of the local chromatin structure (Maison et al., 2002). Recognition of the siRNA target site would potentially stall the low copy promoter-specific RNA-scanning TSC:RNAPII complex and initiate the formation of facultative heterochromatin by recruiting histone methyltransferases and possibly PcG repressor complexes, which have recently been linked to Ago1 and the RNAi machinery in *Drosophila* (Grimaud et al., 2006). The inclusion of TRBP2 in the TSC suggests a potentially important role for this protein in Ago1 mediated RNA binding.

An alternative model implicated by the observed spreading of TGS and facultative heterochromatin from a promoter nucleation site would involve the siRNA antisense strand-directed TSC:RNAPII complex moving along the targeted RNAPII-transcribed promoter/gene, potentially modifying the H3 histones as they are reconstituted into nucleosomes immediately following transcription. Both of these models, or an amalgamation of the two, would necessitate the involvement of RNAPII, which is consistent with recent evidence that RNAPII function is required for histone methylation and TGS at siRNA-targeted promoters in human cells (Weinberg et al., 2006) and in *S. Pombe* (Kato et al., 2005), suggesting an Ago1 and RNAPII-dependent mechanism of transcriptional silencing that is evolutionarily conserved. Additionally, the recent discovery and characterization of a vast array of small (21- to 26-nt), non-coding RNAs is changing the classical understanding of gene regulation (Katayama et al., 2005), and taken together with the data presented here, suggests that these non-coding RNAs may play a more profound role in writing the histone code (Jenuwein and Allis, 2001) and regulating gene expression at the level of DNA.

Example 19

Additional Data Supporting Ago1 Involvement

We have generated new data that further supports the connection between Argonaute 1 directed transcriptional gene silencing (TGS) and Polycomb group mediated epigenetic silencing in human cells. We have performed chromatin immunoprecipitations in HeLa cells with a recently acquired antibody (Upstate) against the H3K27$^{me3+}$ histone methyltransferase and Polycomb group protein EZH2. Our ChIP data shows enrichment of EZH2 at the shRNA-targeted RASSF1A promoter (FIG. 22), suggesting that an Ago1 containing transcriptional silencing complex (TSC) may recruit EZH2 to epigenetically silence the targeted RASSF1A promoter. Furthermore, EZH2 was also found to be enriched at the endogenously silenced CCR5 promoter (FIG. 22), which we previously demonstrated was also enriched for Ago1 (FIG. 20B), suggesting that Ago1 is involved in the mechanism of endogenous epigenetic silencing at regions of facultative heterochromatin. Recent genome-wide mapping for Polycomb components in human cells has also shown that CCR5 is a Polycomb target gene (Bracken et al., 2006).

Additionally, the low levels of DNA methylation that we have observed at the shRNA-targeted RASSF1A promoter (FIG. 14; Castanotto et al. 2005) may result from the recruitment of DNMT3a, shown to associate with promoter-targeting siRNA (Weinberg et al., 2006), by EZH2, which has recently been shown to recruit DNMT3a (Vire et al., 2005).

We also performed ChIPs in HeLa cells of the human Polycomb target promoter MYT1 (Kirmizis et al., 2004) and found enrichment of Ago1, EZH2, and H3K27$^{me3+}$ at this epigenetically silenced promoter (FIG. 23). Collectively, these data provide additional evidence in support of the connection between RNAi and Polycomb silencing in human cells.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

E. Aguilar-Cordova, E. (1994). A sensitive reporter cell line for HIV-1 tat activity, HIV-1 inhibitors, and T cell activation effects. *AIDS Res Hum Retroviruses* 10:295-301.

Amarzguioui, M. et al. (2003). Tolerance for Mutation and Chemical Modifications in a siRNA. *Nucleic Acids Research* 31:589-595.

Bachman, K. E. et al. (2001). Dnmt3a and Dnmt3b are transcriptional repressors that exhibit unique localization properties to heterochromatin. *J Biol Chem* 276:32282-32287.

Bernstein, E. et al. (2001) Role for a bidentate ribonuclease in the initiation step of RNA interference. *Nature* 409:363-366.

Bertrand, E. et al. (1997). The expression cassette determines the functional activity of ribozymes in mammalian cells by controlling their intracellular localization. *RNA* 3:75-88.

Bird, A. P. and Wolffe, A. P. (1999). Methylation-induced repression—belts, braces, and chromatin. *Cell* 99:451-454

Bracken, A. P. and N. Dietrich, et al. (2006). "Genome-wide mapping of Polycomb target genes unravels their roles in cell fate transitions." *Genes Dev* 20(9):1123-1136.

Brummelkamp, T. R. et al. (2002). A system for stable expression of short interfering RNAs in mammalian cells. *Science* 296(5567):550-553.

Castanotto, D. et al. (2005). "Short hairpin RNA-directed cytosine (CpG) methylation of the RASSF1A gene promoter in HeLa cells." *Mol Ther* 12(1):179-183.

Chan, S. W. et al. (2004). RNA silencing genes control de novo DNA methylation. *Science* 303:1336.

Datta, J. (2003). Biochemical fractionation reveals association of DNA methyltransferase (Dnmt) 3b with Dnmt1 and that of Dnmt 3a with a histone H3 methyltransferase and Hdac1. *J Cell Biochem* 88:855-864.

Duarte, M. et al. (2000). Characterization of TRBP1 and TRBP2. Stable stem-loop structure at the 5' end of TRBP2 mRNA resembles HIV-1 TAR and is not found in its processed pseudogene. *J Biomed Sci* 7:494-506.

Eckstein, F. (2000). Phosphorothioate oligodeoxynucleotides: what is their origin and what is unique about them? *Antisense Nucleic Acid Drug Dev* 10:117-21.

Elbashir, S. M. et al. (2001a). Duplexes of 21-nucleotide RNAs mediate RNA interference in cultured mammalian cells. *Nature* 411:494-498.

Elbashir, S. M. et al. (2001b). RNA interference is mediated by 21- and 22-nucleotide RNAs. *Genes & Dev* 15:188-200.

Fuks, F. et al. (2001). Dnmt3a binds deacetylases and is recruited by a sequence-specific repressor to silence transcription. *EMBO J* 20:2536-2544.

Fuks, F. et al. (2003). The DNA methyltransferases associate with HP1 and the SUV39H1 histone methyltransferase. *Nucleic Acids Res* 31:2305-2312.

Good, P. D. et al. (1997). Expression of small, therapeutic RNAs in human cell nuclei. *Gene Ther* 4:45-54.

Guignard, F. et al. (1998). Gene organization and promoter function for CC chemokine receptor 5 (CCR5). *J Immunol* 160:985-992.

Hamilton, A. et al. (2002). Two classes of short interfering RNA in RNA silencing. *EMBO J* 21:4671-4679.

Hammond, S. M., et al. (2001). Argonaute2, a link between genetic and biochemical analyses of RNAi. *Science* 293 (5532):1146-1150.

Harborth, J. et al. (2003). Sequence, chemical, and structural variation of small interfering RNAs and short hairpin RNAs and the effect on mammalian gene silencing. *Antisense Nucleic Acid Drug Dev* 13:83-105.

Heidel, J. D. et al. (2004). Lack of interferon response in animals to naked siRNAs. *Nat Biotechnol* 22:1579-1582.

Herdewijn, P. (2000). Heterocyclic modifications of oligonucleotides and antisense technology. *Antisense Nucleic Acid Drug Dev* 10:297-310.

Holen, T. et al. (2002). Positional effects of short interfering RNAs targeting the human coagulation trigger tissue factor. *Nucleic Acids Res* 30:1757-1766.

Hornung, V. et al. (2005). Sequence-specific potent induction of IFN-alpha by short interfering RNA in plasmacytoid dendritic cells through TLR7. *Nature Med* 11:263-270.

Hu-Lieskovan, S. et al. (2005). Sequence-specific knockdown of EWS-FLI1 by targeted, non-viral delivery of siRNA inhibits tumor growth in a murine model of metastatic Ewing's sarcoma. *Cancer Res* 65(19):8984-92.

Jeffery, L. and Nakielny, S. (2004). Components of the DNA methylation system of chromatin control are RNA-binding proteins. *J Biol Chem* 279:49479-49487.

Jones, L. et al. (2001). RNA-directec transcriptional gene silencing in plants can be inherited independently of the RNA trigger and requires Met1 for maintenance. *Cur Biol* 11:747-757.

Judge, A. D. et al. (2005). Sequence-dependent stimulation of the mammalian innate immune response by synthetic siRNA. *Nat Biotechnol* 23:457-462.

Kawasaki, H. and Taira, K. (2004). Induction of DNA methylation and gene silencing by short interfering RNAs in human cells. *Nature* 431:211-217.

Kawasaki, H., et al. (2005). siRNA induced transcriptional gene silencing in mammalian cells. *Cell Cycle* 4:442-448.

Ketting, R. F. et al. (2001). Dicer functions of RNA interference and in synthesis of small RNA involved in developmental timing in C. elegans. *Genes Dev* 15(20):2654-2659.

Kim, D. H. et al. (2005). Synthetic dsRNA Dicer substrates enhance RNAi potency and efficacy. *Nat Biotechnol* 23:222-226.

Kim, E.-J. et al. (2005). IFI16 Is an Essential Mediateor of Growth Inhibition, but Not Differentiation, Induced by the Leukemia Inhibitory Factor/JAK/Stat Pathway in Medullary Thyroid Carcinoma Cells. *J Biol Chem* 280(6):4913-4920.

Kirmizis, A. et al. (2004). "Silencing of human polycomb target genes is associated with methylation of histone H3 Lys 27." *Genes Dev* 18(13):1592-605.

Kreuter, J. (1991). Nanoparticles-preparation and applications. In: *Microcapsules and nanoparticles in medicine and pharmacy*, Donbrow M., ed, CRC Press, Boca Raton, Fla., pp. 125-14.

Lee, N. S. et al. (2002). Expression of small interfering RNAs targeted against HIV-1 rev transcripts in human cells. *Nature Biotechnology* 19:500505-.

Lee, Y. S. et al. (2004). Distinct roles for *Drosophila* Dicer-1 and Dicer-2 in the siRNA/miRNA silencing pathways. *Cell* 117:69-81.

Ma, Z. et al. (2005). Cationic lipids enhance siRNA-mediated interferon response in mice. *Biochem Biophys Res Commun* 330:755-759.

Matzke, M. A. et al. (1989). Reversible methylation and inactivation of marker genes in sequentially transformed tobacco plants. *EMBO J.* 8: 643-649.

Mette, M. F. (2000). Transcriptional silencing and promoter methylation triggered by double-stranded RNA. *EMBO Journal* 19:5194-5201.

Miyagishi, M. and Taira, K. (2002). U6 promoter driven siRNAs with four uridine 3' overhangs efficiently suppress targeted gene expression in mammalian cells. *Nat Biotechnol* 20(5):497-500.

Moriuchi, H. et al. (1997). Cloning and analysis of the promoter region of CCR5, a coreceptor for HIV-1 entry. *J Immunol* 159:5441-5449 (1997).

Morris, K. V. et al. (2003). The effects of HHV-8 vMIP-II on SIVmac251 infection and replication competent and incompetent SIVmac239Delta3 vectors. *Virus Res* 94:103-112.

Morris, K. V. et al. (2004a). Transduction of cell lines and primary cells by FIV-packaged HIV vectors. *Mol Ther* 10:181-190.

Morris, K. V. et al. (2004b). Small interfering RNA-induced transcriptional gene silencing in human cells. *Science* 305: 1289-1292.

Morris, M. C. et al. (1997). A new peptide vector for efficient delivery of oligonucleotides into mammalian cells. *Nucleic Acids Res* 25:2730-2736.

Mummidi, S. et al. (1997). The human CC chemokine receptor 5 (CCR5) gene. Multiple transcripts with 5'-end heterogeneity, dual promoter usage, and evidence for polymorphisms within the regulatory regions and noncoding exons. *J Biol Chem* 272:30662-30671.

Mutskov, V. and Felsenfeld, G. (2004). Silencing of transgene transcription precedes methylation of promoter DNA and histone H3 lysine 9. *EMBO J* 23:138-149.

Nielsen, A. L. et al. (2001). Heterochromatin formation in mammalian cells: interaction between histones and HP1 proteins. *Mol Cell* 7:729-739.

Pal-Bhadra, M et al. (2002). RNAi related mechanisms affect both transcriptional and posttranscriptional transgene silencing in *Drosophila*. *Molecular Cell* 9(2):315-327.

Paul, C. P. et al. (2002). Effective expression of small interfering RNA in human cells. *Nat Biotechnol* 20(5):505-508.

Pham, J. W. et al. (2004). A Dicer-2-dependent 80s complex cleaves targeted mRNAs during RNAi in *Drosophila*. *Cell* 117:83-94.

Platt, E. J. et al. (1998). Effects of CCR5 and CD4 cell surface concentrations on infections by macrophagetropic isolates of human immunodeficiency virus type 1. *J Virol* 72:2855-2864.

Reynolds, A. et al. (2004). Rational siRNA design for RNA interference. *Nat Biotechnol* 22:326-330.

Rosati, M. et al. (2001). CCAAT-enhancer-binding protein beta (C/EBP beta) activates CCR5 promoter: increased C/EBP beta and CCR5 in T lymphocytes from HIV-1-infected individuals. *J Immunol* 167:1654-1662.

Rose, S. D. et al. (2005). Functional polarity is introduced by Dicer processing of short substrate RNAs. *Nucleic Acids Research* 33(13):4140-4156.

Rusckowski, M. et al. (2000). Biodistribution and metabolism of a mixed backbone oligonucleotide (GEM 231) following single and multiple dose administration in mice. *Antisense Nucleic Acid Drug Dev* 10:333-345.

Schramke, V. and Allshire, R. (2003). Hairpin RNAs and retrotransposon LTRs effect RNAi and chromatin-based gene silencing. *Science* 301:1069-1074.

Seitz, H. et al. (2003). Imprinted microRNA genes transcribed antisense to a reciprocally imprinted retrotransposon-like gene. *Nat Genet.* 34:261-262.

Sledz, C. A. et al. (2003). Activation of the interferon system by short-interfering RNAs. *Nature Cell Biol* 5:834-839.

Soifer, H. S. (2005). A potential role for RNA interference in controlling the activity of the human LINE-1 retrotransposon. *Nucleic Acids Res* 33:846-856.

Sontheimer, E. J. (2005). Assembly and function of RNA silencing complexes. *Nature Rev Mol Cell Biol*, 6:127-138.

Stein, D. A. et al. (2001) Inhibition of Vesivirus infections in mammalian tissue culture with antisense morpholino oligomers. *Antisense Nucleic Acid Drug Dev* 11:317-25.

Strahl-Bolsinger, S. et al. (1997). SIR2 and SIR4 interactions differ in core and extended telomeric heterochromatin in yeast. *Genes Dev* 11:83-93.

Tomari, Y. et al. (2004). A protein sensor for siRNA asymmetry. *Science* 306:1377-1380.

Unwalla, H. J. et al. (2004). Negative feedback inhibition of HIV-1 by TAT-inducible expression of siRNA. *Nat Biotechnol* 22:1573-1578.

Vermeulen, A. et al. (2005). The contributions of dsRNA structure to Dicer specificity and efficiency. *RNA* 11:674-682.

Vire, E. et al. (2006). "The Polycomb group protein EZH2 directly controls DNA methylation." *Nature* 439(7078): 871-874.

Volpe, T. A. (2002). Regulation of heterochromatic silencing and histone H3 lysine-9 methylation by RNAi. *Science* 297:1833-1837.

Vorobjev, P. E. et al. (2001). Nuclease resistance and RNase H sensitivity of oligonucleotides bridged by oligomethylenediol and oligoethylene glycol linkers. *Antisense Nucleic Acid Drug Dev* 11:77-85.

Wassenegger, M. (2000). RNA-directed DNA methylation. *Plant Mol Biol* 43:203-220.

Wassenegger, M., et al. (1994). RNA-directed de novo methylation of genomic sequences in plants. *Cell* 76:567-576 (1994).

Wei, X. et al. (2002). Emergence of resistant human immunodeficiency virus type 1 in patients receiving fusion inhibitor (T-20) monotherapy. *Antimicrob Agents Chemother* 46:1896-1905.

Xie, S. et al. (1999). Cloning, expression and chromosome locations of the human DNMT3 gene family. *Gene* 236: 87-95.

Weinberg, M. S. et al. (2006). The antisense strand of small interfering RNAs directs histone methylation and transcriptional gene silencing in human cells. *RNA* 12:256-262.

Yu, J. Y. et al. (2002). RNA interference by expression of short-interfering RNAs and hairpin RNAs in mammalian cells. *Proc Natl Acad Sci USA* 99(9):6047-6052.

Zhang, Y. et al. (1999). Analysis of the NuRD subunits reveals a histone deacetylase core complex and a connection with DNA methylation. *Genes Dev* 13:1924-1935.

Zilberman, D. et al. (2003). ARGONAUTE4 control of locus-specific siRNA accumulation and DNA and histone methylation. *Science* 299:716-719.

What is claimed is:

1. An isolated double stranded nucleic acid comprising first and second oligonucleotide strands, each strand comprising ribonucleotides and having a 5' terminus and a 3' terminus, wherein the first strand has a length which is 19-30 nucleotides and the second strand has a length which is 19-30 nucleotides, wherein the double-stranded nucleic acid comprises a duplex region of 19-30 nucleotides in length, wherein the second oligonucleotide strand comprises a sequence that hybridizes to a low copy promoter-specific RNA of a target gene, and wherein the isolated double stranded nucleic acid reduces target gene expression when introduced into a mammalian cell by inducing methylation of histones associated with the target gene.

2. The isolated double stranded nucleic acid of claim 1, wherein the duplex regions is 24-28 nucleotides in length.

3. The isolated double stranded nucleic acid of claim 1, wherein the duplex region is 19-23 nucleotides in length.

4. The isolated double stranded nucleic acid of claim 1, wherein the duplex region is 26 nucleotides in length.

5. The isolated double stranded nucleic acid of claim 1, wherein the duplex region is 25 nucleotides in length.

6. The isolated double stranded nucleic acid of claim 1, wherein the second strand is complementary to a sequence in the promoter of the target gene.

7. The isolated double stranded nucleic acid of claim 6, wherein the sequence in the promoter of the target gene is between 150 nucleotides upstream of the transcription start site and the transcription start site.

8. A composition comprising an isolated double stranded nucleic acid and a carrier, wherein the isolated double stranded nucleic acid comprises first and second oligonucleotide strands, each strand comprising ribonucleotides and having a 5' terminus and a 3' terminus, wherein the first strand has a length which is 19-30 nucleotides and the second strand has a length which is 19-30 nucleotides, wherein the double-stranded nucleic acid comprises a duplex region of 19-30 nucleotides in length, wherein the second oligonucleotide strand comprises a sequence that hybridizes to a low copy promoter-specific RNA of a target gene, and wherein the isolated double stranded nucleic acid reduces target gene expression when introduced into a mammalian cell by inducing methylation of histones associated with the target gene.

9. The isolated double stranded nucleic acid of claim 8, wherein the duplex regions is 24-28 nucleotides in length.

10. The isolated double stranded nucleic acid of claim 8, wherein the duplex region is 19-23 nucleotides in length.

11. The isolated double stranded nucleic acid of claim 8, wherein the duplex region is 26 nucleotides in length.

12. The isolated double stranded nucleic acid of claim 8, wherein the duplex region is 25 nucleotides in length.

13. The isolated double stranded nucleic acid of claim 8, wherein the second strand is complementary to a sequence in the promoter of the target gene.

14. The isolated double stranded nucleic acid of claim 13, wherein the sequence in the promoter of the target gene is between 150 nucleotides upstream of the transcription start site and the transcription start site.

\* \* \* \* \*

UNITED STATES PATENT AND TRADEMARK OFFICE
CERTIFICATE OF CORRECTION

PATENT NO. : 8,513,401 B2
APPLICATION NO. : 12/772652
DATED : August 20, 2013
INVENTOR(S) : John J. Rossi et al.

It is certified that error appears in the above-identified patent and that said Letters Patent is hereby corrected as shown below:

In the Specification

Column 30, Table 2, sequence 30, "CTTTCCGGTGGGGACTTTC" should be
-- CTTTCCGCTGGGGACTTTC --

Signed and Sealed this
Tenth Day of April, 2018

Andrei Iancu
*Director of the United States Patent and Trademark Office*

UNITED STATES PATENT AND TRADEMARK OFFICE
CERTIFICATE OF CORRECTION

| | |
|---|---|
| PATENT NO. | : 8,513,401 B2 |
| APPLICATION NO. | : 12/772652 |
| DATED | : August 20, 2013 |
| INVENTOR(S) | : John J. Rossi et al. |

It is certified that error appears in the above-identified patent and that said Letters Patent is hereby corrected as shown below:

In the Specification

Column 1, Lines 19-24:
"This application was made with Government support under Grant Nos. AI29329, AI42552, R01 HL07470 and R01 HL83473 funded by the National Institutes of Health, Bethesda, Md. and under Grant No. 5P30 CA33572-21 funded by the National Cancer Institute, Bethesda Md. The federal government may have certain rights in this invention."
Should be:
-- This invention was made with government support under HL083473, AI029329, AI042552, and HL007470 awarded by the National Institutes of Health. The government has certain rights in the invention. --

Signed and Sealed this
Fifth Day of November, 2024

Katherine Kelly Vidal
*Director of the United States Patent and Trademark Office*

SEQUENCE LISTING

<160> NUMBER OF SEQ ID NOS: 52

<210> SEQ ID NO 1
<211> LENGTH: 176
<212> TYPE: DNA
<213> ORGANISM: Homo sapiens

<400> SEQUENCE: 1
ggggctctgc gagagcgcgc ccagccccgc cttcgggccc cacagtccct gcacccaggt     60
ttccattgcg cggctctcct cagctccttc ccgccgccca gtctggatcc tgggggaggc    120
gctgaagtcg gggcccgccc tgtggccccg cccggcccgc gcttgctagc gcccaa        176

<210> SEQ ID NO 2
<211> LENGTH: 180
<212> TYPE: DNA
<213> ORGANISM: Homo sapiens

<400> SEQUENCE: 2
ggggctctgc gagagcgcgc ccagccccgc cttcgggccc cacagtccct gcacccaggt     60
ttccattgcg cggctctcct cagctccttc ccgccgccca gtctggatcc tgggggaggc    120
gctgaagtcg gggcccgccc tgtggccccg cccggcccgc gcttgctagc gcccaaagcc    180

<210> SEQ ID NO 3
<211> LENGTH: 300
<212> TYPE: DNA
<213> ORGANISM: Homo sapiens

<400> SEQUENCE: 3
agcgaagcac gggcccaacc gggccatgtc gggggagcct gagctcattg agctgcggga     60
gctggcaccc gctgggcgcg ctgggaaggg ccgcacccgg ctggagcgtg ccaacgcgct    120
gcgcatcgcg cggggcaccg cgtgcaaccc cacacgcgca ctggtccctg ccgtggcca    180 ccgcttccag cccgcggggc ccgccacgca cacgtggtgc gacctctgtg gcgacttcat    240
ctggggcgtc gtgcgcaaag gcctgcagtg cgcgcgtgag tagtggcccc gcgcgcctac    300

<210> SEQ ID NO 4
<211> LENGTH: 41
<212> TYPE: DNA
<213> ORGANISM: Artificial
<220> FEATURE:
<223> OTHER INFORMATION: PCR primer

<400> SEQUENCE: 4
aatcgaacgc gtggatccaa ggtcgggcag gaagagggcc t                         41

<210> SEQ ID NO 5
<211> LENGTH: 20
<212> TYPE: DNA
<213> ORGANISM: Homo sapiens

<400> SEQUENCE: 5
gtggaaagga cgaaacaccg                                                 20

<210> SEQ ID NO 6
<211> LENGTH: 51
<212> TYPE: DNA
<213> ORGANISM: Artificial
<220> FEATURE:
<223> OTHER INFORMATION: PCR primer -continued

```
<400> SEQUENCE: 6
ctacacaaag cgggccccg acttcagcgc ggtgtttcgt cctttccaca a          51

<210> SEQ ID NO 7
<211> LENGTH: 47
<212> TYPE: DNA
<213> ORGANISM: Artificial
<220> FEATURE:
<223> OTHER INFORMATION: PCR primer

<400> SEQUENCE: 7
aactcgaatt caaaaaagcg ctgaagtcgg ggcccgccct acacaaa             47

<210> SEQ ID NO 8
<211> LENGTH: 51
<212> TYPE: DNA
<213> ORGANISM: Artificial
<220> FEATURE:
<223> OTHER INFORMATION: PCR primer

<400> SEQUENCE: 8
ctacacaaac gacatggccc ggttgggccc ggtgtttcgt cctttccaca a          51

<210> SEQ ID NO 9
<211> LENGTH: 47
<212> TYPE: DNA
<213> ORGANISM: Artificial
<220> FEATURE:
<223> OTHER INFORMATION: PCR primer

<400> SEQUENCE: 9
aactcgaatt caaaaaaggg cccaaccggg ccatgtcgct acacaaa             47

<210> SEQ ID NO 10
<211> LENGTH: 18
<212> TYPE: DNA
<213> ORGANISM: Artificial
<220> FEATURE:
<223> OTHER INFORMATION: MSP primer

<400> SEQUENCE: 10
gggttttgcg agagcgcg                                             18

<210> SEQ ID NO 11
<211> LENGTH: 18
<212> TYPE: DNA
<213> ORGANISM: Artificial
<220> FEATURE:
<223> OTHER INFORMATION: MSP primer

<400> SEQUENCE: 11
gctaacaaac gcgaaccg                                             18

<210> SEQ ID NO 12
<211> LENGTH: 24
<212> TYPE: DNA
<213> ORGANISM: Artificial
<220> FEATURE:
<223> OTHER INFORMATION: MSP primer

<400> SEQUENCE: 12
ggggttttgt gagagtgtgt ttag                                      24

<210> SEQ ID NO 13
<211> LENGTH: 26
<212> TYPE: DNA
```

-continued

```
<213> ORGANISM: Artificial
<220> FEATURE:
<223> OTHER INFORMATION: MSP primer

<400> SEQUENCE: 13
taaacactaa caaacacaaa ccaaac                                           26

<210> SEQ ID NO 14
<211> LENGTH: 51
<212> TYPE: DNA
<213> ORGANISM: Artificial
<220> FEATURE:
<223> OTHER INFORMATION: PCR primer

<400> SEQUENCE: 14
ctacacaaac gatatggcgg ccttgggccc ggtgtttcgt cctttccaca a               51

<210> SEQ ID NO 15
<211> LENGTH: 47
<212> TYPE: DNA
<213> ORGANISM: Artificial
<220> FEATURE:
<223> OTHER INFORMATION: PCR primer

<400> SEQUENCE: 15
aactcgaatt caaaaaggg cccaaggccg ccatatcgct acacaaa                     47

<210> SEQ ID NO 16
<211> LENGTH: 21
<212> TYPE: DNA
<213> ORGANISM: Homo sapiens

<400> SEQUENCE: 16
aaggtggcgc ggggtaaact g                                                21

<210> SEQ ID NO 17
<211> LENGTH: 21
<212> TYPE: DNA
<213> ORGANISM: Aequorea victoria

<400> SEQUENCE: 17
aacgatgcca cctacggcaa g                                                21

<210> SEQ ID NO 18
<211> LENGTH: 21
<212> TYPE: DNA
<213> ORGANISM: homo sapiens

<400> SEQUENCE: 18
aattctttgg cctgaataat t                                                21

<210> SEQ ID NO 19
<211> LENGTH: 21
<212> TYPE: RNA
<213> ORGANISM: homo sapiens

<400> SEQUENCE: 19
ccaccgcgcc ccauuugaca a                                                21

<210> SEQ ID NO 20
<211> LENGTH: 21
<212> TYPE: RNA
<213> ORGANISM: homo sapiens

<400> SEQUENCE: 20
```
aagguggcgc ggggualaacu g                                              21

<210> SEQ ID NO 21
<211> LENGTH: 49
<212> TYPE: DNA
<213> ORGANISM: Artificial
<220> FEATURE:
<223> OTHER INFORMATION: PCR primer

<400> SEQUENCE: 21
aaaaaaaagt gttagagtgg aggtttgcgg tgtttcgtcc tttccacaa                 49

<210> SEQ ID NO 22
<211> LENGTH: 49
<212> TYPE: DNA
<213> ORGANISM: Artificial
<220> FEATURE:
<223> OTHER INFORMATION: PCR primer

<400> SEQUENCE: 22
aaaaaaaaga aagtccccag cggaaagcgg tgtttcgtcc tttccacaa                 49

<210> SEQ ID NO 23
<211> LENGTH: 49
<212> TYPE: DNA
<213> ORGANISM: Artificial
<220> FEATURE:
<223> OTHER INFORMATION: PCR primer

<400> SEQUENCE: 23
aaaaaaaacg atgccaccta cggcaagcgg tgtttcgtcc tttccacaa                 49

<210> SEQ ID NO 24
<211> LENGTH: 49
<212> TYPE: DNA
<213> ORGANISM: Artificial
<220> FEATURE:
<223> OTHER INFORMATION: PCR primer

<400> SEQUENCE: 24
aaaaaaaact tgccgtaggt ggcatcgcgg tgtttcgtcc tttccacaa                 49

<210> SEQ ID NO 25
<211> LENGTH: 49
<212> TYPE: DNA
<213> ORGANISM: Artificial
<220> FEATURE:
<223> OTHER INFORMATION: PCR primer

<400> SEQUENCE: 25
aaaaaaaagt attaaagtgg aagtttgcgg tgtttcgtcc tttccacaa                 49

<210> SEQ ID NO 26
<211> LENGTH: 48
<212> TYPE: DNA
<213> ORGANISM: Artificial
<220> FEATURE:
<223> OTHER INFORMATION: PCR primer

<400> SEQUENCE: 26
aaaaaaaaca aacttccact ttaatacggt gtttcgtcct ttccacaa                  48

<210> SEQ ID NO 27
<211> LENGTH: 48
<212> TYPE: DNA
<213> ORGANISM: Artificial
<220> FEATURE:

```
<223> OTHER INFORMATION: PCR primer

<400> SEQUENCE: 27
aaaaaaaact ttccactggg gcgttccggt gtttcgtcct ttccacaa         48

<210> SEQ ID NO 28
<211> LENGTH: 49
<212> TYPE: DNA
<213> ORGANISM: Artificial
<220> FEATURE:
<223> OTHER INFORMATION: PCR primer

<400> SEQUENCE: 28 aaaaaaagg aacgccccag tggaaagcgg tgtttcgtcc tttccacaa          49

<210> SEQ ID NO 29
<211> LENGTH: 19
<212> TYPE: DNA
<213> ORGANISM: Human immunodeficiency virus

<400> SEQUENCE: 29
gtgttagagt ggaggtttg                                         19

<210> SEQ ID NO 30
<211> LENGTH: 19
<212> TYPE: DNA
<213> ORGANISM: Human immunodeficiency virus

<400> SEQUENCE: 30
ctttccgctg gggactttc                                         19

<210> SEQ ID NO 31
<211> LENGTH: 19
<212> TYPE: DNA
<213> ORGANISM: Human immunodeficiency virus

<400> SEQUENCE: 31
gtattaaagt ggaagtttg                                         19

<210> SEQ ID NO 32
<211> LENGTH: 19
<212> TYPE: DNA
<213> ORGANISM: Human immunodeficiency virus

<400> SEQUENCE: 32
ctttccactg gggcgttcc                                         19

<210> SEQ ID NO 33
<211> LENGTH: 19
<212> TYPE: DNA
<213> ORGANISM: Aequorea victoria

<400> SEQUENCE: 33
cgatgccacc tacggcaag                                         19

<210> SEQ ID NO 34
<211> LENGTH: 19
<212> TYPE: DNA
<213> ORGANISM: homo sapiens

<400> SEQUENCE: 34
ttctttggcc tgaataatt                                         19

<210> SEQ ID NO 35
```

```
<211> LENGTH: 21
<212> TYPE: RNA
<213> ORGANISM: Artificial
<220> FEATURE:
<223> OTHER INFORMATION: siRNA sense strand

<400> SEQUENCE: 35
gccaaagcuu uuuauucuaa a                                              21

<210> SEQ ID NO 36
<211> LENGTH: 21
<212> TYPE: RNA
<213> ORGANISM: Artificial
<220> FEATURE:
<223> OTHER INFORMATION: siRNA antisense strand

<400> SEQUENCE: 36
uagaauaaaa agcuuuggca a                                              21

<210> SEQ ID NO 37
<211> LENGTH: 21
<212> TYPE: RNA
<213> ORGANISM: Artificial
<220> FEATURE:
<223> OTHER INFORMATION: siRNA sense strand

<400> SEQUENCE: 37
gcccagaggg caucuuguga a                                              21

<210> SEQ ID NO 38
<211> LENGTH: 21
<212> TYPE: RNA
<213> ORGANISM: Artificial
<220> FEATURE:
<223> OTHER INFORMATION: siRNA antisense strand

<400> SEQUENCE: 38
cacaagaugc ccucgggca a                                               21

<210> SEQ ID NO 39
<211> LENGTH: 21
<212> TYPE: RNA
<213> ORGANISM: Artificial
<220> FEATURE:
<223> OTHER INFORMATION: siRNA sense strand

<400> SEQUENCE: 39
ccgccaagag agcuugauaa a                                              21

<210> SEQ ID NO 40
<211> LENGTH: 21
<212> TYPE: RNA
<213> ORGANISM: Artificial
<220> FEATURE:
<223> OTHER INFORMATION: siRNA antisense strand

<400> SEQUENCE: 40
uaucaagcuc ucuuggcgga a                                              21

<210> SEQ ID NO 41
<211> LENGTH: 21
<212> TYPE: RNA
<213> ORGANISM: Artificial
<220> FEATURE:
<223> OTHER INFORMATION: siRNA sense strand

<400> SEQUENCE: 41
```
gcccguaaau aaacuuucaa a                                        21

<210> SEQ ID NO 42
<211> LENGTH: 21
<212> TYPE: RNA
<213> ORGANISM: Artificial
<220> FEATURE:
<223> OTHER INFORMATION: siRNA antisense strand

<400> SEQUENCE: 42
ugaaaguuua uuuacgggca a                                        21

<210> SEQ ID NO 43
<211> LENGTH: 21
<212> TYPE: RNA
<213> ORGANISM: Artificial
<220> FEATURE:
<223> OTHER INFORMATION: siRNA sense strand

<400> SEQUENCE: 43
aauucuuugg ccugaauaaa a                                        21

<210> SEQ ID NO 44
<211> LENGTH: 21
<212> TYPE: RNA
<213> ORGANISM: Artificial
<220> FEATURE:
<223> OTHER INFORMATION: siRNA antisense strand

<400> SEQUENCE: 44
uuauucaggc caaagaauua a                                        21

<210> SEQ ID NO 45
<211> LENGTH: 30
<212> TYPE: DNA
<213> ORGANISM: Artificial
<220> FEATURE:
<223> OTHER INFORMATION: PCR Primer

<400> SEQUENCE: 45
ggggtctcat ttgccttctt agagatcaca                               30

<210> SEQ ID NO 46
<211> LENGTH: 25
<212> TYPE: DNA
<213> ORGANISM: Artificial
<220> FEATURE:
<223> OTHER INFORMATION: PCR primer

<400> SEQUENCE: 46
taagtatatg gtcaagttca ggttc                                    25

<210> SEQ ID NO 47
<211> LENGTH: 26
<212> TYPE: DNA
<213> ORGANISM: Artificial
<220> FEATURE:
<223> OTHER INFORMATION: PCR primer

<400> SEQUENCE: 47
gtcttctcag ctctgctgac aatact                                   26

<210> SEQ ID NO 48
<211> LENGTH: 30
<212> TYPE: DNA
<213> ORGANISM: Artificial
<220> FEATURE:

<223> OTHER INFORMATION: PCR primer

<400> SEQUENCE: 48
ggattttcac tctgttcact attttgttgc        30

<210> SEQ ID NO 49
<211> LENGTH: 30
<212> TYPE: DNA
<213> ORGANISM: Artificial
<220> FEATURE:
<223> OTHER INFORMATION: PCR primer

<400> SEQUENCE: 49
gaaggaaggg caaggcgggg ggggctctgc        30

<210> SEQ ID NO 50
<211> LENGTH: 25
<212> TYPE: DNA
<213> ORGANISM: Artificial
<220> FEATURE:
<223> OTHER INFORMATION: PCR primer

<400> SEQUENCE: 50
ggcccggttg ggcccgtgct tcgct        25

<210> SEQ ID NO 51
<211> LENGTH: 23
<212> TYPE: DNA
<213> ORGANISM: Artificial
<220> FEATURE:
<223> OTHER INFORMATION: PCR primer

<400> SEQUENCE: 51
tggtgcgacc tctgtggcga ctt        23

<210> SEQ ID NO 52
<211> LENGTH: 26
<212> TYPE: DNA
<213> ORGANISM: Artificial
<220> FEATURE:
<223> OTHER INFORMATION: PCR primer

<400> SEQUENCE: 52
gatgaagcct gtgtaagaac cgtcct        26